US009326686B2

(12) United States Patent
Warren et al.

(10) Patent No.: US 9,326,686 B2
(45) Date of Patent: May 3, 2016

(54) SYSTEM AND METHOD FOR MITIGATING THE EFFECTS OF TISSUE BLOOD VOLUME CHANGES TO AID IN DIAGNOSING INFILTRATION OR EXTRAVASATION IN ANIMALIA TISSUE

(71) Applicant: ivWatch, LLC, Williamsburg, VA (US)

(72) Inventors: Gary P. Warren, Williamsburg, VA (US); Matthew S. Alley, Sandston, VA (US); Scott J. Anchell, Fairfax Station, VA (US); Javier A. Garriz, Hampton, VA (US); William J. Naramore, Richmond, VA (US); Garret T. Bonnema, Williamsburg, VA (US)

(73) Assignee: ivWatch, LLC, Hampton, VA (US)

( * ) Notice: Subject to any disclaimer, the term of this patent is extended or adjusted under 35 U.S.C. 154(b) by 0 days.

(21) Appl. No.: 13/954,961

(22) Filed: Jul. 30, 2013

(65) Prior Publication Data
US 2013/0338511 A1  Dec. 19, 2013

Related U.S. Application Data

(63) Continuation-in-part of application No. 13/794,776, filed on Mar. 11, 2013, now abandoned, and a continuation-in-part of application No. 13/792,193, filed on Mar. 11, 2013, now abandoned, and a
(Continued)

(51) Int. Cl.
*A61B 5/00* (2006.01)
*A61M 5/168* (2006.01)
(Continued)

(52) U.S. Cl.
CPC ............. *A61B 5/0075* (2013.01); *A61B 5/0082* (2013.01); *A61B 5/0507* (2013.01);
(Continued)

(58) Field of Classification Search
CPC ................... A61B 2562/0233; A61B 2562/12; A61B 2562/187; A61B 2562/247; A61B 5/0075; A61B 5/0082; A61B 5/0507; A61B 5/14552; A61B 5/441; A61B 5/443; A61B 5/6832; A61F 13/02; A61F 13/0276; A61M 2005/17
USPC .................................................. 600/473–478
See application file for complete search history.

(56) References Cited

U.S. PATENT DOCUMENTS 3,618,602 A * 11/1971 Shaw ............................ 604/503
4,010,749 A    3/1977 Shaw
(Continued)

FOREIGN PATENT DOCUMENTS

FR        2374917        7/1978
JP     2004194802 A      7/2004
(Continued)

OTHER PUBLICATIONS

Du, Congwu et al. Simultaneous Detection of Blood Volume, Oxygenation, and Intracellular Calcium Changes During Cerebral Ischemia and Reperfusion in vivo using Diffuse Reflectance and Fluorescence. Journal of Cerebral Blood Flow & Metabolism: 25(2005), 1078-1092.*
(Continued)

*Primary Examiner* — Amanda Lauritzen Moher

(57) ABSTRACT

A system including a sensor and a device coupled to the sensor. The sensor is configured to detect in Animalia tissue (i) a first electromagnetic radiation extinction dominated by absorption of a first wavelength and (ii) a second electromagnetic radiation extinction dominated by scattering of a second wavelength. The device is configured to aid in diagnosing at least one of infiltration and extravasation in the Animalia tissue based on the first and second electromagnetic radiation extinctions detected by the sensor.

3 Claims, 43 Drawing Sheets

Related U.S. Application Data continuation-in-part of application No. 13/792,074, filed on Mar. 10, 2013, now abandoned, and a continuation-in-part of application No. 13/792,079, filed on Mar. 10, 2013, now abandoned, and a continuation-in-part of application No. 13/792,051, filed on Mar. 9, 2013, now abandoned, and a continuation-in-part of application No. 13/792,068, filed on Mar. 10, 2013, now abandoned.

(60) Provisional application No. 61/609,865, filed on Mar. 12, 2012, provisional application No. 61/640,542, filed on Apr. 30, 2012, provisional application No. 61/706,726, filed on Sep. 27, 2012, provisional application No. 61/755,273, filed on Jan. 22, 2013, provisional application No. 61/809,651, filed on Apr. 8, 2013.

(51) Int. Cl.
*A61M 5/50* (2006.01)
*A61F 13/02* (2006.01)
*A61B 5/1455* (2006.01)
*A61B 5/05* (2006.01)
*A61M 5/172* (2006.01)

(52) U.S. Cl.
CPC ............ *A61B5/14552* (2013.01); *A61B 5/441* (2013.01); *A61B 5/443* (2013.01); *A61B 5/6832* (2013.01); *A61F 13/02* (2013.01); *A61F 13/0276* (2013.01); *A61M 5/16836* (2013.01); *A61M 5/5086* (2013.01); *A61B 2562/0233* (2013.01); *A61B 2562/12* (2013.01); *A61B 2562/187* (2013.01); *A61B 2562/247* (2013.01); *A61M 2005/1726* (2013.01)

(56) References Cited

U.S. PATENT DOCUMENTS

| | | |
|---|---|---|
| 4,122,838 A | 10/1978 | Leonard |
| 4,378,808 A | 4/1983 | Lichtenstein |
| 4,647,281 A | 3/1987 | Carr |
| 4,743,228 A | 5/1988 | Butterfield |
| 4,773,422 A | 9/1988 | Isaacson |
| 4,816,019 A | 3/1989 | Kamen |
| 4,846,792 A | 7/1989 | Bobo, Jr. |
| 4,877,034 A | 10/1989 | Atkins |
| 4,898,576 A | 2/1990 | Philip |
| 4,959,050 A | 9/1990 | Bobo, Jr. |
| 4,979,940 A | 12/1990 | Bobo, Jr. |
| 5,334,141 A | 8/1994 | Carr |
| 5,490,523 A | 2/1996 | Isaacson |
| 5,947,910 A | 9/1999 | Zimmet |
| 5,954,668 A | 9/1999 | Uber, III |
| 5,964,703 A | 10/1999 | Goodman |
| 6,408,204 B1 | 6/2002 | Hirschman |
| 6,425,878 B1 | 7/2002 | Shekalim |
| 6,675,029 B2 | 1/2004 | Monfre |
| 6,751,500 B2 | 6/2004 | Hirschman |
| 6,771,994 B2 | 8/2004 | Kiani |
| 6,822,564 B2 | 11/2004 | Al-Ali |
| RE38,695 E | 2/2005 | Goodman |
| RE38,879 E | 11/2005 | Goodman |
| 7,047,054 B2 | 5/2006 | Benni |
| 7,047,058 B1 | 5/2006 | Dvorsky |
| 7,122,012 B2 | 10/2006 | Bouton |
| 7,142,901 B2 | 11/2006 | Kiani |
| 7,169,107 B2 | 1/2007 | Jersey-Willuhn |
| 7,184,820 B2 | 2/2007 | Jersey-Willuhn |
| 7,239,385 B2 | 7/2007 | Schmitz |
| 7,239,901 B2 | 7/2007 | Gritsenko |
| 7,259,851 B2 | 8/2007 | Wang |
| 7,263,394 B2 | 8/2007 | Wang |
| 7,280,858 B2 | 10/2007 | Al-Ali |
| 7,295,866 B2 | 11/2007 | Al-Ali |
| 7,313,427 B2 | 12/2007 | Benni |
| 7,383,069 B2 | 6/2008 | Ruchti |
| 7,392,074 B2 | 6/2008 | Isaacson |
| 7,456,965 B2 | 11/2008 | Wang |
| 7,471,969 B2 | 12/2008 | Diab |
| 7,496,393 B2 | 2/2009 | Diab |
| 7,500,950 B2 | 3/2009 | Al-Ali |
| 7,509,153 B2 | 3/2009 | Blank |
| 7,519,406 B2 | 4/2009 | Blank |
| 7,536,214 B2 | 5/2009 | Myers |
| 7,546,776 B2 | 6/2009 | Ono |
| 7,591,792 B2 | 9/2009 | Bouton |
| 7,595,879 B2 | 9/2009 | Wang |
| 7,613,489 B2 | 11/2009 | Myers |
| 7,674,244 B2 | 3/2010 | Kalafut |
| 7,787,924 B2 | 8/2010 | Acosta |
| 7,801,583 B2 | 9/2010 | Brabrand |
| 7,809,430 B2 | 10/2010 | Ono |
| 7,826,890 B1 | 11/2010 | Winchester, Jr. |
| 7,831,298 B1 | 11/2010 | Wang |
| 7,914,523 B2 | 3/2011 | Barolet |
| 7,957,780 B2 | 6/2011 | Lamego |
| 7,970,457 B2 | 6/2011 | Ono |
| 7,970,458 B2 | 6/2011 | Norris |
| 7,995,816 B2 | 8/2011 | Roger |
| 8,046,041 B2 | 10/2011 | Diab |
| 8,046,042 B2 | 10/2011 | Diab |
| 8,057,406 B2 | 11/2011 | Mohiuddin |
| 8,060,189 B2 | 11/2011 | Ben Dor |
| 8,073,518 B2 | 12/2011 | Chin |
| 8,100,834 B2 | 1/2012 | Shuler |
| 8,135,448 B2 | 3/2012 | Baker, Jr. |
| 8,175,665 B2 | 5/2012 | Baker, Jr. |
| 8,175,670 B2 | 5/2012 | Baker, Jr. |
| 8,180,419 B2 | 5/2012 | Debreczeny |
| 8,180,420 B2 | 5/2012 | Diab |
| 8,195,263 B2 | 6/2012 | Drebreczeny |
| 8,197,431 B2 | 6/2012 | Bennison |
| 8,235,949 B2 | 8/2012 | Hack |
| 8,255,028 B2 | 8/2012 | Al-Ali |
| 8,295,920 B2 | 10/2012 | Bouton |
| 8,320,999 B2 | 11/2012 | Ono |
| 8,560,034 B1 | 10/2013 | Diab |
| 2001/0012767 A1 | 8/2001 | Kim |
| 2002/0172323 A1 | 11/2002 | Karellas |
| 2003/0216662 A1 | 11/2003 | Jersey-Willuhn |
| 2004/0215081 A1 | 10/2004 | Crane |
| 2006/0173360 A1 | 8/2006 | Kalafut |
| 2006/0178616 A1 | 8/2006 | Hartman |
| 2007/0112329 A1 | 5/2007 | Sage |
| 2007/0276327 A1 | 11/2007 | Kalafut |
| 2009/0299191 A1 | 12/2009 | Hyun |
| 2010/0198141 A1 | 8/2010 | Laitenberger |
| 2011/0130668 A1 | 6/2011 | Ohyu |
| 2011/0257522 A1 | 10/2011 | Berard-Andersen |
| 2012/0123229 A1 | 5/2012 | Butterfield |
| 2013/0109967 A1 | 5/2013 | Park |
| 2013/0177455 A1 | 7/2013 | Kamen |
| 2013/0211329 A1 | 8/2013 | Kamatani |
| 2013/0232752 A1 | 9/2013 | Warren |
| 2013/0232759 A1 | 9/2013 | Warren |
| 2013/0232760 A1 | 9/2013 | Warren |
| 2013/0232761 A1 | 9/2013 | Warren |
| 2013/0237779 A1 | 9/2013 | Warren |
| 2013/0237787 A1 | 9/2013 | Warren |
| 2013/0237788 A1 | 9/2013 | Warren |
| 2013/0237812 A1 | 9/2013 | Warren |
| 2013/0237830 A1 | 9/2013 | Warren |
| 2013/0237831 A1 | 9/2013 | Warren |
| 2013/0237832 A1 | 9/2013 | Warren |
| 2013/0237833 A1 | 9/2013 | Warren |
| 2013/0237834 A1 | 9/2013 | Warren |
| 2013/0237835 A1 | 9/2013 | Warren |
| 2013/0237836 A1 | 9/2013 | Warren |
| 2013/0237837 A1 | 9/2013 | Warren |
| 2013/0237838 A1 | 9/2013 | Warren |
| 2013/0237839 A1 | 9/2013 | Warren |

(56) References Cited

U.S. PATENT DOCUMENTS

| | | |
|---|---|---|
| 2013/0237840 A1 | 9/2013 | Warren |
| 2013/0237844 A1 | 9/2013 | Warren |
| 2013/0237845 A1 | 9/2013 | Warren |
| 2013/0237846 A1 | 9/2013 | Warren |
| 2013/0237847 A1 | 9/2013 | Warren |
| 2013/0237848 A1 | 9/2013 | Warren |
| 2013/0237849 A1 | 9/2013 | Warren |
| 2013/0237850 A1 | 9/2013 | Warren |
| 2013/0237851 A1 | 9/2013 | Warren |
| 2013/0237852 A1 | 9/2013 | Warren |
| 2013/0237853 A1 | 9/2013 | Warren |
| 2013/0237854 A1 | 9/2013 | Warren |
| 2013/0237855 A1 | 9/2013 | Warren |
| 2013/0237856 A1 | 9/2013 | Warren |
| 2013/0237857 A1 | 9/2013 | Warren |
| 2013/0237858 A1 | 9/2013 | Warren |
| 2013/0310742 A1 | 11/2013 | Warren |
| 2013/0310743 A1 | 11/2013 | Yagi |
| 2013/0317368 A1 | 11/2013 | Warren |
| 2013/0317373 A1 | 11/2013 | Warren |
| 2013/0317441 A1 | 11/2013 | Warren |
| 2013/0317442 A1 | 11/2013 | Warren |
| 2013/0317443 A1 | 11/2013 | Warren |
| 2013/0317444 A1 | 11/2013 | Warren |
| 2013/0324854 A1 | 12/2013 | Alley |
| 2013/0331707 A1 | 12/2013 | Alley |
| 2013/0338462 A1 | 12/2013 | Warren |
| 2013/0338511 A1 | 12/2013 | Warren |
| 2013/0338512 A1 | 12/2013 | Warren |
| 2014/0243625 A1 | 8/2014 | Warren |
| 2014/0303474 A1 | 10/2014 | Warren |
| 2014/0303475 A1 | 10/2014 | Warren |
| 2014/0309535 A1 | 10/2014 | Warren |

FOREIGN PATENT DOCUMENTS

| | | |
|---|---|---|
| WO | WO-9915074 A1 | 4/1999 |
| WO | WO-9926686 A1 | 6/1999 |
| WO | WO-2004052431 A1 | 6/2004 |
| WO | WO-2007140199 A2 | 12/2007 |
| WO | WO-2009042562 A1 | 4/2009 |
| WO | WO-2009042577 A2 | 4/2009 |
| WO | WO-2009042621 A2 | 4/2009 |
| WO | WO-2009042624 A2 | 4/2009 |
| WO | WO-2011087059 A1 | 7/2011 |
| WO | WO-2012040630 A1 | 3/2012 |
| WO | WO-2013033162 A1 | 3/2013 |
| WO | WO-2013033166 A1 | 3/2013 |
| WO | WO-2013033174 A1 | 3/2013 |

OTHER PUBLICATIONS

Journal of Cerebral Blood Flow & Metabolism (2005) 25; pp. 1078-1092.

Warren, Gary P., et al.; "Apparatus for Mitigating Noise Affecting a Signal;" U.S. Appl. No. 14/314,471, filed Jun. 25, 2014.

* cited by examiner

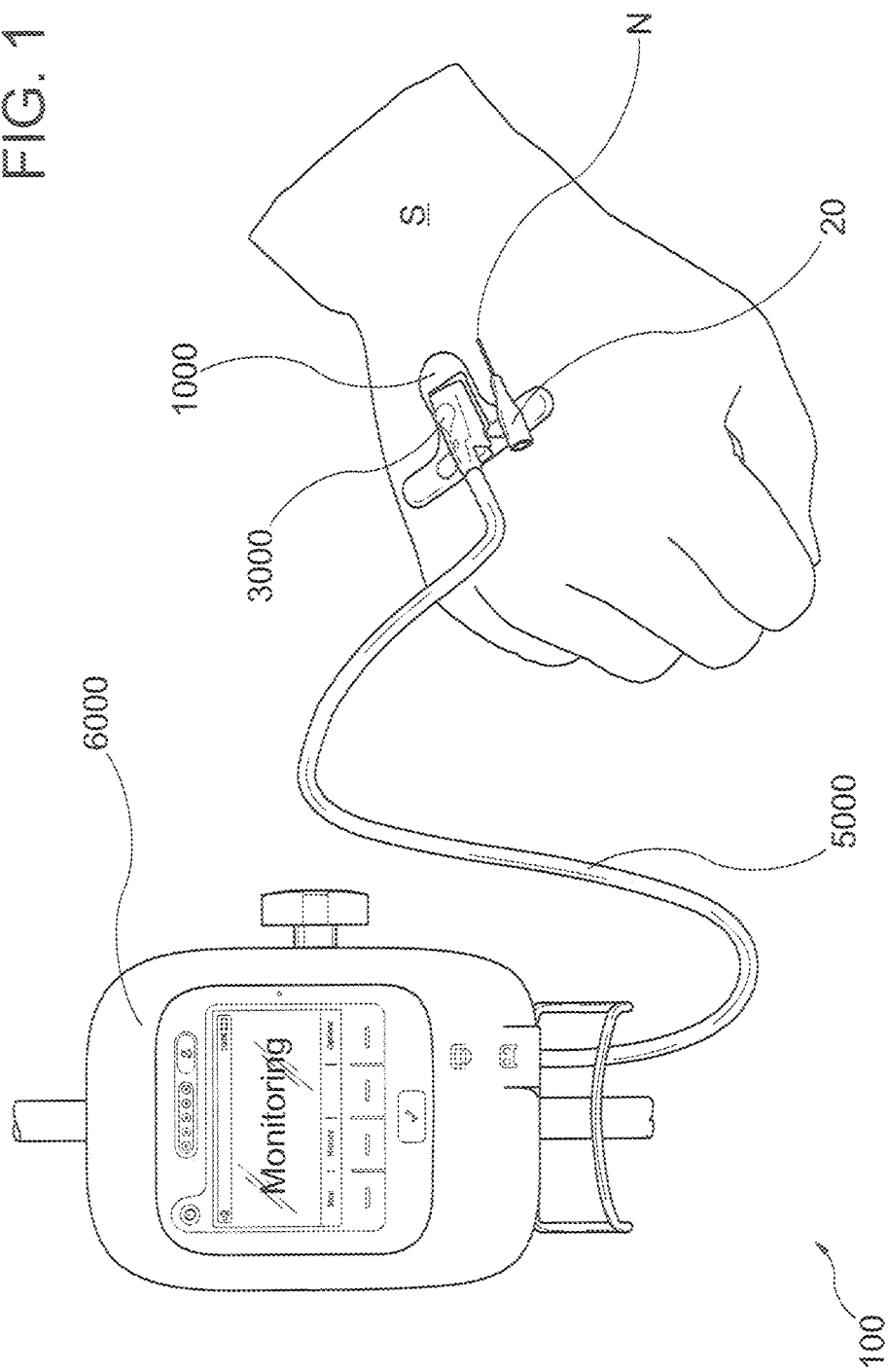

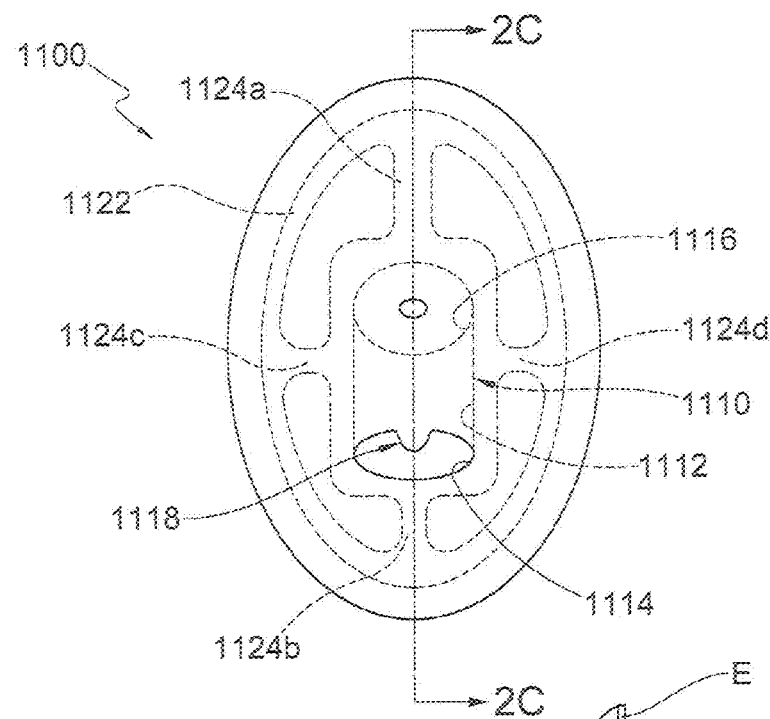
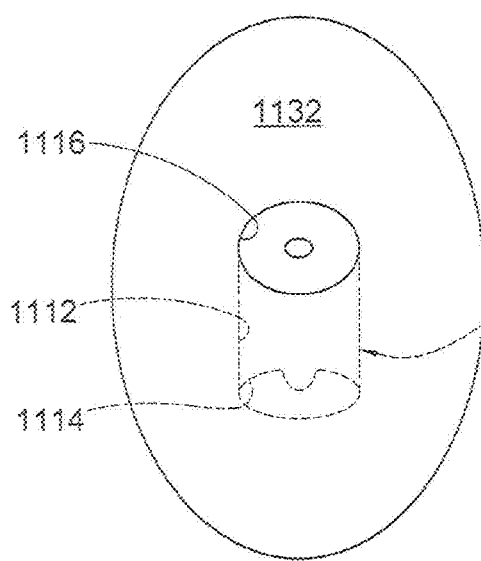
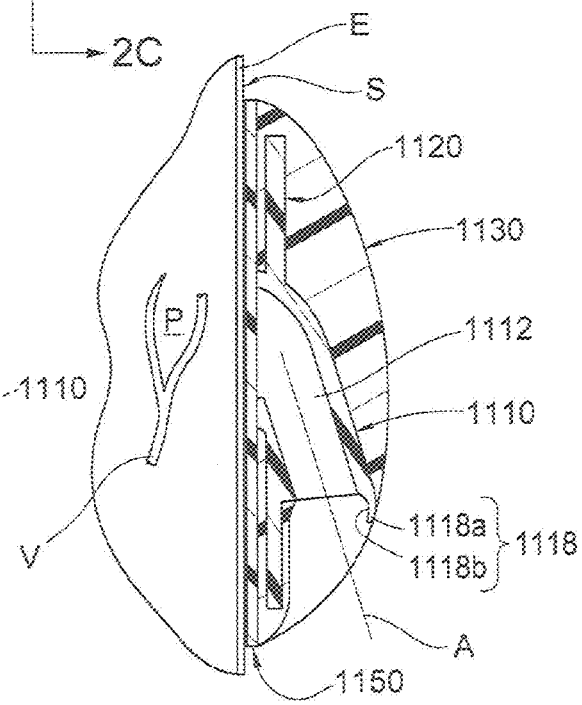
FIG. 2A
FIG. 2B
FIG. 2C

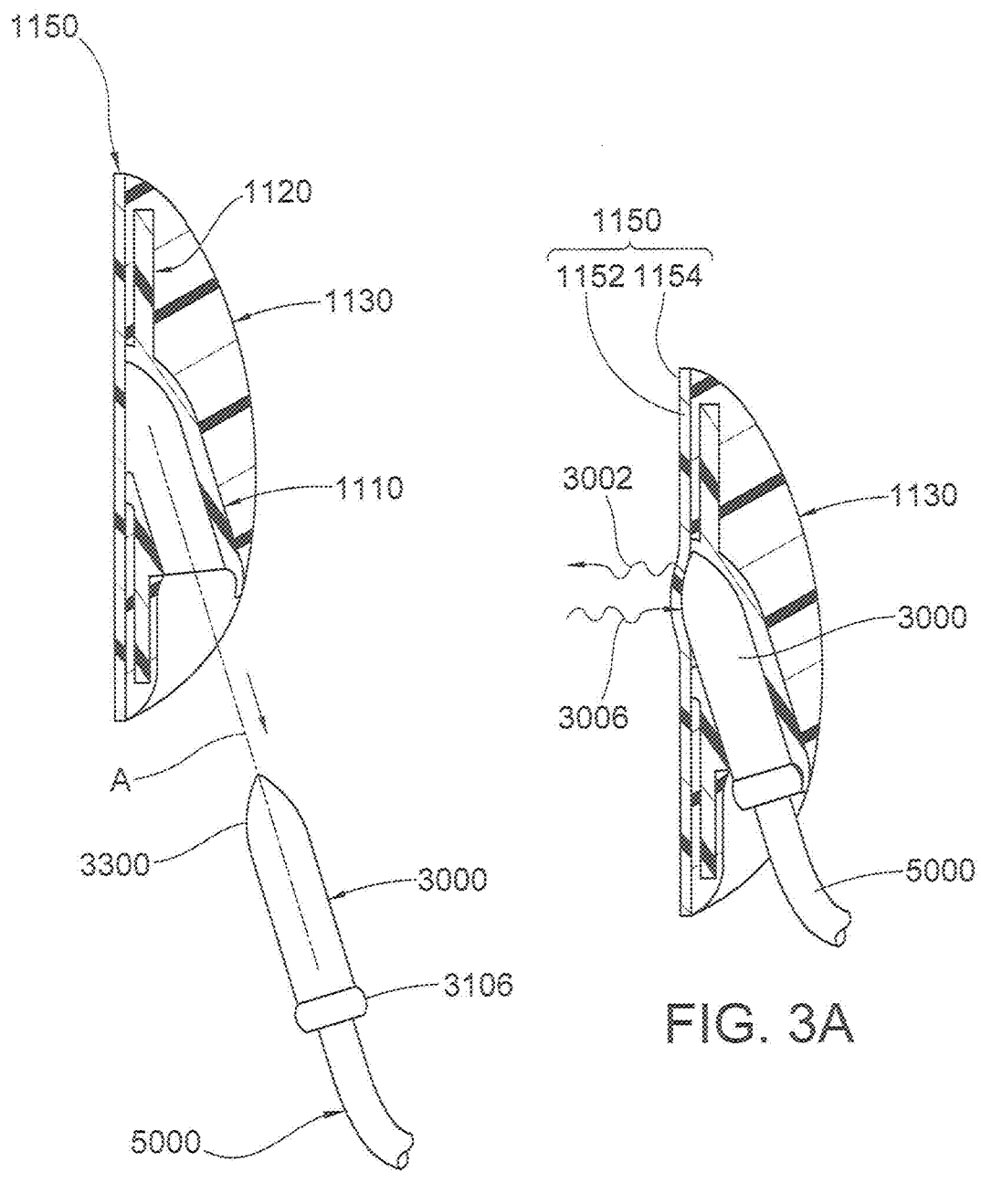

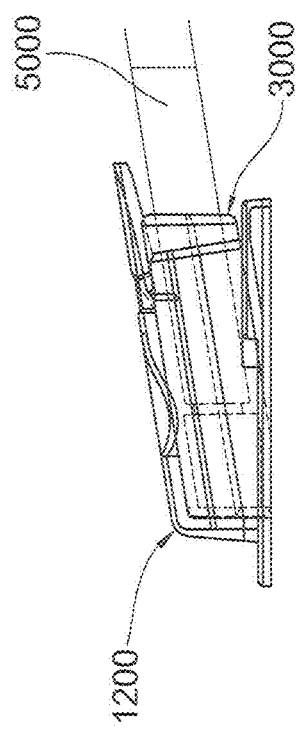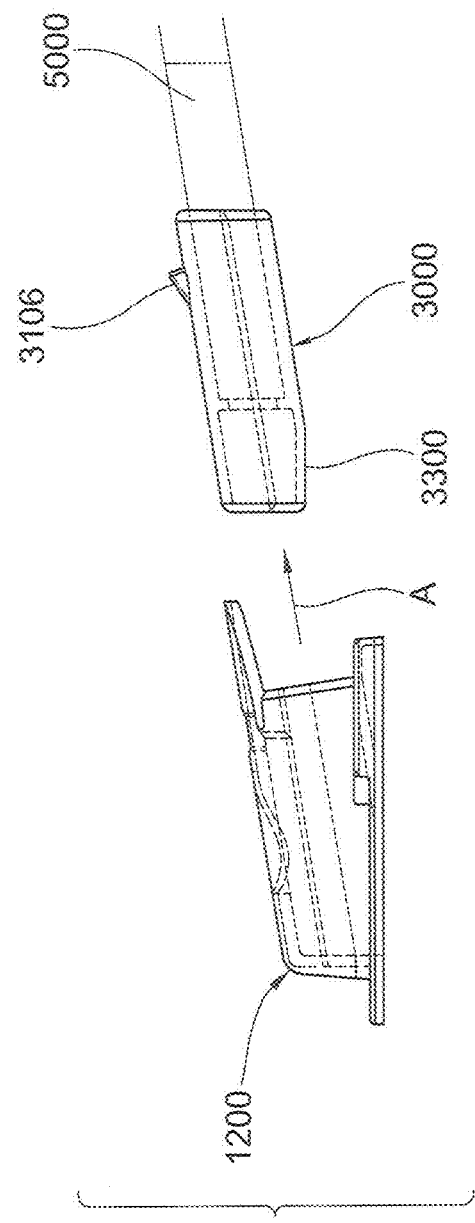

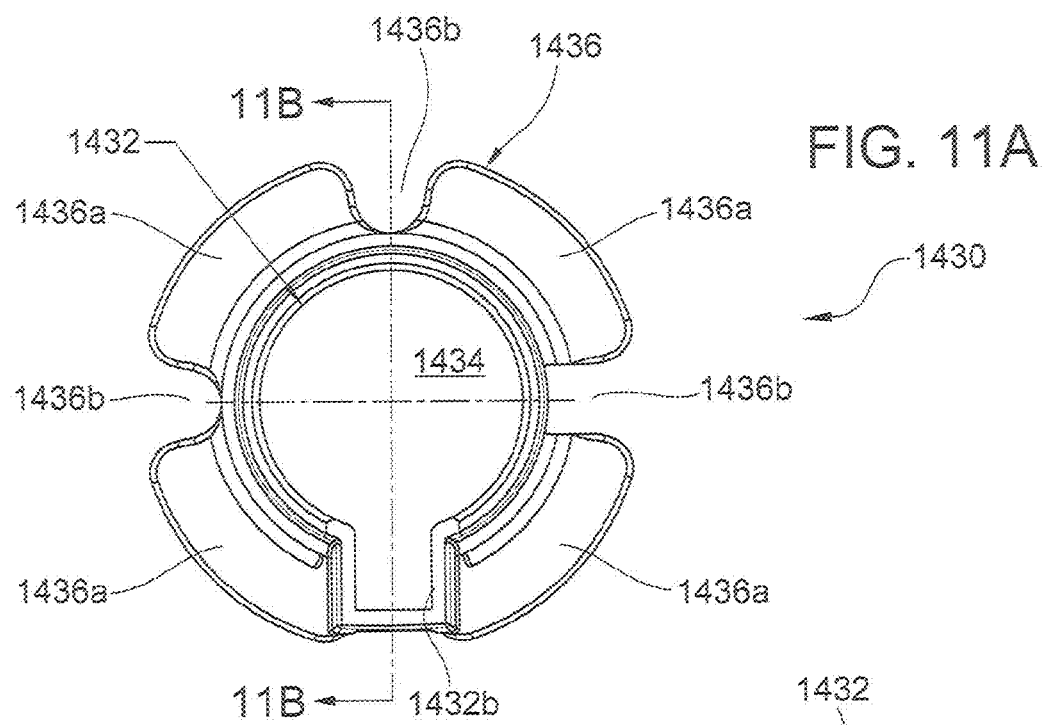
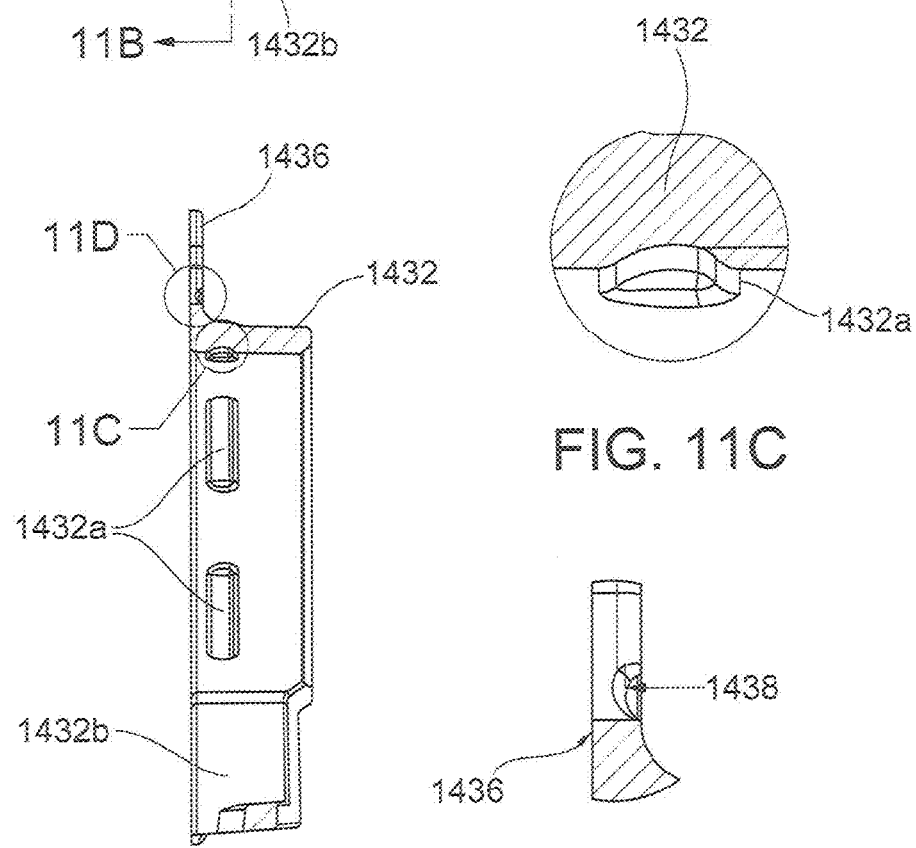
FIG. 11A
FIG. 11C
FIG. 11B
FIG. 11D

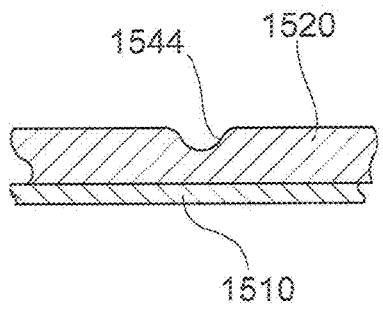
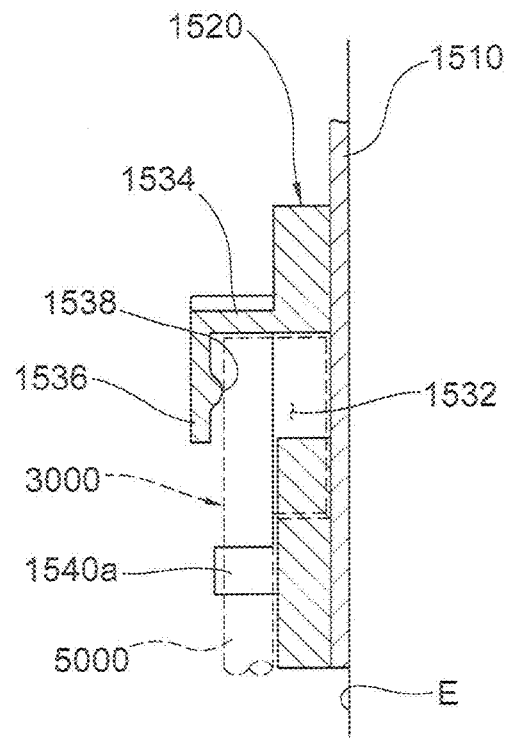
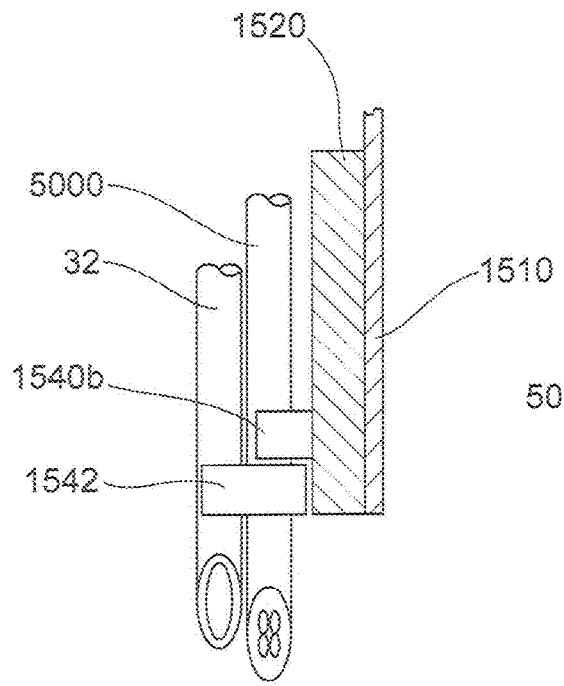
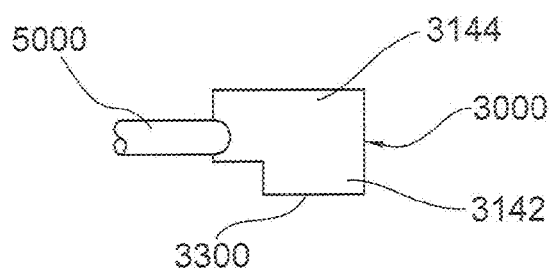
FIG. 13D
FIG. 13A
FIG. 13C
FIG. 13B

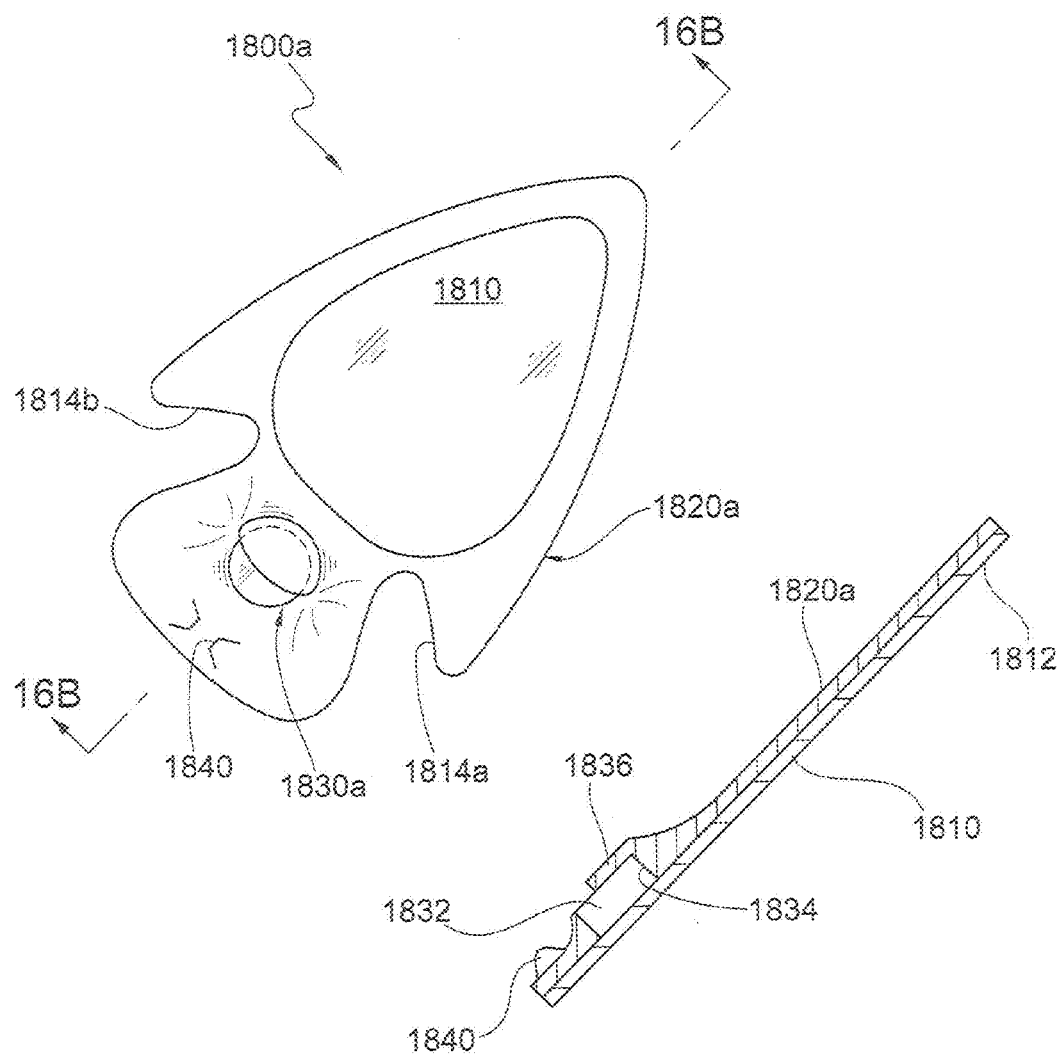

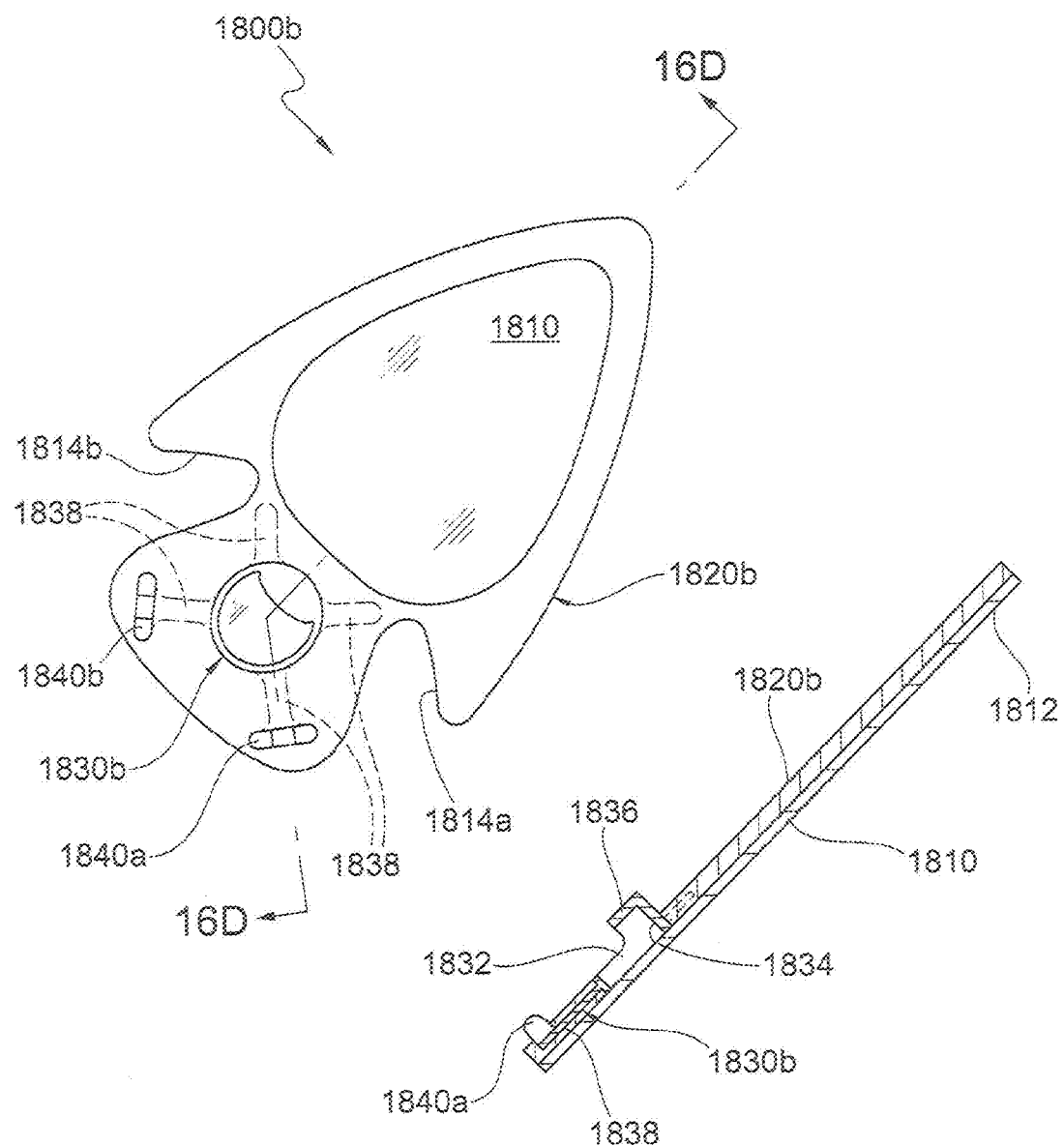

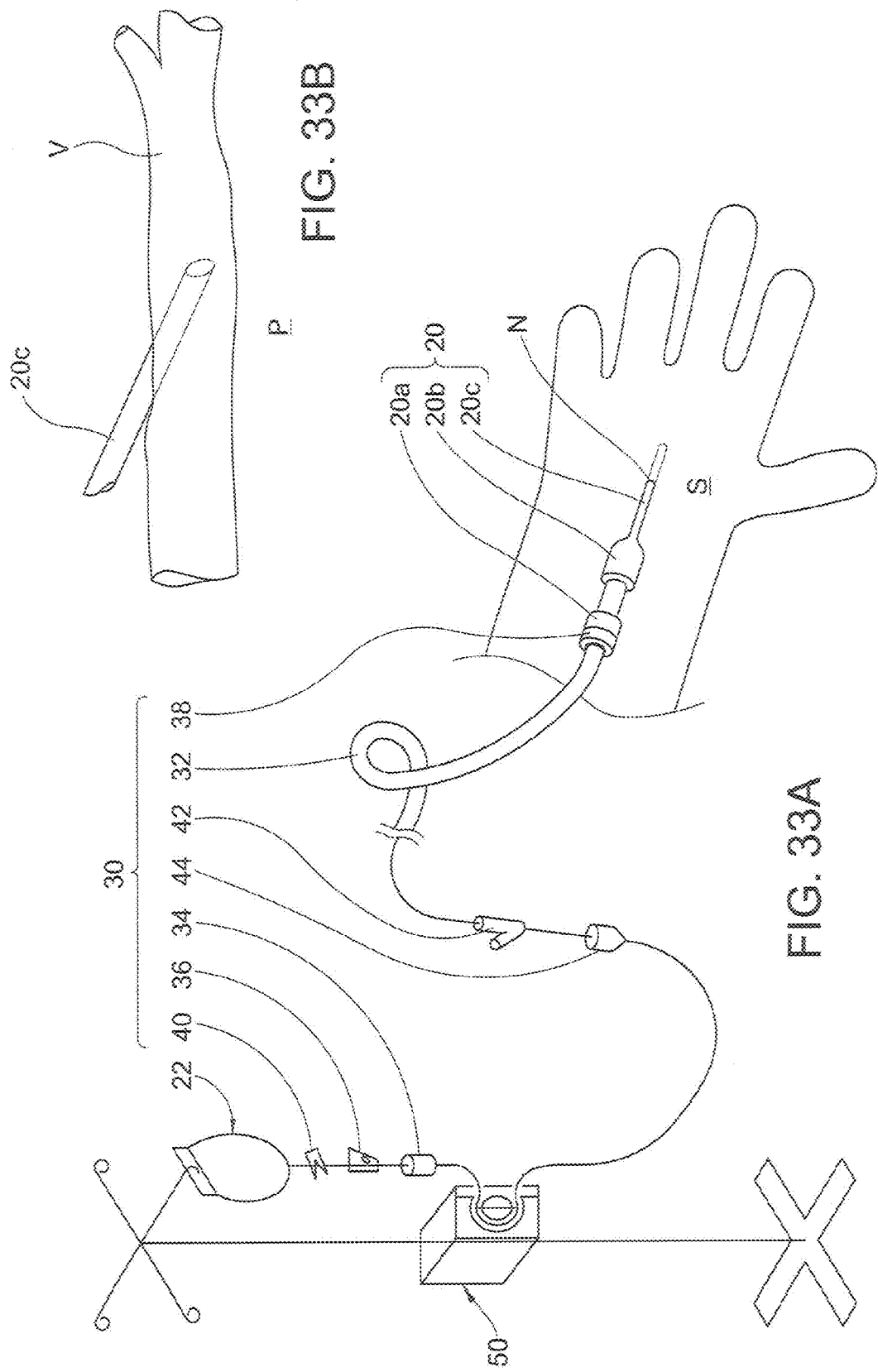

SYSTEM AND METHOD FOR MITIGATING THE EFFECTS OF TISSUE BLOOD VOLUME CHANGES TO AID IN DIAGNOSING INFILTRATION OR EXTRAVASATION IN ANIMALIA TISSUE

CROSS-REFERENCES TO RELATED APPLICATIONS

This application is a continuation-in-part of U.S. application Ser. No. 13/794,776, filed 11 Mar. 2013, which claims the priority of U.S. Provisional Application No. 61/609,865, filed 12 Mar. 2012. This application is also a continuation-in-part of U.S. application Ser. No. 13/792,193, filed 11 Mar. 2013, which claims the priority of U.S. Provisional Application No. 61/640,542, filed 30 Apr. 2012, and also claims the priority of U.S. Provisional Application No. 61/609,865, filed 12 Mar. 2012. This application is also a continuation-in-part of U.S. application Ser. Nos. 13/792,074 and 13/792,079, filed 10 Mar. 2013, both of which claim the priority of U.S. Provisional Application No. 61/706,726, filed 27 Sep. 2012, and also claim the priority of U.S. Provisional Application No. 61/609,865, filed 12 Mar. 2012. This application is also a continuation-in-part of U.S. application Ser. No. 13/792,051, filed 9 Mar. 2013, and of U.S. application Ser. No. 13/792,068, filed 10 Mar. 2013, both of which claim the priority of U.S. Provisional Application No. 61/755,273, filed 22 Jan. 2013, and also claim the priority of U.S. Provisional Application No. 61/609,865, filed 12 Mar. 2012. This application also claims the priority of U.S. Provisional Application No. 61/809,651, filed 8 Apr. 2013. Each of the aforementioned Applications and Provisional Applications are hereby incorporated by reference in their entirety.

STATEMENT REGARDING FEDERALLY SPONSORED RESEARCH OR DEVELOPMENT

Not Applicable

BACKGROUND OF THE INVENTION

FIGS. 33A and 33B show a typical arrangement for intravascular infusion. As the terminology is used herein, "intravascular" preferably refers to being situated in, occurring in, or being administered by entry into a blood vessel, thus "intravascular infusion" preferably refers to introducing a fluid or infusate into a subcutaneous blood vessel V. Intravascular infusion accordingly encompasses both intravenous infusion (administering a fluid into a vein) and intra-arterial infusion (administering a fluid into an artery).

A cannula 20 typically is used for administering fluid via the blood vessel V. Typically, cannula 20 is inserted through skin S at a cannulation site N and punctures the blood vessel V, for example, the cephalic vein, basilica vein, median cubital vein, or any suitable vein for an intravenous infusion. Similarly, any suitable artery may be used for an intra-arterial infusion.

Cannula 20 typically is in fluid communication with a fluid source 22. Typically, cannula 20 includes an extracorporeal connector 20a, a hub 20b, and a transcutaneous sleeve 20c. An extension tube may couple the extracorporeal connector 20a and the hub 20b, as shown in FIG. 33A, or the hub 20b may incorporate the extracorporeal connector 20a. Fluid source 22 typically includes one or more sterile containers that hold the fluid(s) to be administered. Examples of typical sterile containers include plastic bags, glass bottles or plastic bottles.

An administration set 30 typically provides a sterile conduit for fluid to flow from fluid source 22 to cannula 20. Typically, administration set 30 includes tubing 32, a drip chamber 34, a flow control device 36, and a cannula connector 38. Tubing 32 typically is made of polypropylene, nylon, or another flexible, strong and inert material. Drip chamber 34 typically permits the fluid to flow one drop at a time for reducing air bubbles in the flow. Tubing 32 and drip chamber 34 typically are transparent or translucent to provide a visual indication of the flow. Typically, flow control device 36 controls fluid flow in tubing 32 and is positioned upstream from drip chamber 34. Roller clamps and Dial-A-Flo®, manufactured by Hospira, Inc. (Lake Forest, Ill., US), are examples of typical flow control devices. Typically, cannula connector 38 and extracorporeal connector 20a provide a leak-proof coupling through which the fluid may flow. Luer-Lok™, manufactured by Becton, Dickinson and Company (Franklin Lakes, N.J., US), is an example of a typical leak-proof coupling.

Administration set 30 may also include at least one of a clamp 40, an injection port 42, a filter 44, or other devices. Typically, clamp 40 pinches tubing 32 to cut-off fluid flow. Injection port 42 typically provides an access port for administering medicine or another fluid via cannula 20. Filter 44 typically purifies and/or treats the fluid flowing through administration set 30. For example, filter 44 may strain contaminants from the fluid.

An infusion pump 50 may be coupled with administration set 30 for controlling the quantity or the rate of fluid flow to cannula 20. The Alaris® System manufactured by CareFusion Corporation (San Diego, Calif., US), BodyGuard® Infusion Pumps manufactured by CMA America, L.L.C. (Golden, Colo., US), and Flo-Gard® Volumetric Infusion Pumps manufactured by Baxter International Inc. (Deerfield, Ill., US) are examples of typical infusion pumps.

Intravenous infusion or therapy typically uses a fluid (e.g., infusate, whole blood, or blood product) to correct an electrolyte imbalance, to deliver a medication, or to elevate a fluid level. Typical infusates predominately consist of sterile water with electrolytes (e.g., sodium, potassium, or chloride), calories (e.g., dextrose or total parenteral nutrition), or medications (e.g., anti-infectives, anticonvulsants, antihyperuricemic agents, cardiovascular agents, central nervous system agents, chemotherapy drugs, coagulation modifiers, gastrointestinal agents, or respiratory agents). Examples of medications that are typically administered during intravenous therapy include acyclovir, allopurinol, amikacin, aminophylline, amiodarone, amphotericin B, ampicillin, carboplatin, cefazolin, cefotaxime, cefuroxime, ciprofloxacin, cisplatin, clindamycin, cyclophosphamide, diazepam, docetaxel, dopamine, doxorubicin, doxycycline, erythromycin, etoposide, fentanyl, fluorouracil, furosemide, ganciclovir, gemcitabine, gentamicin, heparin, imipenem, irinotecan, lorazepam, magnesium sulfate, meropenem, methotrexate, methylprednisolone, midazolam, morphine, nafcillin, ondansetron, paclitaxel, pentamidine, phenobarbital, phenytoin, piperacillin, promethazine, sodium bicarbonate, ticarcillin, tobramycin, topotecan, vancomycin, vinblastine and vincristine. Transfusions and other processes for donating and receiving whole blood or blood products (e.g., albumin and immunoglobulin) also typically use intravenous infusion.

Unintended infusing typically occurs when fluid from cannula 20 escapes from its intended vein/artery. Typically, unintended infusing causes an abnormal amount of the fluid to diffuse or accumulate in perivascular tissue P and may occur, for example, when (i) cannula 20 causes a vein/artery to rupture; (ii) cannula 20 improperly punctures the vein/artery;

(iii) cannula 20 backs out of the vein/artery; (iv) cannula 20 is improperly sized; (v) infusion pump 50 administers fluid at an excessive flow rate; or (vi) the infusate increases permeability of the vein/artery. As the terminology is used herein, "tissue" preferably refers to an association of cells, intercellular material and/or interstitial compartments, and "perivascular tissue" preferably refers to cells, intercellular material, interstitial fluid and/or interstitial compartments that are in the general vicinity of a blood vessel and may become unintentionally infused with fluid from cannula 20. Unintended infusing of a non-vesicant fluid is typically referred to as "infiltration," whereas unintended infusing of a vesicant fluid is typically referred to as "extravasation."

The symptoms of infiltration or extravasation typically include edema, pain or numbness in the vicinity of the cannulation site N; blanching, discoloration, inflammation or coolness of the skin S in the vicinity of the cannulation site N; breakdown, tautness or stretching of the skin S; or drainage from the cannulation site N. The consequences of infiltration or extravasation typically include skin reactions (e.g., blisters), nerve compression, compartment syndrome, or necrosis. Typical treatments for infiltration or extravasation include (i) applying warm or cold compresses; (ii) elevating the affected limb; (iii) administering hyaluronidase, phentolamine, sodium thiosulfate or dexrazoxane; (iv) fasciotomy; or (v) amputation.

BRIEF SUMMARY OF THE INVENTION

Embodiments according to the present invention include a system to aid in diagnosing at least one of infiltration and extravasation in Animalia tissue. The system includes a sensor, a dressing configured to couple the sensor to an epidermis of the Animalia tissue, a device, and a cable that couples the sensor and the device. The sensor includes a housing having a surface configured to confront the epidermis and first and second waveguides partially disposed in the housing. The first waveguide is configured to transmit first and second signals that enter the Animalia tissue through the epidermis. The first signal has a peak wavelength between approximately 800 nanometers and approximately 1,050 nanometers, and the second signal has a peak wavelength between approximately 570 nanometers and approximately 620 nanometers. The second waveguide is configured to transmit third and fourth signals that exit the Animalia tissue through the epidermis. The third signal includes a portion of the first signal that is at least one of reflected, scattered and redirected from the Animalia tissue, and the fourth signal includes a portion of the second signal that is at least one of reflected, scattered and redirected from the Animalia tissue. The device is configured to evaluate the third and fourth signals, and includes an optics bench, a processor coupled to the optics bench, and an indicator coupled to the processor. The optics bench includes a first light emitting diode, a second light emitting diode and a photodiode. The first light emitting diode is configured to emit the first signal transmitted by the first waveguide, the second light emitting diode is configured to emit the second signal transmitted by the first waveguide, and the photodiode is configured to detect the third and fourth signals transmitted by the second waveguide. The processor is configured to (i) compute normalized values of the third and fourth signals, (ii) compare the normalized value of the third signal with a threshold value, and (iii) compare the normalized values of the third and fourth signals. The indicator is configured to output a notice when (i) the normalized value of the third signal is less than the threshold value and (ii) the normalized value of the fourth signal is greater than the normalized value of the third signal. The cable includes portions of the first and second waveguides.

Other embodiments according to the present invention include a system to aid in diagnosing at least one of infiltration and extravasation in Animalia tissue. The system includes a sensor, a dressing configured to couple the sensor to an epidermis of the Animalia tissue, a device, and a cable that couples the sensor and the device. The sensor includes a housing having a surface configured to confront the epidermis and first and second waveguides partially disposed in the housing. The first waveguide is configured to transmit first and second signals that enter the Animalia tissue through the epidermis. The first signal has a peak wavelength between approximately 800 nanometers and approximately 1,050 nanometers, and the second signal has a peak wavelength between approximately 570 nanometers and approximately 620 nanometers. The second waveguide is configured to transmit third and fourth signals that exit the Animalia tissue through the epidermis. The third signal includes a portion of the first signal that is at least one of reflected, scattered and redirected from the Animalia tissue, and the fourth signal includes a portion of the second signal that is at least one of reflected, scattered and redirected from the Animalia tissue. The device is configured to evaluate the third and fourth signals, and includes an optics bench, a processor coupled to the optics bench, and an indicator coupled to the processor. The optics bench includes a first light emitting diode, a second light emitting diode and a photodiode. The first light emitting diode is configured to emit the first signal transmitted by the first waveguide, the second light emitting diode is configured to emit the second signal transmitted by the first waveguide, and the photodiode is configured to detect the third and fourth signals transmitted by the second waveguide. The processor is configured to (i) activate and deactivate the first and second light emitting diodes during each of a plurality of cycles, (ii) sample the third and fourth signals during each of the plurality of cycles, (iii) compute normalized values of individual third and fourth signal samples for each of the plurality of cycles, (iv) fit an equation to ordered pairs of the normalized values for each cycle in a first collection of the plurality of cycles, and (v) compare the equation to ordered pairs of the normalized values for each cycle in a second collection of the plurality of cycles. The indicator is configured to output a notice when (i) the ordered pairs of the second collection number more than a first threshold value, (ii) the ordered pairs of the second collection are perpendicularly spaced a displacement from the equation, (iii) the displacement corresponds to a change in the normalized values of the third signal samples that is greater than a second threshold value, and (iv) the displacement corresponds to a change in the normalized values of the fourth signal samples that is less than the change in the normalized values of the third signal samples. The cable includes portions of the first and second waveguides.

Other embodiments according to the present invention include a system to aid in diagnosing at least one of infiltration and extravasation in Animalia tissue. The system includes a sensor, a dressing configured to couple the sensor to an epidermis of the Animalia tissue, a device, and a cable that couples the sensor and the device. The sensor includes a housing having a surface configured to confront the epidermis and first and second waveguides partially disposed in the housing. The first waveguide is configured to transmit first and second signals that enter the Animalia tissue through the epidermis. The first signal has a peak wavelength between approximately 800 nanometers and approximately 1,050 nanometers, and the second signal has a peak wavelength between approximately 570 nanometers and approximately 620 nanometers. The second waveguide is configured to transmit third and fourth signals that exit the Animalia tissue through the epidermis. The third signal includes a portion of the first signal that is at least one of reflected, scattered and redirected from the Animalia tissue, and the fourth signal includes a portion of the second signal that is at least one of reflected, scattered and redirected from the Animalia tissue. The device is configured to evaluate the third and fourth signals, and includes an optics bench, a processor coupled to the optics bench, and an indicator coupled to the processor. The optics bench includes a first light emitting diode, a second light emitting diode and a photodiode. The first light emitting diode is configured to emit the first signal transmitted by the first waveguide, the second light emitting diode is configured to emit the second signal transmitted by the first waveguide, and the photodiode is configured to detect the third and fourth signals transmitted by the second waveguide. The processor is configured to (i) compute normalized values of the third and fourth signals, (ii) compute a predicted signal based on the normalized values of the fourth signal, and (iii) compare the predicted signal and the normalized values of the third signal. The indicator is configured to output a notice when (i) the predicted signal is less than a first threshold value and (ii) the predicted signal and the normalized values of the third signal diverge less than a second threshold value. The cable includes portions of the first and second waveguides.

Other embodiments according to the present invention include a system to aid in diagnosing at least one of infiltration and extravasation in Animalia tissue. The system includes a sensor configured to emit first and second signals entering the Animalia tissue and to detect third and fourth signals exiting the Animalia tissue, and a device coupled to the sensor and configured to output a notice based on the third and fourth signals. The first signal has a peak wavelength between approximately 800 nanometers and approximately 1,050 nanometers, and the second signal has a peak wavelength between approximately 560 nanometers and approximately 660 nanometers. The third signal includes a portion of the first signal that is at least one of reflected, scattered and redirected from the Animalia tissue, and the fourth signal includes a portion of the second signal that is at least one of reflected, scattered and redirected from the Animalia tissue. The third signal is configured to detect infusate accumulation over time in the Animalia tissue, and the fourth signal is configured to detect tissue blood volume changes in the Animalia tissue.

Other embodiments according to the present invention include a system including a sensor and a device coupled to the sensor. The sensor is configured to detect infusate accumulation in Animalia tissue and to detect tissue blood volume change in the Animalia tissue. The device is configured to aid in diagnosing at least one of infiltration and extravasation in the Animalia tissue based on evaluating infusate accumulation detected by the sensor and on evaluating tissue blood volume change detected by the sensor.

Other embodiments according to the present invention include a system including a sensor and a device coupled to the sensor. The sensor is configured to detect in Animalia tissue (i) a first electromagnetic radiation extinction that is dominated by absorption of a first wavelength and (ii) a second electromagnetic radiation extinction that is dominated by scattering of a second wavelength. The device is configured to aid in diagnosing at least one of infiltration and extravasation in the Animalia tissue based on evaluating the first and second electromagnetic radiation extinctions detected by the sensor.

Other embodiments according to the present invention include a method to aid in diagnosing at least one of infiltration and extravasation in the Animalia tissue. The method includes detecting infusate accumulation in the Animalia tissue, detecting tissue blood volume change in the Animalia tissue, evaluating whether infusate is accumulating in the Animalia tissue, and evaluating whether tissue blood volume is changing in the Animalia tissue.

Other embodiments according to the present invention include a method to aid in diagnosing at least one of infiltration and extravasation in the Animalia tissue. The method includes (i) detecting extinction of a first electromagnetic radiation signal in the Animalia tissue, the extinction is dominated by scattering of the first electromagnetic radiation signal, (ii) detecting extinction of a second electromagnetic radiation signal in the Animalia tissue, the extinction is dominated by absorption of the second electromagnetic radiation signal; and (iii) evaluating the extinctions of the first and second electromagnetic radiation signals in the Animalia tissue.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features, principles, and methods of the invention.

FIG. 1 illustrates a system according to the present disclosure for aiding in diagnosing at least one of infiltration and extravasation in Animalia tissue.

FIG. 2A is a plan view illustrating an embodiment of an epidermal appliance according to the present disclosure. Portions of a fitting and a frame are shown in dashed line.

FIG. 2B is a bottom view of the appliance shown in FIG. 2A.

FIG. 2C is a cross-section view taken along line IIC-IIC in FIG. 2A.

FIG. 3A is a partial cross-section view illustrating a second arrangement of the appliance shown in FIG. 2A releasing an electromagnetic radiation sensor.

FIG. 3B is a partial cross-section view illustrating a first arrangement of the appliance shown in FIG. 2A retaining an electromagnetic radiation sensor.

FIG. 6A is a cross-section view illustrating a first arrangement of the appliance shown in FIG. 4 retaining an electromagnetic radiation sensor.

FIG. 6B is a cross-section view illustrating a second arrangement of the appliance shown in FIG. 4 releasing an electromagnetic radiation sensor.

FIGS. 11A-11D illustrate a fitting of the dressing assembly shown in FIG. 9. FIG. 11A is a plan view, FIG. 11B is a cross-section view taken along line XIB-XIB in FIG. 11A, FIG. 11C is an enlarged view illustrating detail XIC in FIG. 11B, and FIG. 11D is an enlarged view illustrating detail XID in FIG. 11B.

FIGS. 13A-13D are schematic views illustrating details of the dressing shown in FIG. 12. FIG. 13A is a cross-section view taken along line XIIIA-XIIIA in FIG. 12 with the electromagnetic radiation sensor shown in dash-dot line, FIG. 13B is a detail view showing features of the electromagnetic radiation sensor in FIG. 13A, FIG. 13C is a cross-section view taken along line XIIIC-XIIIC in FIG. 12, and FIG. 13D is a cross-section view taken along line XIIID-XIIID in FIG. 12.

FIG. 15A is a plan view showing the dressing assembly including a frame, FIG. 15B is a plan view showing the barrier film of FIG. 15A with a framework, FIG. 15C is a plan view of the frame in FIG. 15A including a lead management system, and FIG. 15D is a plan view showing an implementation of the dressing assembly including the frame and the lead management system. An electromagnetic radiation sensor, a portion of a sensor cable, a cannula and a portion of an administration set are also shown in FIG. 15D.

FIGS. 16A-16D illustrate embodiments according to the present disclosure of dressing assemblies including an appliance integrated with a barrier film. FIG. 16A is a plan view illustrating a dressing assembly including the appliance integrally molded with a frame, FIG. 16B is a cross-section view taken along line XVIB-XVIB in FIG. 16A, FIG. 16C is a plan view illustrating a dressing assembly including the appliance over-molded with a frame, and FIG. 16D is a cross-section view taken along line XVID-XVID in FIG. 16C.

FIG. 33A is a schematic view illustrating a typical set-up for infusion administration.

FIG. 33B is a schematic view illustrating a subcutaneous detail of the set-up shown in FIG. 33A.

In the figures, the thickness and configuration of components may be exaggerated for clarity. The same reference numerals in different figures represent the same component.

DETAILED DESCRIPTION OF THE INVENTION

Figure 4:
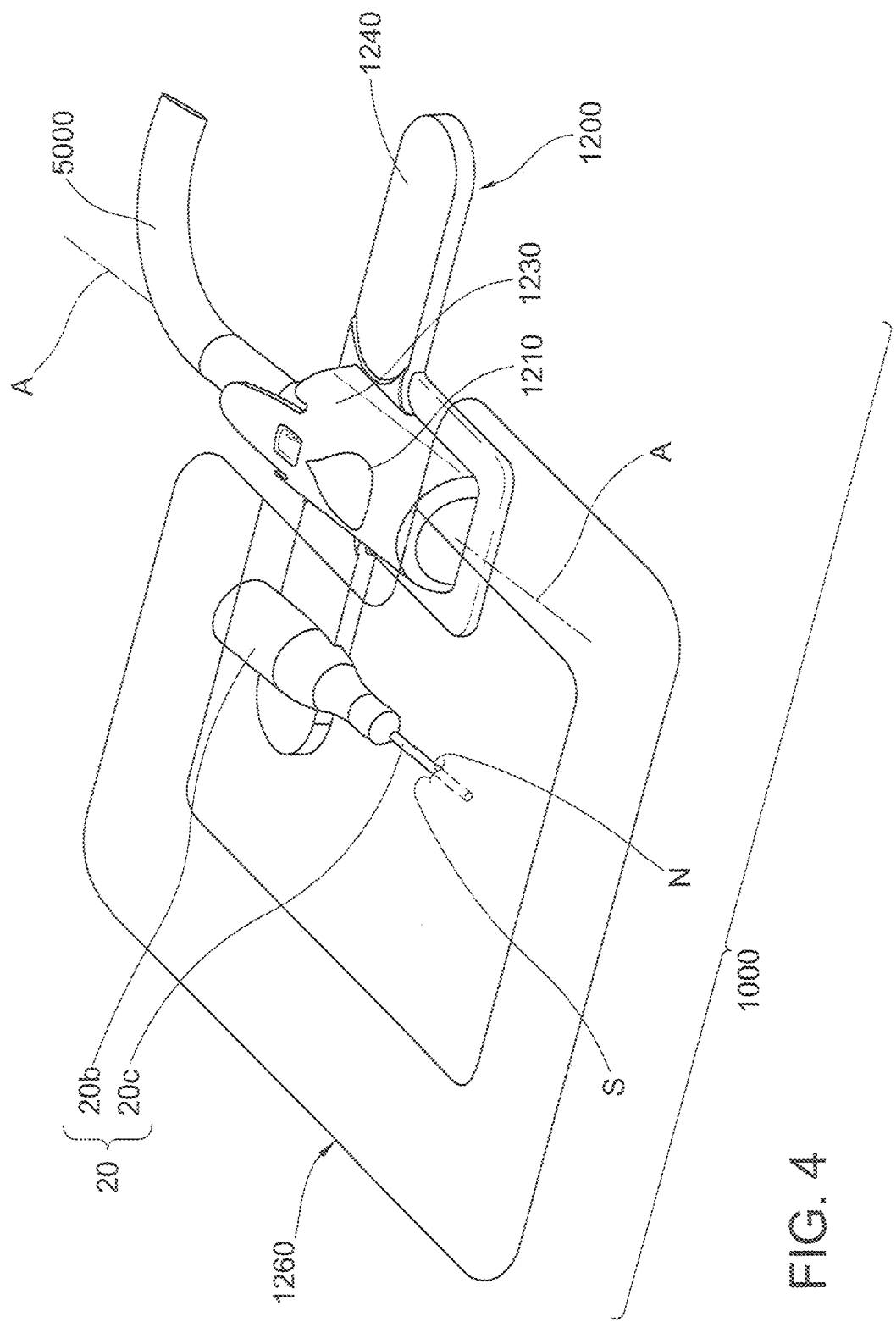
FIG. 4 is a partially exploded perspective view illustrating a dressing assembly including an embodiment of an appliance according to the present disclosure, an electromagnetic radiation sensor, a cannula, and a barrier film.

The following description and drawings are illustrative and are not to be construed as limiting. Numerous specific details are described to provide a thorough understanding of the disclosure. However, in certain instances, well-known or conventional details are not described in order to avoid obscuring the description.

Reference in this specification to "one embodiment" or "an embodiment" means that a particular feature, structure, or characteristic described in connection with the embodiment is included in at least one embodiment according to the disclosure. The appearances of the phrases "one embodiment" or "other embodiments" in various places in the specification are not necessarily all referring to the same embodiment, nor are separate or alternative embodiments mutually exclusive of other embodiments. Moreover, various features are described that may be exhibited by some embodiments and not by others. Similarly, various features are described that may be included in some embodiments but not other embodiments.

The terms used in this specification generally have their ordinary meanings in the art, within the context of the disclosure, and in the specific context where each term is used. Certain terms in this specification may be used to provide additional guidance regarding the description of the disclosure. It will be appreciated that a feature may be described more than one-way.

Alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term.

System Overview

FIG. 1 shows a system 100 to preferably aid in diagnosing at least one of infiltration and extravasation in Animalia tissue. Preferably, system 100 includes a dressing 1000, an electromagnetic radiation sensor 3000, a sensor cable 5000, and a patient monitoring device 6000.

Dressing

Dressing 1000 preferably includes an epidermal appliance coupling electromagnetic radiation sensor 3000 with the skin S. Preferably, dressing 1000 locates electromagnetic radiation sensor 3000 to overlie a target area of the skin S. As the terminology is used herein, "target area" preferably refers to a portion of a patient's skin that is generally proximal to where an infusate is being administered and frequently proximal to the cannulation site N. Preferably, the target area overlies the perivascular tissue P. According to one embodiment, dressing 1000 preferably uses adhesion to couple electromagnetic radiation sensor 3000 with respect to an epidermis E of the skin S. According to other embodiments, any suitable coupling may be used that preferably minimizes relative movement between electromagnetic radiation sensor 3000 and the skin S. Preferably, dressing 1000 and the skin S have generally similar viscoelastic characteristics such that both respond in a generally similar manner to stress and strain.

Dressing 1000 preferably includes different arrangements that permit electromagnetic radiation sensor 3000 to be coupled, decoupled and recoupled, e.g., facilitating multiple independent uses with one or a plurality of dressings 1000. As the terminology is used herein, "arrangement" preferably refers to a relative configuration, formation, layout or disposition of dressing 1000 and electromagnetic radiation sensor 3000. Preferably, dressing 1000 includes a first arrangement that retains electromagnetic radiation sensor 3000 relative to the skin S for monitoring infiltration or extravasation during an infusion with cannula 20. A second arrangement of dressing 1000 preferably releases electromagnetic radiation sensor 3000 from the first arrangement. Accordingly, electromagnetic radiation sensor 3000 may be decoupled from a singular dressing 1000 in the second arrangement, e.g., during patient testing or relocation, and subsequently recoupled in the first arrangement of the singular dressing 1000 such that a relationship between electromagnetic radiation sensor 3000 and the skin S is generally repeatable. Electromagnetic radiation sensor 3000 may also be coupled to a first dressing 1000 in the first arrangement, decoupled from the first dressing 1000 in the second arrangement, and subsequently coupled to a second dressing 1000 in the first arrangement.

A first embodiment of dressing 1000 is shown in FIGS. 2A-3B. An appliance 1100 includes (i) a fitting 1110 for receiving electromagnetic radiation sensor 3000, which senses if fluid is infusing the perivascular tissue P around transcutaneous sleeve 20c; (ii) a frame 1120 for distributing to the skin S forces acting on appliance 1100; and (iii) a body 1130 for covering fitting 1110 and frame 1120 with a soft haptic surface. Appliance 1100 preferably couples electromagnetic radiation sensor 3000 with the skin S proximate the cannulation site N. According to one embodiment, appliance 1100 positions electromagnetic radiation sensor 3000 relative to skin S within approximately 10 centimeters of the cannulation site N and preferably in a range of approximately one centimeter to approximately five centimeters away from the cannulation site N. According to other embodiments, appliance 1100 positions electromagnetic radiation sensor 3000 relative to skin S so as to generally overlie an infusate outlet of transcutaneous sleeve 20c.

Electromagnetic radiation sensor 3000 may be coupled to the skin S separately from typical contamination barriers. An example of a contamination barrier 1260 is shown in FIG. 4. Typical contamination barriers may (i) protect the cannulation site N; and (ii) allow the epidermis E to be observed around the cannulation site N. Preferably, appliance 1100 and a contamination barrier are coupled to the epidermis E separately, e.g., at different times or in different steps of a multiple step process. According to one embodiment, a contamination barrier that overlies the cannulation site N may also overlie portions of the cannula 20 and/or appliance 1100. According to other embodiments, a contamination barrier may overlie the cannulation site N and be spaced from appliance 1100.

Fitting 1110 preferably provides two arrangements with respect to electromagnetic radiation sensor 3000. Referring to FIG. 3A, a first arrangement of fitting 1110 preferably retains electromagnetic radiation sensor 3000 relative to appliance 1100 for monitoring infiltration or extravasation during an infusion with cannula 20. Referring to FIG. 3B, a second arrangement of fitting 1110 preferably releases electromagnetic radiation sensor 3000 from the first arrangement. Accordingly, electromagnetic radiation sensor 3000 may be decoupled from appliance 1100 in the second arrangement of fitting 1110, e.g., during patient testing or relocation, and subsequently recoupled in the first arrangement of fitting 1110 such that a positional relationship between electromagnetic radiation sensor 3000, the skin S and the perivascular tissue P is generally repeatable.

Relative movement between electromagnetic radiation sensor 3000 and appliance 1100 preferably is limited between the first and second arrangements. Preferably, fitting 1110 includes a chute 1112 that extends along an axis A between a first end 1114 and a second end 1116. According to one embodiment, chute 1112 preferably is centered about axis A, which preferably is obliquely oriented relative to the epidermis E. Chute 1112 and electromagnetic radiation sensor 3000 preferably are cooperatively sized and shaped so that (i) electromagnetic radiation sensor 3000 can be inserted in first end 1114 in only one relative orientation; and (ii) relative movement between the first and second arrangements is constrained to substantially only translation along axis A. As the terminology is used herein, "translation" refers to movement without rotation or angular displacement. Electromagnetic radiation sensor 3000 preferably does not rub the epidermis E during translation along axis A. Accordingly, forces that may tend to distort the skin S preferably are prevented or at least minimized while moving electromagnetic radiation sensor 3000 between the first and second arrangements of fitting 1110. It is believed that reducing distortion of the skin S reduces distortion of subcutaneous tissue including the perivascular tissue P and the blood vessel V, and therefore also reduces the likelihood of displacing cannula 20 while moving electromagnetic radiation sensor 3000 between the first and second arrangements of fitting 1110.

Appliance 1100 preferably includes a latch 1118 for retaining electromagnetic radiation sensor 3000 in the first arrangement of fitting 1110. Preferably, latch 1118 is resiliently biased into engagement with a cooperating feature on electromagnetic radiation sensor 3000 in the first arrangement. According to one embodiment, latch 1118 preferably includes a cantilever 1118a that has a recess or aperture 1118b for cooperatively receiving a projection 3106 of electromagnetic radiation sensor 3000 in the first arrangement. In the second arrangement, latch 1118 may be manipulated to alter the nominal form of cantilever 1118a for releasing projection 3106 from recess or aperture 1118a so that electromagnetic radiation sensor 3000 may be withdrawn from chute 1112 though first end 1114. Preferably, latch 1118 provides a positive indication, e.g., a tactile or audible notification, that electromagnetic radiation sensor 3000 is in at least one of the first and second arrangements. According to other embodiments, latch 1118 may include snaps, a cap, or another suitable device that, in the first arrangement, retains electromagnetic radiation sensor 3000 in fitting 1110 and, in the second arrangement, releases electromagnetic radiation sensor 3000 from fitting 1110, e.g., allowing electromagnetic radiation sensor 3000 to separate from appliance 1100.

Fitting 1110 preferably permits multiple uses of electromagnetic radiation sensor 3000. The first and second arrangements of fitting 1110 preferably permit electromagnetic radiation sensor 3000 to be decoupled and recoupled with appliance 1100, or decoupled from a first patient's appliance 1100 and coupled to a second patient's appliance 1100. Thus, fitting 1110 preferably permits reusing electromagnetic radiation sensor 11000 with a plurality of appliances 1100 that are individually coupled to patients' epidermises.

Appliance 1100 also preferably maintains electromagnetic radiation sensor 3000 in a substantially consistent location relative to the perivascular tissue P. Preferably, chute 1112 constrains movement of electromagnetic radiation sensor 3000 such that a superficies 3300 of electromagnetic radiation sensor 3000 is disposed proximate second end 1116 of fitting 1110 in the first arrangement. Electromagnetic radiation sensor 3000 preferably emits electromagnetic radiation 3002 from superficies 3300 and collects electromagnetic radiation 3006 that impinges on superficies. According to one embodiment, electromagnetic radiation sensor 3000 projects from appliance 1100 such that superficies 3300 preferably is disposed beyond second end 1116 toward the epidermis E for substantially eliminating or at least minimizing a gap between superficies 3300 and the epidermis E. Thus, appliance 1100 in the first arrangement of fitting 1110 preferably maintains a substantially consistent relative position between superficies 3300 and the skin S for sensing over time if fluid from cannula 20 is infusing the perivascular tissue P.

Appliance 1100 preferably resists forces that tend to change the position of electromagnetic radiation sensor 3000 relative to the perivascular tissue P. Pulling or snagging sensor cable 5000 is one example of the forces that frame 1120 distributes over a larger area of the skin S than the areas overlaid by superficies 3300 or by fitting 1110. Frame 1120 therefore preferably enhances maintaining a substantially consistent relative position between superficies 3300 and the skin S for sensing over time if fluid from cannula 20 is infusing the perivascular tissue P.

Appliance 1100 preferably includes a relatively rigid skeleton and a relatively supple covering. Preferably, the skeleton includes fitting 1110 for interacting with electromagnetic radiation sensor 3000 and frame 1120 for distributing to the skin S forces acting on fitting 1110. Frame 1120 preferably includes a hoop 1122 coupled with fitting 1110 by at least one arm (four arms 1124a-1124d are indicated in FIG. 2A). According to one embodiment, hoop 1122 preferably includes an uninterrupted annulus disposed about fitting 1110. According to other embodiments, hoop 1122 preferably includes a plurality of segments disposed about fitting 1110.

The composition and dimensions of the skeleton preferably are selected so that forces acting on appliance 1100 are distributed to the skin S. According to one embodiment, fitting 1110 and frame 1120 preferably are formed as a single independent component, e.g., integrally molded with a substantially homogeneous chemical compound. According to another embodiment, fitting 1110 and frame 1120 may be composed of more than one compound and/or may include an assembly of a plurality of pieces. Appliance 1100 may be subjected to a variety of forces, for example, due to pulling or snagging sensor cable 5000, and preferably the dimensions of hoop 1122 and arms 1124a-1124d are selected for reacting to these forces. According to one embodiment, the dimensions of frame 1120 preferably include arm 1124a being relatively more robust than arms 1124b-1124d, arms 1124c and 1124d being relatively the least robust, and arm 1124b being relatively less robust than arm 1124a and relatively more robust than arms 1124c and 1124d. Thus, according to this embodiment, appliance 1100 reacts to forces, e.g., an approximately eight-pound force pulling sensor cable 5000 away from the skin S, that may tend to move electromagnetic radiation sensor 3000 by (i) distributing a compression force to a first area of the skin S proximate arm 1124a; and (ii) distributing a tension force to a second area of the skin S proximate arm 1124b. The first and second areas preferably are larger than a third area of the skin S that the superficies 3300 and/or fitting 1110 overlie. Similarly, arms 1124c and 1124d preferably distribute compression and tension forces to fourth and fifth areas of the epidermis in response to, e.g., torsion forces acting on sensor cable 5000. Appliance 1100 therefore preferably resists changes to the relative position between superficies 3300 and the skin S by distributing over relatively large areas of the skin S the forces that may tend to move electromagnetic radiation sensor 3000 in the first arrangement of fitting 1110.

The relatively supple covering of appliance 1100 preferably includes a body 1130 that presents a soft haptic exterior surface overlying the skeleton. Preferably, body 1130 has a relatively lower hardness as compared to fitting 1110 and frame 1120. According to one embodiment, body 1130 preferably consists of a first homogeneous chemical compound, fitting 1110 and frame 1120 preferably consist of a second homogeneous chemical compound, and the first homogeneous chemical compound has a lower hardness than the second homogeneous chemical compound. The first homogeneous chemical compound preferably includes silicone or another material having a relatively low durometer, e.g., approximately Shore A 10 to approximately Shore A 60, and the second homogeneous chemical compound preferably includes polyurethane or another material having a relatively higher durometer, e.g., approximately Shore D 30 to approximately Shore D 70. Accordingly, the skeleton including fitting 1110 and frame 1120 preferably provides a structure for distributing forces applied to appliance 1100, and body 1130 provides a soft haptic exterior surface that imparts to appliance 1100 a desirable tactile feel, which may be characterized as soft rather than hard to the touch. Body 1130 includes a face 1132 preferably confronting the epidermis E.

A process for manufacturing appliance 1100 preferably includes covering the skeleton with the soft haptic exterior surface. According to one embodiment, appliance 1100 is molded in a multiple step process. Preferably, one step includes molding fitting 1110 and frame 1120 in a mold, another step includes adjusting the mold, and yet another step includes molding body 1130 over fitting 1110 and frame 1120 in the adjusted mold. An apparatus for molding fitting 1110, frame 1120 and body 1130 preferably includes a common mold portion, a first mold portion cooperating with the common mold portion for molding fitting 1110 and frame 1120, and a second mold portion cooperating with the common mold portion for over-molding body 1130. Preferably, the common and first mold portions receive a first shot of material to mold fitting 1110 and frame 1120, the mold is adjusted by decoupling the first mold portion from the common mold portion and coupling the second mold portion with the common mold portion, and the common and second mold portions receive a second shot of material to mold body 1130. Fitting 1110 and frame 1120 preferably remain in the common mold portion while decoupling the first mold portion and coupling the second mold portion. Accordingly, appliance 1100 is preferably molded in a two-shot process with a skeleton including fitting 1110 and frame 1120 being subsequently covered with a soft haptic exterior surface including body 1130. According to another embodiment, the skeleton may consist solely of fitting 1110, which may exclusively be molded in the first shot of a two-shot process.

Appliance 1100 may be wholly biocompatible and/or include a biocompatible layer for contacting the epidermis E. As the terminology is used herein, "biocompatible" preferably refers to compliance with Standard 10993 promulgated by the International Organization for Standardization (ISO 10993) and/or Class VI promulgated by The United States Pharmacopeial Convention (USP Class VI). Other regulatory entities, e.g., National Institute of Standards and Technology, may also promulgate standards that may additionally or alternatively be applicable regarding biocompatibility.

Referring particularly to FIGS. 2C and 3A, a foundation 1150 preferably (1) couples appliance 1100 and the epidermis E; and (2) separates the rest of appliance 1100 from the epidermis E. Preferably, foundation 1150 includes a panel 1152 that is coupled to face 1132 confronting the epidermis E. According to one embodiment, panel 1152 preferably is adhered to face 1132. Panel 1152 preferably includes polyurethane and occludes second end 1116 for providing a barrier between the epidermis E and superficies 3300 in the second arrangement. Preferably, panel 1152 is biocompatible according to ISO 10993 and/or USP Class VI.

Foundation 1150 preferably includes an adhesive coating 1154 for adhering appliance 1100 to the epidermis E. Adhesive 1154 preferably includes a silicone adhesive, an acrylic adhesive or another medical grade adhesive that is biocompatible according to ISO 10993 and/or USP Class VI. According to one embodiment, adhesive 1154 may be applied to all or a portion of panel 1152 on the surface that confronts the epidermis E. According to other embodiments, panel 1152 may be omitted and adhesive 1154 may directly adhere body 1130 and/or fitting 1110 to the epidermis E.

Adhesive 1154 preferably may be adjusted to vary the bond strength between appliance 1100 and the epidermis E. Preferably, stronger or more adhesive 1154 may be used for coupling appliance 1100 to relatively robust skin, e.g., adult skin, and weaker or less adhesive 1154 may be used for coupling appliance 1100 to relatively delicate skin, e.g., pediatric skin.

Preferably, appliance 1100 permits viewing the epidermis E with visible light and generally rejects interference by ambient sources with emitted and collected electromagnetic radiation 3002 and 3006. As the terminology is used herein, "visible light" refers to energy in the visible portion of the electromagnetic spectrum, for example, wavelengths between approximately 380 nanometers and approximately 760 nanometers. These wavelengths generally correspond to a frequency range of approximately 400 terahertz to approximately 790 terahertz. Preferably, body 1130 is transparent or translucent to visible light for viewing the epidermis E that underlies at least a portion of appliance 1100. According to one embodiment, fitting 1110 and frame 1120 preferably are also transparent or translucent to visible light. According to other embodiments, fitting 1110 and/or frame 1120 may be generally opaque to visible light. According to still other embodiments, body 1130 may be generally opaque to visible light or fitting 1110 and/or frame 1120 may be may be transparent or translucent to visible light. Preferably, fitting 1110, frame 1120 and body 1130, but not foundation 1150, absorb or block electromagnetic radiation with wavelengths that approximately correspond to emitted and collected electromagnetic radiation 3002 and 3006, e.g., radiation in the near-infrared portion of the electromagnetic spectrum. Accordingly, appliance 1100 preferably permits visible light viewing of the epidermis E and minimizes ambient source interference with emitted and collected electromagnetic radiation 3002 and 3006.

Appliance 1100 preferably is advantageous at least because (i) the location of electromagnetic radiation sensor 3000 is not linked by appliance 1100 to cannula 20 or to an IV dressing for the cannulation site N; (ii) appliance 1100 is useable with typical dressings for the IV cannulation site N; and (iii) minimal stress and strain is transferred by appliance 1100 to the skin S when changing between the first and second arrangements of fitting 1110. As the terminology is used herein, "link" or "linking" preferably refers to at least approximately fixing the relative locations of at least two objects.

A second embodiment of dressing 1000 is shown in FIGS. 4-6B. An appliance 1200 preferably includes (i) a fitting 1210 for receiving electromagnetic radiation sensor 3000, which senses if fluid is infusing the perivascular tissue P around transcutaneous sleeve 20c; (ii) a frame 1220 for distributing to the skin S forces acting on appliance 1200; and (iii) a body 1230 for covering fitting 1210 and frame 1220 with a soft haptic surface. As compared to appliance 1100 (FIGS. 2A-3B), the location of cannula 20 is linked by appliance 1200 to electromagnetic radiation sensor 3000. According to one embodiment, appliance 1200 preferably positions electromagnetic radiation sensor 3000 relative to the skin S within approximately five centimeters of the cannulation site N and preferably in a range of approximately one centimeter to approximately three centimeters away from the cannulation site N. According to other embodiments, appliance 1200 positions electromagnetic radiation sensor 3000 relative to skin S so as to generally overlie an infusate outlet of transcutaneous sleeve 20c.

Appliances 1100 and 1200 preferably include some features and advantages that are comparable. As the terminology is used herein, "comparable" refers to similar, if not identical, compositions, constructions, properties, functions or purposes, and preferably combinations thereof. Preferably, features of appliances 1100 and 1200 that are comparable include (i) fittings 1110 and 1210; (ii) chutes 1112 and 1212; (iii) latches 1118 and 1218; (iv) hoops 1122 and 1222; and (v) arms 1124 and 1224.

Appliance 1200 preferably includes one or more wings 1240 that are in addition to at least some of the features and advantages of appliance 1100. Preferably, individual wings 1240 perform several functions including (i) linking electromagnetic radiation sensor 3000 with respect to cannula 20; (ii) separating cannula 20 from the epidermis E; (iii) providing resistance to forces that tend to change the relative position of appliance 1200 with respect to the perivascular tissue P; and/or (iv) stabilizing the positions of cannula 20 and electromagnetic radiation sensor 3000 relative to the skin S. Each wing 1240 preferably is coupled with fitting 1210, frame 1220 or body 1230 and includes a first surface 1242 for contiguously engaging cannula 20 and a second surface 1244 for confronting the epidermis E. According to one embodiment, individual wings 1240 include portions of frame 1220 and body 1230.

Appliance 1200 preferably includes plural locating options for linking electromagnetic radiation sensor 3000 with respect to cannula 20. According to one embodiment, individual wings 1240 preferably extend in two generally opposite lateral directions with respect to axis A of fitting 1210. Accordingly, a footprint of appliance 1200 on the epidermis E preferably is approximately T-shaped or approximately Y-shaped and cannula 20 may be located on either one of the wings 1240 on opposite sides of electromagnetic radiation sensor 3000. According to other embodiments, a single wing 1240 preferably extends in one lateral direction with respect to axis A of fitting 1210. Accordingly, a footprint of appliance 1200 on the epidermis E preferably is approximately L-shaped with cannula 20 being located on wing 1240 extending to one side of electromagnetic radiation sensor 3000. Preferably, individual appliances 1200 with single wings 1240 that extend on different sides of electromagnetic radiation sensor 3000 may be included in a kit. Accordingly, one or another of appliances 1200 in the kit preferably is selected to provide the most suitable locating option for linking electromagnetic radiation sensor 3000 with respect to cannula 20. The most suitable locating option preferably is selected based on one or more factors including: (i) the location on the patient of the cannulation site N; (ii) the orientation of cannula 20 relative to the cannulation site N; (iii) minimizing movement of cannula 20 or electromagnetic radiation sensor 3000 due to pulling or snagging tubing 32 or sensor cable 5000; and (iv) comfort of the patient. Preferably, a single wing 1240 may make appliance 1200 more compact and plural wings 1240 on a single appliance 1200 may provide additional options for locating electromagnetic radiation sensor 3000 relative to cannula 20. Further, appliance 1200 may include perforations or shear line indicators for separating, e.g., tearing-off or cutting, at least one wing 1240 from the rest of appliance 1200. Accordingly, the size of appliance 1200 may be compacted and/or appliance 1200 may be made wingless in the manner of appliance 1100. Thus, an advantage of each of the aforementioned embodiments is increasing the options for how an anatomical sensor may be located on a patient relative to the cannulation site N.

Appliance 1200 preferably separates cannula 20 from the epidermis E. According to one embodiment, wing 1240 includes a thickness 1246 between first surface 1242 and second surface 1244. Preferably, thickness 1246 provides a spacer that prevents or at least minimizes contiguous engagement between the epidermis E and hub 20b of cannula 20. Wing 1240 therefore preferably eliminates or at least substantially reduces epidermal inflammation or breakdown, e.g., chafing or blistering, caused by cannula 20. Accordingly, wing 1240 eliminates or at least minimizes hub 20b as a source of epidermal inflammation or breakdown that may be observed when a healthcare giver evaluates the cannulation site N.

Wing(s) 1240 preferably supplement the ability of appliance 1200 to resist forces that tend to change the positions of electromagnetic radiation sensor 3000 and cannula 20 relative to the skin S and the perivascular tissue P. Preferably, a skeleton of appliance 1200 includes fitting 1210, frame 1220, and at least one wing rib 1248. Fitting 1210 preferably interacts with electromagnetic radiation sensor 3000 in a manner comparable to fitting 1110 discussed above. Preferably, frame 1220 includes a hoop 1222 coupled with fitting 1210 by at least one arm 1224. Thus, frame 1220 may be comparable to frame 1120 at least insofar as preferably contributing to distributing to the skin S the forces that act on fitting 1210. Appliance 1200 preferably resists changes to the relative position between superficies 3300 and the epidermis E by distributing over relatively large areas of the skin S the forces that may tend to move electromagnetic radiation sensor 3000 in the first arrangement of fitting 1210. Individual wing ribs 1248 preferably enlarge the area of the skin S over which frame 1220 distributes forces acting on fitting 1210. According to one embodiment, individual wing ribs 1248 preferably include a cantilever having a base coupled with frame 1220 and a tip disposed in a corresponding wing 1240. According to other embodiments, more than one wing rib 1248 may be disposed in a corresponding wing 1240, individual wing ribs 1248 may include a bifurcated cantilever, and/or individual cantilevers may include one or more branches. The skeleton of appliance 1200 therefore preferably enhances maintaining a substantially consistent relative position between electromagnetic radiation sensor 3000 and the perivascular tissue P for sensing over time if fluid from cannula 20 is infusing the perivascular tissue P.

Appliance 1200 preferably is sufficiently flexible to conform to the approximate contours of the skin S. For example, frame 1220 may include one or more lines of weakness disposed on hoop 1222, arm(s) 1224 and/or wing rib(s) 1248. As the terminology is used herein, "lines of weakness" preferably refers to living hinges or other suitable features for increasing flexibility at a particular location of the skeleton of appliance 1200.

Body 1230 preferably presents a soft haptic exterior surface of wings 1240. In a manner comparable to body 1130 discussed above, body 1230 is relatively supple, e.g., has a relatively lower hardness, and may be molded over fitting 1210, frame 1220 and wing rib(s) 1248. According to one embodiment, body 1230 preferably includes first surface 1242, at least a portion of second surface 1244, and a large portion of thickness 1246. The remaining portions of second surface 1244 and thickness 1246 preferably are occupied by wing rib(s) 1248. Accordingly, an individual wing 1240 preferably is primarily composed of the relatively supple material of body 1230 with wing rib(s) 1248 included for force distribution and/or structural reinforcement. According to other embodiments, one or more of hoop 1222, arms 1224 and wing ribs 1248 preferably are omitted from the skeleton of appliance 1200. Thus, individual wings 1240 preferably include portions of body 1230 with minimal or no reinforcement by the skeleton of appliance 1200. According to other embodiments, wing rib(s) 1248 preferably are excluded from an individual wing 1240.

Appliance 1200 includes a foundation 1250 that preferably (1) separates the rest of appliance 1200 from the epidermis E; and (2) couples appliance 1200 and the epidermis E. Preferably, foundation 1250 includes a panel 1252 that is coupled to a face of appliance 1200 confronting the skin S. According to one embodiment, panel 1252 preferably is adhered to second surface 1244 and separates at least one of fitting 1210, frame 1220 and body 1230 from the epidermis E. According to other embodiments, panel 1252 occludes chute 1212 for providing a barrier between the epidermis E and superficies 3300 in the second arrangement. Preferably, panel 1252 includes polyurethane or another sheet material that is biocompatible according to ISO 10993 and/or USP Class VI.

Foundation 1250 includes an adhesive 1254 preferably for bonding appliance 1200 to the epidermis E. Preferably, adhesive 1154 includes a silicone adhesive, an acrylic adhesive or another medical grade adhesive that is biocompatible according to ISO 10993 and/or USP Class VI. According to one embodiment, the shape and size of adhesive 1254 preferably is congruent with panel 1252. According to other embodiments, adhesive 1254 preferably is omitted in a window 1254a through which emitted and collected electromagnetic radiation 3002 and 3006 propagate. Preferably, foundation 1250 includes a release liner (not shown) that is removed to bond appliance 1200 to the epidermis E.

Figure 5:
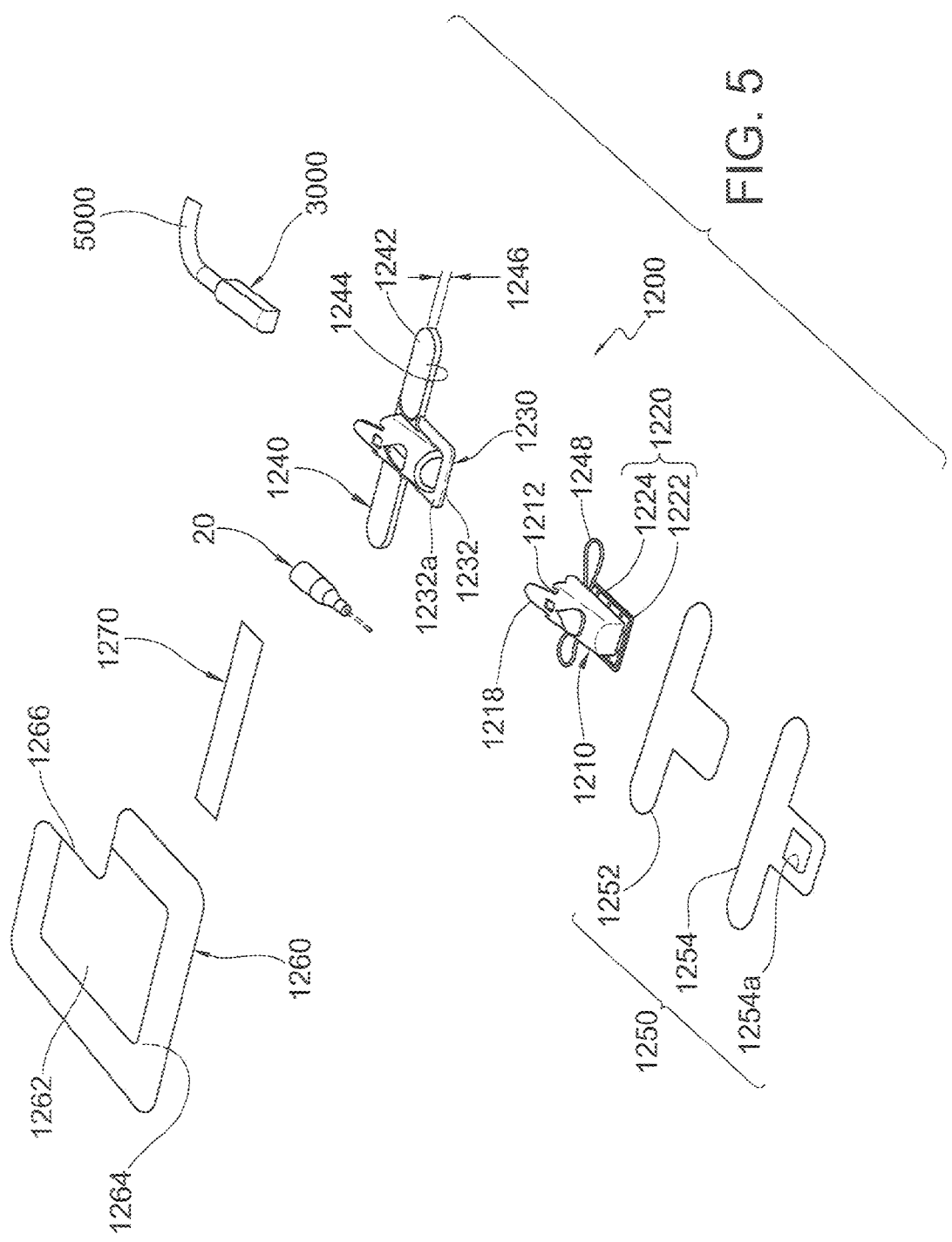
FIG. 5 is an exploded view of the dressing assembly shown in FIG. 4.

A kit including appliance 1200 preferably also includes at least one independent contamination barrier 1260 for overlying the epidermis E and at least a portion of cannula 20 while allowing visual inspection of the cannulation site N. FIG. 4 shows an exploded view with contamination barrier 1260 displaced from appliance 1200. Referring additionally to FIG. 5, contamination barrier 1260 preferably is biocompatible according to ISO 10993 and/or USP Class VI and may include a polyurethane membrane 1262 with a coating of medical grade acrylic adhesive 1264. Examples of typical contamination barriers include Tegaderm™, manufactured by 3M (St. Paul, Minn., USA), REACTIC™, manufactured by Smith & Nephew (London, UK), and other transparent or translucent polymer films that are substantially impervious to solids, liquids, microorganisms and/or viruses. Preferably, contamination barrier 1260 is supplied in the kit separate from appliance 1200 and is independently coupled to the skin S at different times or in different steps.

Appliance 1200 and contamination barrier 1260 preferably include form factors that cooperate with one another. According to one embodiment, body 1230 preferably includes a form factor such as a flange 1232 that covers hoop 1222 and arm(s) 1224. Preferably, flange 1232 includes a top surface 1232a to which adhesive 1264 may adhere membrane 1262 when appliance 1200 and contamination barrier 1260 are used in combination. According to one embodiment, a set of individual contamination barriers 1260 preferably accompanies each appliance 1200. Each of the contamination barriers 1260 in the set preferably includes a notch 1266 or another form factor having a peripheral edge that is sized and/or shaped to correspond with at least a portion of flange 1232 and/or wing 1240 on one or the other side of axis A. Accordingly, one or another of contamination barriers 1260 in the set preferably is selected to apply to the skin S on the side of axis A that cannula 20 is located. According to other embodiments, contamination barrier 1260 has a symmetrical shape that preferably is turned or otherwise reoriented to cooperatively engage appliance 1200 on either side of axis A that cannula 20 is located.

A method of using appliance 1200 to monitor if fluid is infusing perivascular tissue around cannula 20 preferably includes (i) coupling appliance 1200 to the skin S; (ii) coupling electromagnetic radiation sensor 3000 in the first arrangement of fitting 1210; and (iii) coupling cannula 20 with one wing 1240. Preferably, appliance 1200 is coupled with the skin S by adhesive 1254 or by another suitable epidermal fastener. Adhesive 1254 preferably is exposed to the skin S by removing a release liner (not shown). Electromagnetic radiation sensor 3000 preferably is translated along axis A to the first arrangement of fitting 1210 and securely latched. Preferably, one wing 1240 underlays cannula 20 and an adhesive strip 1270 (see FIG. 5) secures cannula 20 to wing 1240. According to one embodiment, cannula 20 is inserted in the blood vessel V and then one wing 1240 is positioned under cannula 20 before adhering appliance 1200 to the epidermis E. Adhesive strip 1270 subsequently overlies and couples cannula 20 with respect to wing 1240 before coupling electromagnetic radiation sensor 3000 in the first arrangement of fitting 1210. According to other embodiments, electromagnetic radiation sensor 3000 is coupled in the first arrangement of fitting 1210 before positioning one wing 1240 under cannula 20 and adhering appliance 1200 to the epidermis E. Adhesive strip 1270 subsequently overlies and couples cannula 20 with respect to wing 1240. Each of the aforementioned embodiments may also include adhering contamination barrier 1260 with top surface 1232a of flange 1232, as well as with the epidermis E. Preferably, electromagnetic radiation sensor 3000 may be moved between the first and second arrangements of fitting 1210 without decoupling appliance 1200 from the epidermis E, without decoupling cannula 20 or adhesive strip 1270 from wing 1240, and without decoupling contamination barrier 1260 from the epidermis E.

Appliance 1200 preferably is advantageous at least because (i) appliance 1200 may be physically associated with a dressing for the IV cannulation site N; (ii) appliance 1200 links electromagnetic radiation sensor 3000 and cannula 20; (iii) appliance 1200 includes a plurality of locating options for linking electromagnetic radiation sensor 3000 with respect to cannula 20; (iv) appliance 1200 maintains a substantially consistent relative position between electromagnetic radiation sensor 3000 and the perivascular tissue P for sensing over time if fluid from cannula 20 is infusing the perivascular tissue P; and (v) appliance 1200 eliminates or at least reduces epidermal inflammation or breakdown caused by cannula 20.

Appliance 1200 preferably also is advantageous insofar as preventing or minimizing forces that tend to distort the skin S while moving between the first and second arrangements of fitting 1210. It is believed that reducing distortion of the skin S reduces distortion of subcutaneous tissue including the perivascular tissue P and the blood vessel V, and therefore also reduces the likelihood of displacing cannula 20 while moving between the first and second arrangements of fitting 1210.

Figure 7:
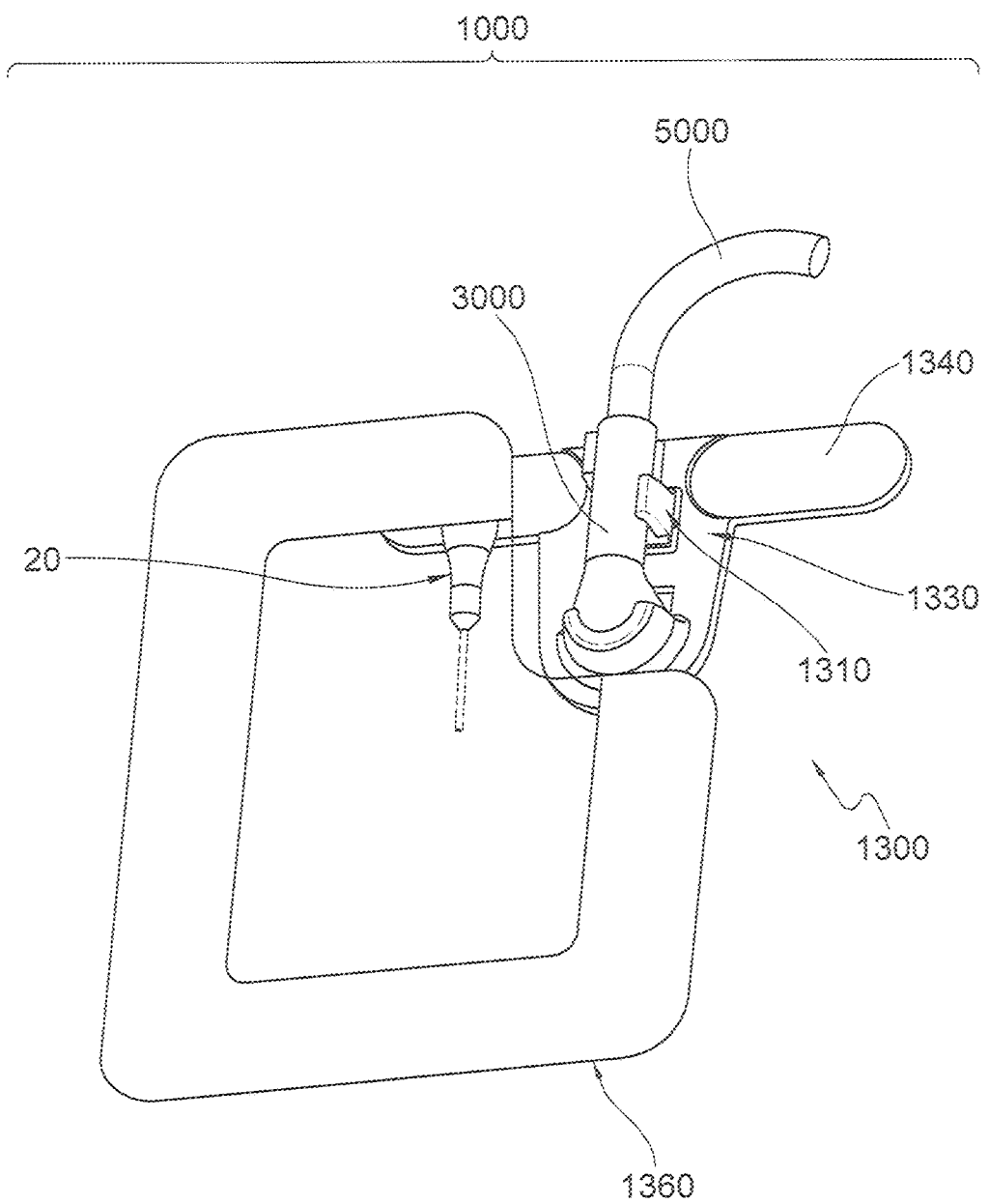
FIG. 7 is a partially exploded perspective view illustrating a dressing assembly including an embodiment of an appliance according to the present disclosure, an electromagnetic radiation sensor, a cannula, and a barrier film.
Figure 8:
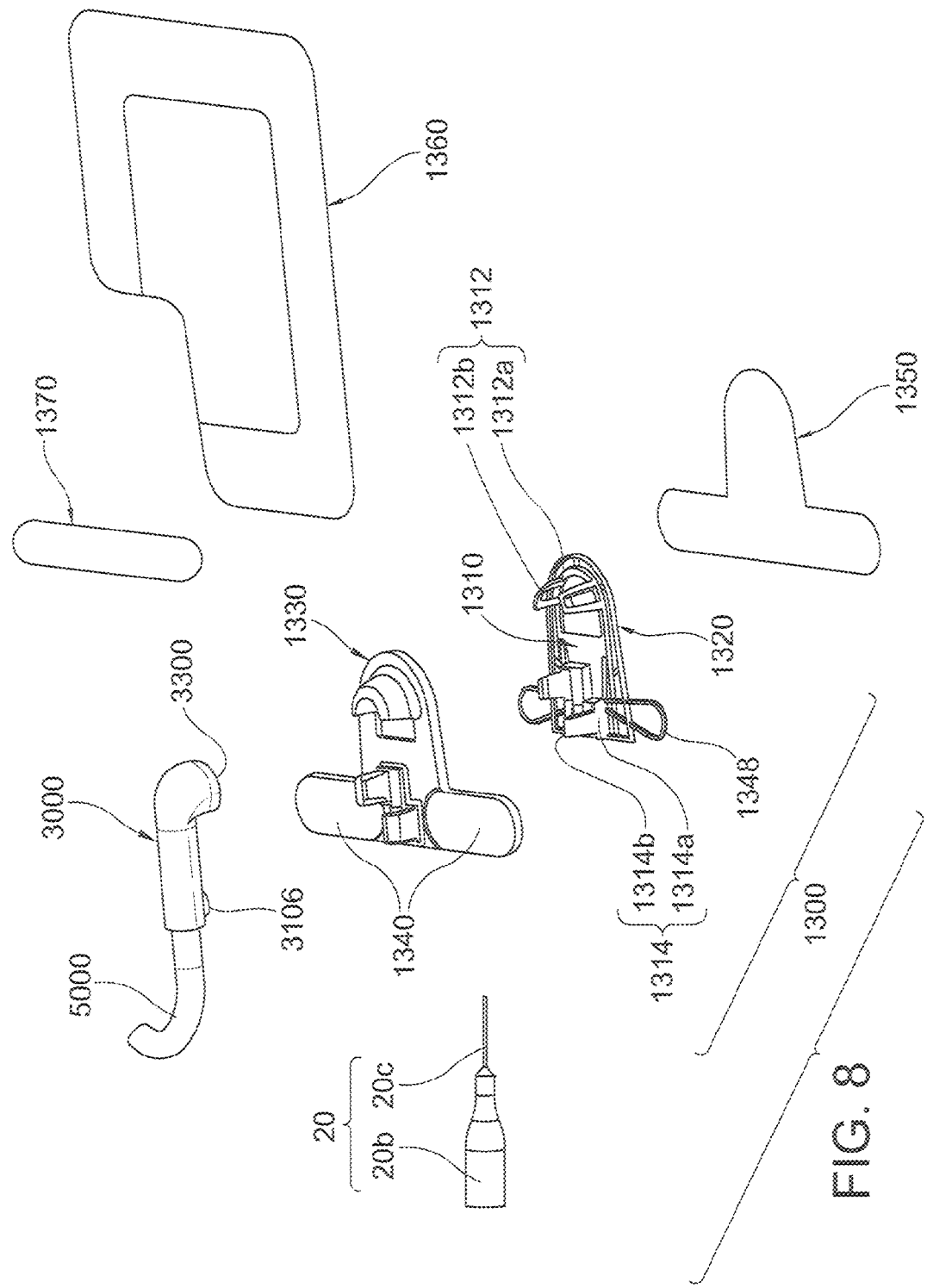
FIG. 8 is an exploded view of the dressing assembly shown in FIG. 7.
Figure 9:
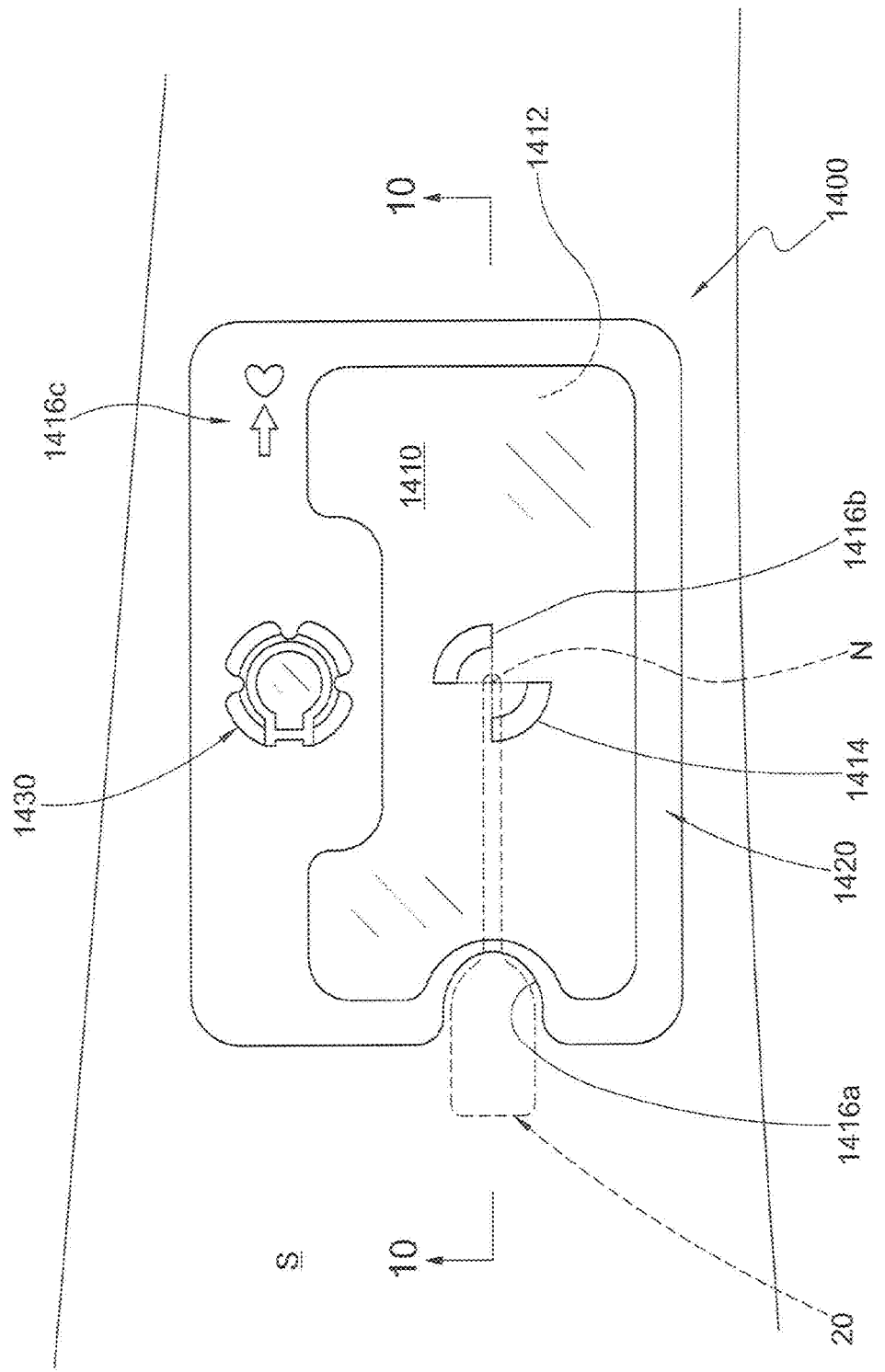
FIG. 9 is a schematic view illustrating an embodiment according to the present disclosure of a dressing assembly including an appliance integrated with a barrier film. A cannula is also shown in broken line.
Figure 10:
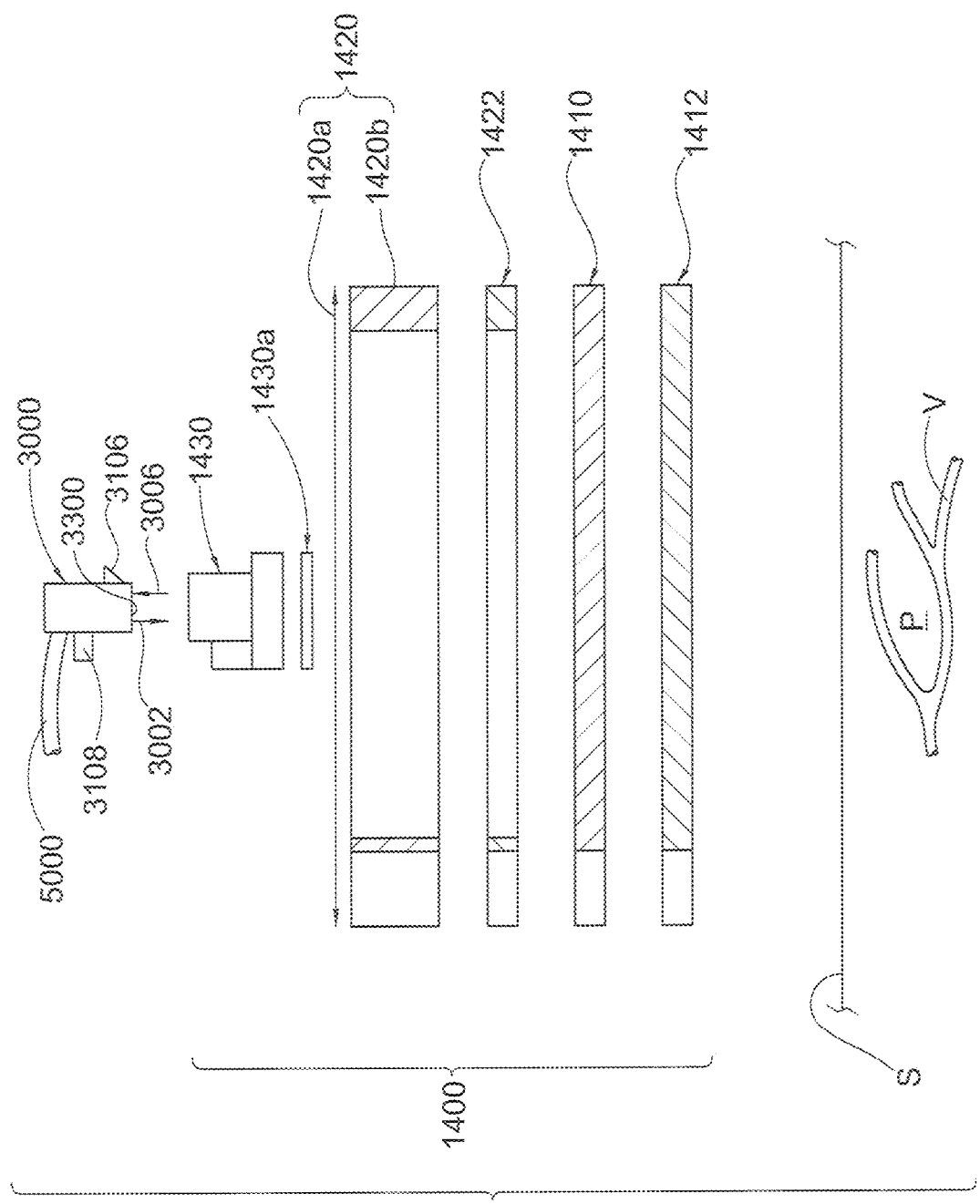
FIG. 10 is an exploded schematic partial cross-section view taken along line X-X in FIG. 9. An electromagnetic radiation sensor and a portion of a sensor cable are also shown. Certain features of Animalia tissue are also shown.

A third embodiment of dressing 1000 is shown in FIGS. 7 and 8. An appliance 1300 preferably includes (i) a fitting 1310 for receiving electromagnetic radiation sensor 3000, which senses if fluid is infusing the perivascular tissue P around transcutaneous sleeve 20c; (ii) a frame 1320 for distributing forces acting on appliance 1300 to the skin S; and (iii) a body 1330 for covering fitting 1310 and frame 1320 with a soft haptic surface. As compared to appliances 1100 and 1200 (FIGS. 2A-6B), a first arrangement of fitting 1310 preferably is an alternate to the first arrangements of fittings 1110 and 1210; however, the second arrangements of fittings 1110, 1210 and 1310 preferably are similar insofar as releasing electromagnetic radiation sensor 3000 from the respective first arrangements. Preferably, other features and advantages of appliances 1100, 1200 and 1300 are comparable including (i) frames 1120, 1220 and 1320; (ii) wings 1240 and 1340; (iii) wing ribs 1248 and 1348; (iv) bodies 1130, 1230 and 1330; (v) foundations 1150, 1250 and 1350; (vi) contamination barriers 1260 and 1360; and (vii) adhesive strips 1270 and 1370. According to one embodiment, appliance 1300 preferably positions electromagnetic radiation sensor 3000 relative to the skin S within approximately five centimeters of the cannulation site N and preferably in a range of approximately one centimeter to approximately three centimeters away from the cannulation site N. According to other embodiments, appliance 1300 positions electromagnetic radiation sensor 3000 relative to skin S so as to generally overlie an infusate outlet of transcutaneous sleeve 20c.

The first arrangement of fitting 1310 preferably includes sets of pegs for constraining relative movement between electromagnetic radiation sensor 3000 and appliance 1300. As the terminology is used herein, "peg" preferably refers to a projecting piece or portion of a surface that is used as a support or boundary. According to one embodiment, fitting 1310 includes a first set of pegs 1312 disposed proximate superficies 3300 and a second set of pegs 1314 disposed proximate sensor cable 5000. Preferably, a cage of appliance 1300 includes first and second sets of pegs 1312 and 1314. The cage preferably defines a pocket for receiving electromagnetic radiation sensor 3000 and constrains relative movement between electromagnetic radiation sensor 3000 and appliance 1300 in the first arrangement of fitting 1310. Preferably, first set of pegs 1312—two pegs are shown in FIG. 8—preferably includes a form factor that generally conforms to the contours of electromagnetic radiation sensor 3000 to define a first portion of the cage. Individual pegs 1312 preferably include a cantilever extending between a base 1312a and a tip 1312b. Preferably, base(s) 1312a are coupled to frame 1320 and tip(s) 1312b at least slightly overlie electromagnetic radiation sensor 3000 to constrain movement away from the skin S in the first arrangement of fitting 1310. According to one embodiment, individual pegs 1312 preferably are bifurcated at base 1312a and converge at tip 1312b.

Second set of pegs 1314—two pegs are shown in FIG. 8—preferably are disposed on opposite sides of electromagnetic radiation sensor 3000 to define a second portion of the cage. Individual pegs 1314 preferably include cantilevers extending between a base 1314a and a tip 1314b. Preferably, bases 1314a are coupled to frame 1320 and a portion of electromagnetic radiation sensor 3000 proximate sensor cable 5000 is received between tips 1314b to constrain relative angular movement and/or provide strain relief for electromagnetic radiation sensor 3000 in the first arrangement of fitting 1310.

Other embodiments of appliance 1300 may have sets including different numbers, locations and shapes of pegs 1312 and pegs 1314. For example, the first set may include more or less than two pegs 1312; the second set may include more than a single peg 1314 located on each side of electromagnetic radiation sensor 3000; and/or tip 1314b of at least one peg 1314 may include a bump or other projection for retaining electromagnetic radiation sensor 3000 in the first arrangement of fitting 1310.

Body 1330 preferably presents a soft haptic exterior surface overlying the relatively rigid fitting 1310 and frame 1320 of appliance 1300. In a manner comparable to bodies 1130 and 1230 discussed above, body 1330 is relatively supple, e.g., has a relatively lower hardness, and may be molded over fitting 1310, frame 1320 and wing rib(s) 1348.

Appliance 1300 preferably includes a link between electromagnetic radiation sensor 3000 and cannula 20. Preferably, appliance 1300 includes at least one wing 1340 coupled with at least one of fitting 1310, frame 1320, and body 1330. Individual wings 1340 preferably are comparable to individual wings 1240 of appliance 1200 at least insofar as (i) locating electromagnetic radiation sensor 3000 with respect to cannula 20; (ii) separating cannula 20 from the epidermis E; and/or (iii) providing resistance to forces that tend to change the position of electromagnetic radiation sensor 3000 relative to the perivascular tissue P.

Individual wings 1340 of appliance 1300 preferably separate cannula 20 from the epidermis E, and preferably supplement the ability of appliance 1300 to resist forces that tend to change the position of electromagnetic radiation sensor 3000 relative to the perivascular tissue P. Preferably, wing 1340 includes a thickness that eliminates or at least reduces epidermal inflammation or breakdown caused by cannula 20. Preferably, a skeleton of appliance 1300 includes fitting 1310, frame 1320, and at least one wing rib 1348 to distribute to the skin S the forces that act on fitting 1310. Further, appliance 1300 preferably resists changes to the relative position between superficies 3300 and the perivascular tissue P by distributing over relatively large areas of the skin S the forces that may tend to move electromagnetic radiation sensor 3000 in the first arrangement of fitting 1310. Accordingly, appliance 1300 is comparable at least in this regard to appliances 1100 and 1200. Individual wing ribs 1348 preferably enhance the capability of individual wings 1340 to distribute to the skin S forces that act on fitting 1310. The skeleton of appliance 1300 therefore preferably facilitates maintaining a substantially consistent relative position between electromagnetic radiation sensor 3000 and the perivascular tissue P for sensing over time if fluid from cannula 20 is infusing the perivascular tissue P.

Appliance 1300 preferably is comparable to appliance 1200 insofar as including plural locating options for linking electromagnetic radiation sensor 3000 with respect to cannula 20. Factors for selecting the most suitable locating option are discussed above with regard to appliance 1200. Appliance 1300 also therefore includes the advantage of having more than one choice for how an anatomical sensor may be located on a patient relative to the cannulation site N.

A process for implementing appliance 1300 to sense if fluid is infusing perivascular tissue around transcutaneous sleeve 20c preferably includes (i) coupling appliance 1300 to the skin S; (ii) coupling electromagnetic radiation sensor 3000 in the first arrangement of fitting 1310; and (iii) coupling cannula 20 with one wing 1340. A process for coupling electromagnetic radiation sensor 3000 with appliance 1300 preferably includes (i) orienting electromagnetic radiation sensor 3000 obliquely with respect to frame 1320; (ii) slipping electromagnetic radiation sensor 3000 under tip(s) 1312a; and (iii) pivoting electromagnetic radiation sensor 3000 between peg(s) 1314. Accordingly, the cage including first and second sets of pegs 1312 and 1314 preferably constrains relative movement between electromagnetic radiation sensor 3000 and appliance 1300. Preferably, the second arrangement of fitting 1310 includes reversing the above process for coupling electromagnetic radiation sensor 3000 with appliance 1300. Decoupling electromagnetic radiation sensor 3000 in the second arrangement of fitting 1310 accordingly permits multiple uses of electromagnetic radiation sensor 3000 in the same or a different appliance 1300.

A fourth embodiment of dressing 1000 is shown in FIGS. 9-11D. An appliance 1400 preferably includes (i) a pane 1410 overlying the cannulation site N; and (ii) a fitting 1430 for receiving electromagnetic radiation sensor 3000, which senses if fluid is infusing the perivascular tissue P around transcutaneous sleeve 20*c*. Appliance 1400 preferably includes an integrated contamination barrier that is substantially impervious to solids, liquids, microorganisms and/or viruses. Preferably, the contamination barrier may be semipermeable to allow air or vapor to pass, thus permitting the epidermis E to breathe.

Pane 1410 preferably permits viewing the cannulation site N. Preferably, pane 1410 is transparent or translucent to light in the visible portion of the electromagnetic spectrum, for example, light having wavelengths between approximately 380 nanometers and approximately 760 nanometers. These wavelengths generally correspond to a frequency range of approximately 400 terahertz to approximately 790 terahertz. Pane 1410 preferably includes polyurethane film or another suitable material and/or construction to also provide a contamination barrier that may be transparent or translucent.

An adhesive 1412 preferably bonds pane 1410 to the skin S around the cannulation site N. Preferably, adhesive 1412 includes a silicone adhesive, an acrylic adhesive or another medical grade adhesive that is biocompatible according to ISO 10993 and/or USP Class VI. Adhesive 1412 may be applied to pane 1410 on the entire surface that confronts the epidermis E, or adhesive 1412 may be omitted from one or more portions of the surface. Also, the strength of the bond between pane 1410 and the epidermis E may vary according to different embodiments of appliance 1400. For example, stronger or more adhesive 1412 may be used for coupling appliance 1400 to relatively robust skin, e.g., adult skin, and weaker or less adhesive 1412 may be used for coupling appliance 1400 to relatively delicate skin, e.g., pediatric skin.

Pane 1410 may also include a diagnostic tool 1414 to assist in visually analyzing symptoms of infiltration or extravasation. For example, diagnostic tool 1414 may include a set of concentric arcs, a geometric shape, a set of parallel lines, a color gradient, or another suitable reticle for evaluating conditions at the epidermis E that may be symptomatic of infiltration or extravasation. According to one embodiment, the appearance of a set of concentric arcs or a geometric shape may become distorted when the epidermis E, and thus pane 1410, is distended due to edema. According to another embodiment, changes in the coloration of the epidermis E may be evaluated by periodic comparison with a color gradient included on pane 1410.

Appliance 1400 is preferably located or oriented with respect to at least one of cannula 20, the cannulation site N, or an anatomical feature. According to one embodiment, appliance 1400 may include a notch 1416*a* or another suitable guide that is sized or shaped for cooperating with at least a portion of cannula 20. According to another embodiment, pane 1410 may include crosshairs 1416*b* or another suitable guide for locating appliance 1400 relative to the cannulation site N. According to another embodiment, indicia, symbols and/or other markings preferably provide a guide for relatively positioning appliance 1400 with resect to an anatomical feature. For example, guide 1416*c* includes an arrow and a symbol that suggests a position for appliance 1400 relative to the heart.

Appliance 1400 preferably includes a frame 1420 coupled to pane 1410. Frame 1420 preferably has greater resistance to deformation than does pane 1410. Accordingly, frame 1420 may maintain the general shape of pane 1410 while appliance 1400 is laid over the cannulation site N. According to one embodiment, frame 1420 entirely cinctures pane 1410. According to other embodiments, frame 1420 may (i) partially cincture pane 1410; (ii) extend from a peripheral portion of pane 1410 toward an interior portion of pane 1410; (iii) extend from the interior portion toward the peripheral portion; (iv) be spaced from the peripheral portion; or (v) include some combination of (i)-(iv). Frame 1420 preferably includes polyvinyl chloride, polyethylene, polypropylene, or another suitable material that is relatively rigid with respect to pane 1410. According to one embodiment, frame 1420 may include polyethylene tape 1420*a* being relatively associated with or disposed on a pad of polyvinyl chloride foam 1420*b*.

Frame 1420 is preferably transparent or translucent to visible light for viewing the epidermis E in the vicinity of the cannulation site N. Preferably, frame 1420 absorbs or blocks the transmission of radiation having the same wavelength(s) as emitted and collected electromagnetic radiation 3002 and 3006, e.g., near-infrared radiation. Thus, according to one embodiment, the epidermis E that underlies frame 1420 may be optically visible and shielded from ambient near-infrared radiation.

Frame 1420 is preferably coupled to pane 1410 by an adhesive 1422 or another suitable coupling. According to one embodiment, adhesive 1422 preferably provides a coupling between pane 1410 and frame 1420 that is relatively stronger than the bond between pane 1410 and the epidermis E. Accordingly, pane 1410 remains attached to frame 1420 when separating dressing 1400 from the epidermis E. Adhesive 1422 according to another embodiment of appliance 1400 preferably provides a coupling between pane 1410 and frame 1420 that is relatively weaker than the bond between pane 1410 and the epidermis E. Accordingly, frame 1420 may be released from pane 1410 after appliance 1400 is laid over the cannulation site N.

Fitting 1430 preferably couples electromagnetic radiation sensor 3000 with appliance 1400. There are preferably two arrangements of fitting 1430 with respect to electromagnetic radiation sensor 3000. A first arrangement of fitting 1430 preferably retains electromagnetic radiation sensor 3000 relative to appliance 1400 for monitoring infiltration or extravasation during an infusion with cannula 20. Accordingly, the first arrangement of fitting 1430 with respect to electromagnetic radiation sensor 3000 preferably senses over time if fluid from cannula 20 is infusing the perivascular tissue P. A second arrangement of fitting 1430 preferably releases electromagnetic radiation sensor 3000 from the first arrangement. The first arrangement preferably includes one or more projections 3106 (see FIG. 10) on electromagnetic radiation sensor 3000 being snapped under corresponding latches 1432*a* (see FIGS. 11B and 11C) of fitting 1430. Accordingly, the second arrangement preferably includes snapping the projections 3106 over latches 1432*a* to release electromagnetic radiation sensor 3000 from the first arrangement. Other embodiments may use a cap, a resilient element, or another suitable device that, in the first arrangement, retains electromagnetic radiation sensor 3000 in fitting 1430 and preferably biases superficies 3300 toward the epidermis E and, in the second arrangement, releases electromagnetic radiation sensor 3000 from fitting 1430, e.g., allowing electromagnetic radiation sensor 3000 to separate from fitting 1430. Accordingly, the first and second arrangements permit electromagnetic radiation sensor 3000 to have multiple uses with a plurality of appliances 1400 that are individually applied to patients' epidermises.

Fitting 1430 may be indirectly or directly coupled to pane 1410. According to one embodiment of dressing 1400, frame 1420 preferably couples fitting 1430 to pane 1410. According to another embodiment of dressing 1400, fitting 1430 and pane 1410 are preferably directly coupled. Fitting 1430 is preferably fixed to appliance 1400 using an adhesive 1430a (see FIG. 10) or another suitable coupling that is relatively stronger than the bond between pane 1410 and the epidermis E. Moreover, adhesive 1430a preferably couples fitting 1430 to frame 1420 and provides a coupling that is at least as strong as the coupling between frame 1420 and pane 1410.

Details according to one embodiment of fitting 1430 are shown in FIGS. 11A-11D. Preferably, fitting 1430 includes a wall 1432 that defines a pocket 1434 for receiving electromagnetic radiation sensor 3000. In the first arrangement of fitting 1430, wall 1432 may (i) entirely surround electromagnetic radiation sensor 3000; (ii) include a plurality of individual segments or posts intermittently disposed around electromagnetic radiation sensor 3000; or (iii) have any suitable configuration for locating electromagnetic radiation sensor 3000 with respect to dressing 1400. Wall 1432 preferably includes one or more latches 1432a (three are shown in FIG. 11B) that cooperate with projection(s) 3106 for retaining electromagnetic radiation sensor 3000 in pocket 1434 in the first arrangement of fitting 1430. Preferably, fitting 1430 maintains electromagnetic radiation sensor 3000 in a desired orientation with respect to dressing 1400. According to one embodiment, wall 1432 includes a recess 1432b that, in the first arrangement, cooperatively receives an anti-rotation projection 3008 (see FIG. 10) on electromagnetic radiation sensor 3000. According to other embodiments, fitting 1430 and electromagnetic radiation sensor 3000 may include any suitable mating features for eliminating or at least minimizing rotation of electromagnetic radiation sensor 3000 in pocket 1434.

Fitting 1430 and appliance 1400 are preferably coupled via an interface that permits appliance 1400 to approximately conform to epidermis E. Preferably, a rim or flange 1436 projects from wall 1434 and provides a surface for adhesive 1430a at the interface between fitting 1430 and appliance 1400. According to one embodiment, flange 1436 may include a plurality of segments 1436a (four are shown in FIG. 11A) separated by individual gaps 1436b (three are shown in FIG. 11A). One or more lines of weakness 1438 may be disposed on flange 1436 to increase flexibility of the interface between fitting 1430 and appliance 1400. Accordingly, fitting 1430 may approximately conform to the contours of epidermis E to thereby facilitate, in the first arrangement, maintaining electromagnetic radiation sensor 3000 relative to the skin S.

Appliance 1400 preferably integrates in a single unit an occlusive barrier and a retainer for an anatomical sensor. According to one embodiment, the anatomical sensor may include electromagnetic radiation sensor 3000 or another sensor for sensing over time a change of body structure, e.g., infiltration and extravasation. Preferably, the occlusive barrier includes pane 1410 for protecting the cannulation site N and the retainer includes fitting 1430 for positioning electromagnetic radiation sensor 3000 to sense if fluid is infusing the perivascular tissue P. Fitting 1430 preferably permits electromagnetic radiation sensor 3000 to be decoupled and recoupled with appliance 1400, or decoupled from a first appliance 1400 and coupled to a second appliance 1400. Appliance 1400 preferably also includes frame 1420 for distributing forces over a larger area of the skin S. For example, forces due to pulling or snagging sensor cable 5000 may be distributed by pane 1410, frame 1420 and fitting 1430 over an area of the skin S that is larger than that overlaid by superficies 3300. Appliance 1400 therefore preferably enhances an approximately consistent positional relationship between electromagnetic radiation sensor 3000 and the perivascular tissue P when sensing infiltration or extravasation. Appliance 1400 is advantageous at least because applying an occlusive dressing for an intravascular infusion concurrently establishes an approximately consistent location for an infiltration/extravasation sensor.

Figure 12:
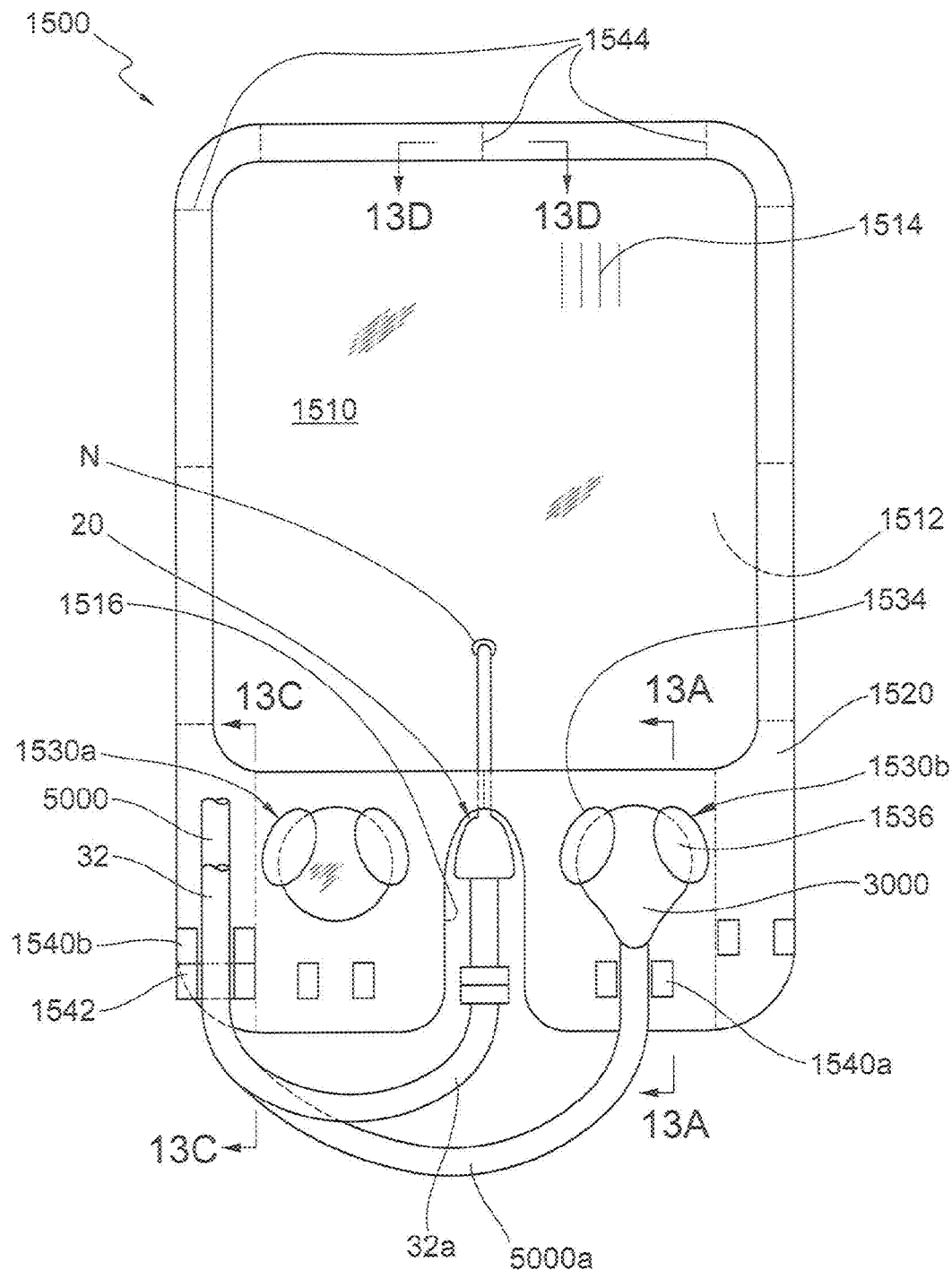
FIG. 12 is a schematic view illustrating an embodiment according to the present disclosure of a dressing assembly including an appliance integrated with a barrier film. An electromagnetic radiation sensor, a portion of a sensor cable, a cannula and a portion of an administration set are also shown.

A fifth embodiment of dressing 1000 is shown in FIGS. 12-13D. An appliance 1500 preferably includes (i) a contamination barrier overlying the cannulation site N; and (ii) a plurality of location options for coupling electromagnetic radiation sensor 3000 to sense if fluid is infusing the perivascular tissue P around transcutaneous sleeve 20c. The contamination barrier preferably is substantially impervious to solids, liquids, microorganisms and/or viruses. Preferably, appliance 1500 may be semi-permeable to allow air or vapor to pass, thus permitting the epidermis E to breathe.

The contamination barrier of appliance 1500 preferably includes a pane 1510 for viewing the cannulation site N. Preferably, pane 1510 is transparent or translucent to light in the visible portion of the electromagnetic spectrum. Pane 1510 preferably includes a polyurethane film or another suitable material and/or construction for providing a contamination barrier that may be transparent or translucent.

An adhesive 1512 preferably bonds pane 1510 to the epidermis E (not indicated in FIG. 12) around the cannulation site N. Preferably, adhesive 1512 includes an acrylic adhesive that is suitable for contact with the epidermis E or another medical grade adhesive that is biocompatible according ISO 10993 and/or USP Class VI. Adhesive 1512 may be applied to pane 1510 on the entire surface that confronts the epidermis E, or adhesive 1512 may be omitted from one or more portions of the surface. Also, the strength of the bond between pane 1510 and the epidermis E may vary according to different embodiments of appliance 1500. For example, stronger or more adhesive 1512 may be used for coupling appliance 1500 to relatively robust skin, e.g., adult skin, and weaker or less adhesive 1512 may be used for coupling appliance 1500 to relatively delicate skin, e.g., pediatric skin.

Pane 1510 may also include a diagnostic tool 1514 to assist in visually analyzing symptoms of infiltration or extravasation. For example, diagnostic tool 1514 may include a set of concentric arcs, a geometric shape, a set of parallel lines, a color gradient, or another suitable reticle for evaluating conditions at the epidermis E that may be symptomatic of infiltration or extravasation. According to one embodiment, the appearance of a set of parallel lines may become distorted when the epidermis E, and thus pane 1510, is distended due to edema. According to another embodiment, changes in the coloration of the epidermis E may be evaluated by periodic comparison with a color gradient included on pane 1510.

Pane 1510 may include one or more guides for positioning or orienting appliance 1500 on the skin S. According to one embodiment, guide 1516 preferably includes a notch or some other feature of appliance 1500 that may be sized or shaped to receive a portion of cannula 20, e.g., hub 20b.

Appliance 1500 preferably includes a frame 1520 coupled to pane 1510. According to one embodiment of appliance 1500, a coupling between pane 1510 and frame 1520 is preferably relatively stronger than the bond between pane 1510 and the epidermis E. Accordingly, pane 1510 remains attached to frame 1520 when separating appliance 1500 from the epidermis E.

Frame 1520 preferably has greater resistance to deformation than does pane 1510. Accordingly, frame 1520 may maintain the shape of pane 1510 while appliance 1500 is laid over the cannulation site N. According to one embodiment, frame 1520 entirely cinctures pane 1510. According to other embodiments, frame 1520 may (i) partially cincture pane 1510; (ii) extend from a peripheral portion of pane 1510 toward an interior portion of pane 1510; (iii) extend from the interior portion toward the peripheral portion; (iv) be spaced from the peripheral portion; or (v) include some combination of (i)-(iv). Frame 1520 preferably includes polyvinyl chloride, polyethylene, polypropylene, or another suitable material that is relatively rigid with respect to pane 1510. For example, frame 1520 may include a pad of polyvinyl chloride foam. Frame 1520 may be opaque, but is preferably transparent or translucent to visible light for viewing the epidermis E in the vicinity of the cannulation site N. Preferably, frame 1520 absorbs or blocks the transmission of electromagnetic radiation having the same wavelength(s) emitted and/or collected via superficies 3300, e.g., near-infrared radiation. Thus, according to one embodiment, the epidermis E that underlies frame 1520 may be optically visible and shielded from ambient near-infrared radiation.

Appliance 1500 preferably includes a plurality of fittings to provide alternate location options for coupling with electromagnetic radiation sensor 3000 to appliance 1500. Preferably, first fitting 1530*a* and second fitting 1530*b* are disposed at locations on opposite sides of guide 1516. Accordingly, the first arrangements of first and second fittings 1530*a* and 1530*b* preferably include location options for retaining electromagnetic radiation sensor 3000 on either side of guide 1516 for monitoring infiltration or extravasation during an infusion with cannula 20. Second arrangements of first fitting 1530*a* and second fitting 1530*b* preferably release electromagnetic radiation sensor 3000 from the first arrangements for the respective fittings.

Appliance 1500 preferably includes multiple fittings to permit multiple options for locating electromagnetic radiation sensor 3000 relative to the cannulation site N. Preferably, electromagnetic radiation sensor 3000 may be disposed in one of first and second fittings 1530*a* and 1530*b* with the other of first and second fittings 1530*a* and 1530*b* may be used for controlling tubing 32 and/or sensor cable 5000. Permutations of the arrangements of first and second fittings 1530*a* and 1530*b* with respect to electromagnetic radiation sensor 3000 may be characterized as "conditions" of appliance 1500. For example, a first condition of appliance 1500 may be characterized by the second arrangements of first and second fittings 1530*a* and 1530*b*. Accordingly, electromagnetic radiation sensor 3000 is not coupled to appliance 1500 in the first condition. Electromagnetic radiation sensor 3000 may be moved from the first condition to a second condition of appliance 1500 so as to be in the first arrangement of the first fitting 1530*a* and in the second arrangement of second fitting 1530*b*. Accordingly, electromagnetic radiation sensor 3000 would be retained in first fitting 1530*a* on the left-hand side of guide 1516 as viewed in FIG. 12. Electromagnetic radiation sensor 3000 may also be moved from the first condition to a third condition of appliance 1500 so as to be in the first arrangement of the second fitting 1530*b* and in the second arrangement of first fitting 1530*a*. Accordingly, electromagnetic radiation sensor 3000 would be retained in second fitting 1530*b* on the right-hand side of guide 1516 as viewed in FIG. 12. Appliance 1500 may also be changed between the second and third conditions, e.g., moving electromagnetic radiation sensor 3000 to the other side of guide 1516, and may also be changed from either of the second or third conditions to the first condition, e.g., decoupling electromagnetic radiation sensor 3000. Accordingly, electromagnetic radiation sensor 3000 preferably has multiple uses with a plurality of individual dressings 1500 and on whichever side of guide 1516 is advantageous for a particular patient or a particular cannulation site N. Factors for evaluating which of first and second fittings 1530*a* and 1530*b* may be advantageous to use for retaining electromagnetic radiation sensor 3000 preferably include reducing the likelihood of pulling or snagging sensor cable 5000, properly placing electromagnetic radiation sensor 3000 relative to the cannulation site N, and patient comfort.

Referring additionally to FIG. 13A, individual fittings preferably are each capable of retaining electromagnetic radiation sensor 3000. Preferably, individual fittings, e.g., first fitting 1530*a* or second fitting 1530*b*, each include a pocket 1532 that is defined by a wall 1534. Pocket 1532 preferably receives electromagnetic radiation sensor 3000 (shown in dash-dot line in FIG. 13A) in the first arrangement. Preferably, pane 1510 extends across pocket 1532 and is interposed between superficies 3300 and the epidermis E in the first arrangement, as shown in, e.g., FIG. 13A. According to one embodiment, wall 1534 preferably includes a plurality of individual segments disposed partially around pocket 1532. Preferably, at least one tab 1536 projects from wall 1534 and overlies a portion of electromagnetic radiation sensor 3000 in the first arrangement. Elastic deformation of wall 1534 or tab 1536 preferably permits electromagnetic radiation sensor 3000 to snap-in to pocket 1532 in the first arrangement and to snap-out from pocket 1532 in the second arrangement. According to one embodiment, tab 1536 preferably includes a raised portion or bump 1538 for biasing superficies 3300 toward the epidermis E by contiguously engaging electromagnetic radiation sensor 3000 in the first arrangement. According to other embodiments, individual fittings may include a latch, a cap, a resilient element, or another suitable device that, in a first arrangement, retains electromagnetic radiation sensor 3000 in pocket 1532 and preferably biases superficies 3300 toward the epidermis E, and in a second arrangement, releases electromagnetic radiation sensor 3000 to move out of pocket 1532.

Referring additionally to FIG. 13B, electromagnetic radiation sensor 3000 and individual fittings in the first arrangement preferably are coupled in a preferred manner. Preferably, a portion of electromagnetic radiation sensor 3000 has a first feature that cooperates with a second feature of pocket 1532. According to one embodiment, electromagnetic radiation sensor 3000 includes a front-side cylindrical portion 3142 having a first cross-section shape and pocket 1532 has a second cross-section shape that matingly receives front-side cylindrical portion 3142. Preferably, the first and second cross-sectional shapes are approximately congruent circles or other suitable mating shapes. Portions of electromagnetic radiation sensor 3000 other than front-side cylindrical portion 3162 preferably do not fit in pocket 1532. According to one embodiment, electromagnetic radiation sensor 3000 preferably includes a backside cylindrical portion 3144 having a third cross-section shape, e.g., a tear drop shape, that does not matingly cooperate with the second cross-section shape of pocket 1532. Accordingly, electromagnetic radiation sensor 3000 preferably can matingly engage individual fittings in only one manner.

Referring additionally to FIG. 13C, strain relief devices preferably redirect forces from sensor cable 5000 to appliance 1500. Preferably, individual fittings, e.g., first fitting 1530a or second fitting 1530b, each include a set of strain relief devices that contiguously engage sensor cable 5000 in the first arrangement. According to one embodiment, each set of strain relief devices preferably includes a first fixture 1540a and a second fixture 1540b. Individual fixtures 1540a or 1540b preferably each include a pair of posts separated by a gap that is smaller than the diameter of sensor cable 5000. Accordingly, sensor cable 5000 may be retained by an interference fit between a pair of posts that preferably limit lateral and/or longitudinal movement of sensor cable 5000 relative to frame 1520.

Preferably, first and second fixtures 1540a and 1540b are disposed on opposite sides of guide 1516. In the first arrangement, first fixture 1540a preferably retains sensor cable 5000 proximate a first one of the first and second fittings 1530a and 1530b, and second fixture 1540b preferably retains sensor cable 5000 and tubing 32 proximate a second one of the first and second fittings 1530a and 1530b. First fixture 1540a of second fitting 1530b is shown on the right-hand side of guide 1516 as viewed in FIG. 12 and second fixture 1540b of second fitting 1530b is shown on the left-hand side of guide 1516 as viewed in FIG. 12. According to one embodiment, first fixture 1540a preferably cooperates with sensor cable 5000 to eliminate or at least minimize rotation of electromagnetic radiation sensor 3000 in pocket 1532, and second fixture 1540b preferably establishes a first bight 5000a and a second bight 32a for sensor cable 5000 and tubing 32, respectively.

Appliance 1500 includes substantially identical features at different location options to increase compatibility of a single dressing for individual patients' cases. Preferably, multiple fittings and fixtures permit selecting the best available option for positioning electromagnetic radiation sensor 3000 relative to the cannulation site N and for controlling sensor cable 5000 and/or tubing 32. Selecting either first fitting 1530a or second fitting 1530b preferably reduces the likelihood of pulling or snagging sensor cable 5000 and/or tubing 32, positions electromagnetic radiation sensor 3000 proximate to the cannulation site N, and increases patient comfort.

A clip 1542 preferably couples tubing 32 and sensor cable 5000. Preferably, clip 242 may be fixed to sensor cable 5000 at a selected distance from electromagnetic radiation sensor 3000. The distance is preferably selected to cooperate with second fixture 1540b for consistently establishing an approximate size and radius of first bight 5000a. According to one embodiment, clip 1542 abuts against second fixture 1540b. Clip 1540 preferably includes a first portion cincturing sensor cable 5000 and a second portion having an opening for receiving and retaining, e.g., by interference fit, tubing 32. Thus, first fixture 1540a, second fixture 1540b, and clip 1542 preferably redirect to appliance 1500 rather than to electromagnetic radiation sensor 3000 or cannula 20 any forces due to pulling or snagging sensor cable 5000 and/or tube 32. Accordingly, in the first arrangement, electromagnetic radiation sensor 3000 may be retained in an approximately consistent positional relationship with respect to the perivascular tissue P around cannula 20 when sensing infiltration or extravasation.

Referring additionally to FIG. 13D, frame 1520 preferably is sufficiently flexible to conform to the approximate contours of epidermis E. Preferably, frame 1520 includes one or more lines of weakness 1544 disposed about frame 1520 at various positions including, for example, in the general vicinity of corners for pane 1510 and parallel to the longitudinal axis of cannula 20. According to one embodiment, individual lines of weakness 1544 preferably include living hinges or other suitable features for increasing the flexibility of frame 1520.

Appliance 1500 preferably is a single unit that includes plural location options for retaining an anatomical sensor. According to one embodiment, the anatomical sensor may include electromagnetic radiation sensor 3000 or another sensor for sensing over time a change of body structure, e.g., infiltration and extravasation. Preferably, individual fittings, e.g., first fitting 1530a or second fitting 1530b, provide alternate location options for coupling electromagnetic radiation sensor 3000 to appliance 1500. The location option that is most suitable is preferably selected based on one or more factors including: (i) location of the cannulation site N; (ii) orientation of cannula 20; (iii) avoiding movement of cannula 20 or electromagnetic radiation sensor 3000 due to pulling or snagging tubing 32 or sensor cable 5000; and (iv) comfort of the patient. Appliance 1500 is advantageous at least because the most suitable of plural location options for coupling electromagnetic radiation sensor 3000 is preferably selected.

Figure 14A:
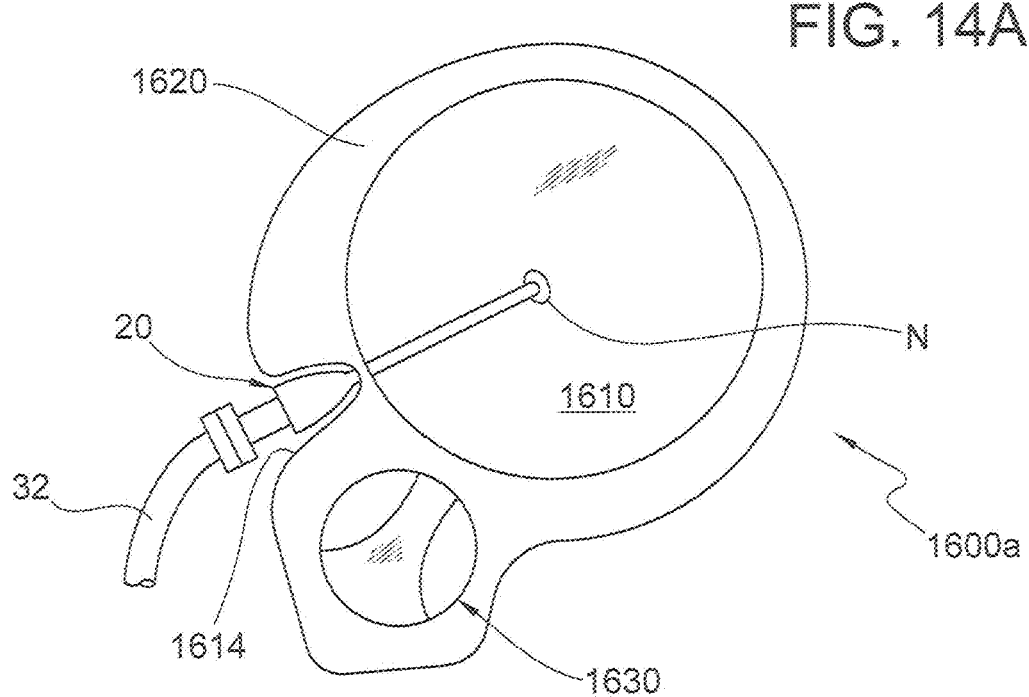
FIGS. 14A and 14B are schematic views illustrating an embodiment according to the present disclosure of a set of alternate dressing assemblies. Each assembly includes an appliance integrated with a barrier film. A cannula and a portion of an administration set are also shown.
Figure 14B:
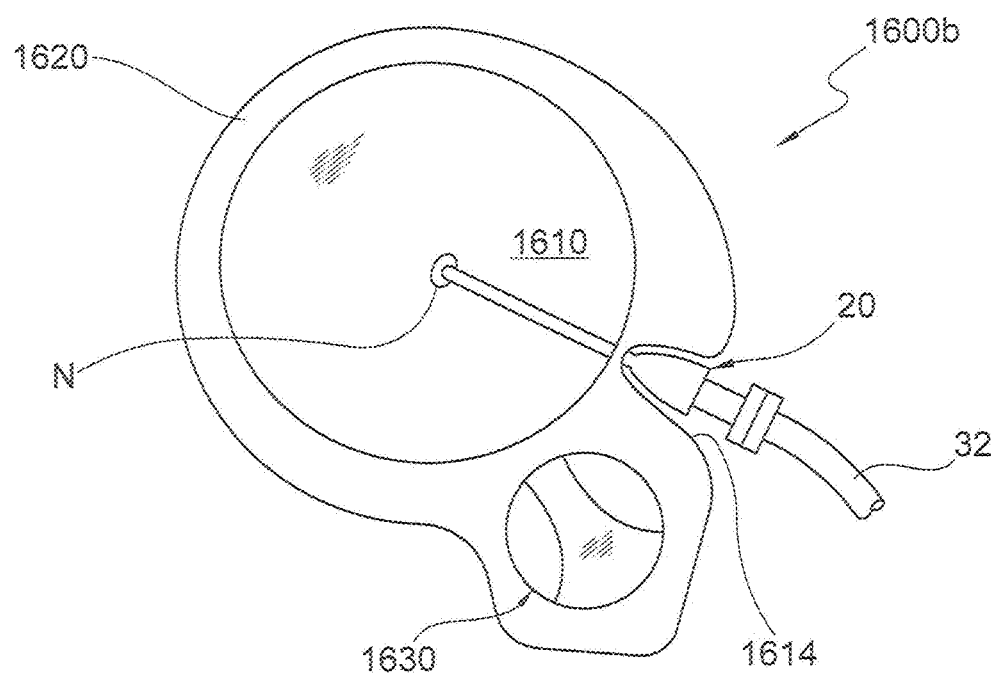

A sixth embodiment of dressing 1000 is shown in FIGS. 14A and 14B. An appliance set preferably includes (i) a contamination barrier overlying the cannulation site N; and (ii) different appliances 1600a (FIG. 14A) and 1600b (FIG. 14B) for locating electromagnetic radiation sensor 3000 (not shown in FIG. 14A or 14B) to sense if fluid is infusing the perivascular tissue P around transcutaneous sleeve 20c. As compared to appliance 1500, which includes a plurality of individual fittings at alternate location options on frame 1520, appliances 1600a and 1600b separately provide different locations for a fitting 1630 relative to a guide 1614. Accordingly, one or the other of appliances 1600a and 1600b, rather than one or the other of first and second fitting 1530a and 1530b on appliance 1500, may be selected for coupling electromagnetic radiation sensor 3000 at the most suitable location option.

Appliances 1600a and 1600b preferably each include a pane 1610, a frame 1620 and fitting 1630 that are functionally similar to, respectively, pane 1510, frame 1520 and first or second fitting 1530a and 1530b. Accordingly, appliances 1600a and 1600b preferably each provide a contamination barrier that is substantially impervious to solids, liquids, microorganisms and/or viruses, but which may be semi-permeable to allow air or vapor to pass, thus permitting the skin S underlying pane 1610 to breathe. Pane 1610 is preferably transparent or translucent to visible light for viewing the cannulation site N. Frame 1620 preferably maintains the shape of pane 1610 while appliance 1600a or appliance 1600b is laid over the cannulation site N. And a first arrangement of fitting 1630 preferably retains electromagnetic radiation sensor 3000 relative to appliance 1600a or appliance 1600b for monitoring an intravascular infusion by cannula 20, and a second arrangement of fitting 1630 preferably releases electromagnetic radiation sensor 3000 from the first arrangement.

Frame 1620 preferably has greater resistance to deformation than does pane 1610. Accordingly, frame 1620 may maintain the shape of pane 1610 while appliance 1600a or appliance 1600b is laid over the cannulation site N. According to one embodiment, frame 1620 entirely cinctures pane 1610. According to other embodiments, frame 1620 may (i) partially cincture pane 1610; (ii) extend from a peripheral portion of pane 1610 toward an interior portion of pane 1610; (iii) extend from the interior portion toward the peripheral portion; (iv) be spaced from the peripheral portion; or (v) include a combination of (i)-(iv). Frame 1620 preferably includes polyvinyl chloride, polyethylene, polypropylene, or another suitable material that is relatively rigid with respect to pane 1610. For example, frame 1620 may include a pad of polyvinyl chloride foam. Frame 1620 may be opaque, but is preferably transparent or translucent to visible light for viewing the epidermis E in the vicinity of the cannulation site N. Preferably, frame 1620 absorbs or blocks the transmission of radiation having the same wavelength(s) as emitted and collected electromagnetic radiation 3002 and 3006, e.g., near-infrared radiation. Thus, according to one embodiment, the epidermis E that underlies frame 1620 may be optically visible and shielded from ambient near-infrared radiation.

Appliance 1600*a* and appliance 1600*b* preferably are independent units that separately include different locations for retaining an anatomical sensor. Preferably, appliance 1600*a* includes fitting 1630 at a first location relative to guide 1614, e.g., on the right-hand side of guide 1614, and appliance 1600*b* includes fitting 1630 at a second location relative to guide 1614, e.g., on the left-hand side of guide 1614. Accordingly, the most suitable one of appliance 1600*a* or appliance 1600*b* preferably is selected based on one or more factors including: (i) location of the cannulation site N; (ii) orientation of cannula 20; (iii) avoiding movement of cannula 20 or electromagnetic radiation sensor 3000 due to pulling or snagging tubing 32 or sensor cable 5000; and (iv) comfort of the patient. Independent appliances 1600*a* and 1600*b* are advantageous at least because a choice is available for how an anatomical sensor, e.g., electromagnetic radiation sensor 3000, is located relative to cannula 20.

A seventh embodiment of dressing 1000 is shown in FIGS. 15A-15D. An appliance 1700 preferably includes (i) a frame 1720 that relatively positions electromagnetic radiation sensor 3000 and cannula 20; and (ii) a contamination barrier that overlies the cannulation site N and frame 1720. The contamination barrier preferably is substantially impervious to solids, liquids, microorganisms and/or viruses, and may be semipermeable to allow air or vapor to pass for permitting the skin S to breathe. The contamination barrier preferably includes a pane 1710 that is transparent or translucent to light in the visible portion of the electromagnetic spectrum for viewing the cannulation site N. Pane 1710 preferably includes a polyurethane film or another suitable material and/or construction for providing a contamination barrier that may be transparent or translucent.

An adhesive 1712 preferably bonds pane 1710 to the epidermis E (not indicated in FIGS. 15A-15D). Preferably, adhesive 1712 includes an acrylic adhesive that is suitable for contact with the epidermis E or another medical grade adhesive that is biocompatible according ISO 10993 and/or USP Class VI. Adhesive 1712 may be applied to the contamination barrier on the entire surface that confronts the epidermis E, or adhesive 1712 may be omitted from one or more portions of the surface. For example, adhesive 1712 may be omitted from a first area 1712*a* on pane 1710 in the vicinity of the cannulation site N or from a second area 1712*b* on pane 1710 preferably to facilitate pulling pane 1710 from the epidermis E. Preferably, the first or second areas 1712*a* and 1712*b* may be identified, e.g., with printing on pane 1710. Also, the strength of the bond between pane 1710 and the epidermis E may vary according to different embodiments of dressing 1700. For example, stronger or more adhesive 1712 may be used for coupling dressing 1700 to relatively robust skin, e.g., adult skin, and weaker or less adhesive 1712 may be used for coupling dressing 1700 to relatively delicate skin, e.g., pediatric skin. Preferably, a removable release liner (not shown) preserves adhesive 1712 until the contamination barrier is ready to be laid over the cannulation site N and frame 1720.

Figure 15A:
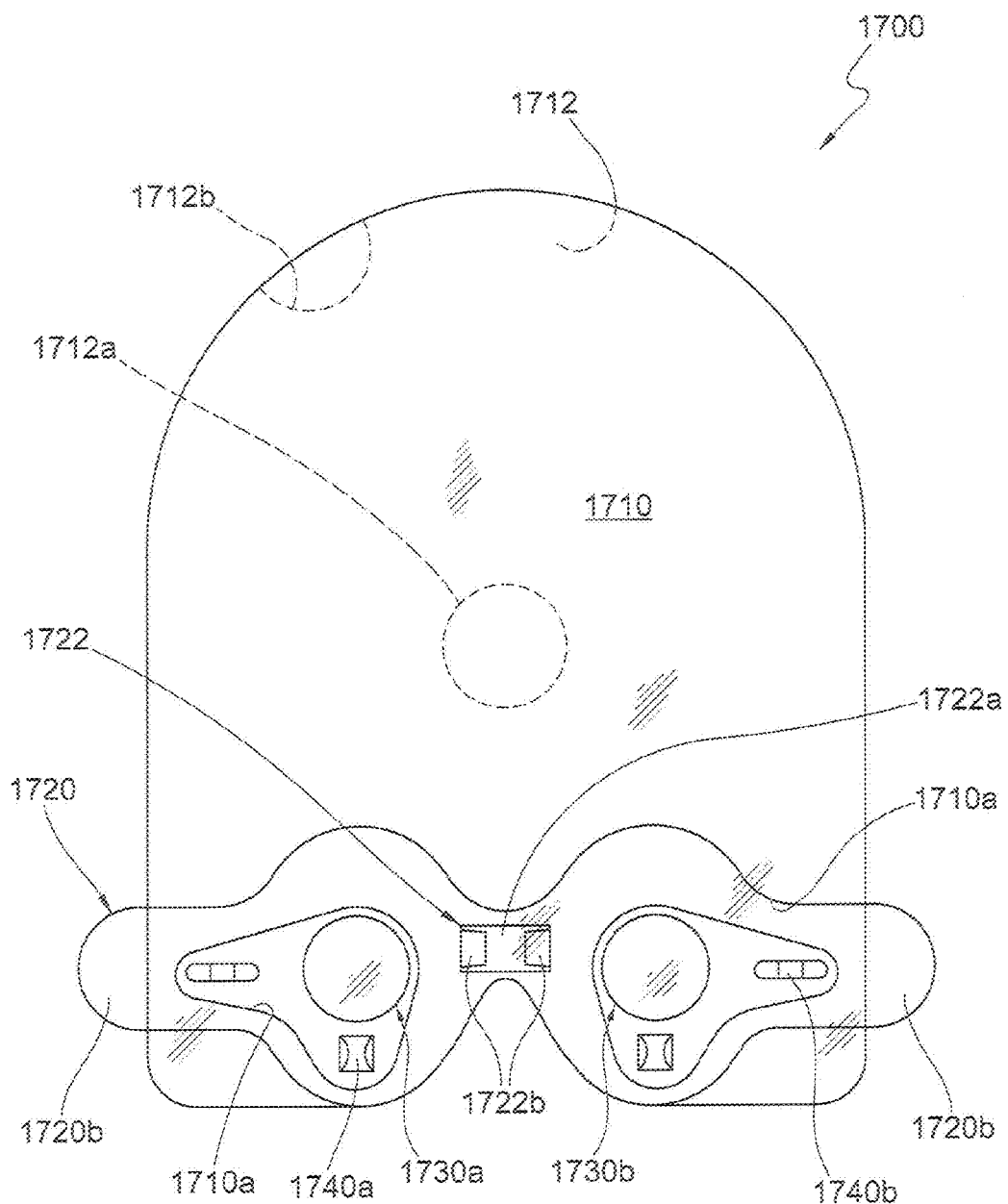
FIGS. 15A-15D illustrate an embodiment according to the present disclosure of a dressing assembly including an appliance integrated with a barrier film.
Figure 15B:
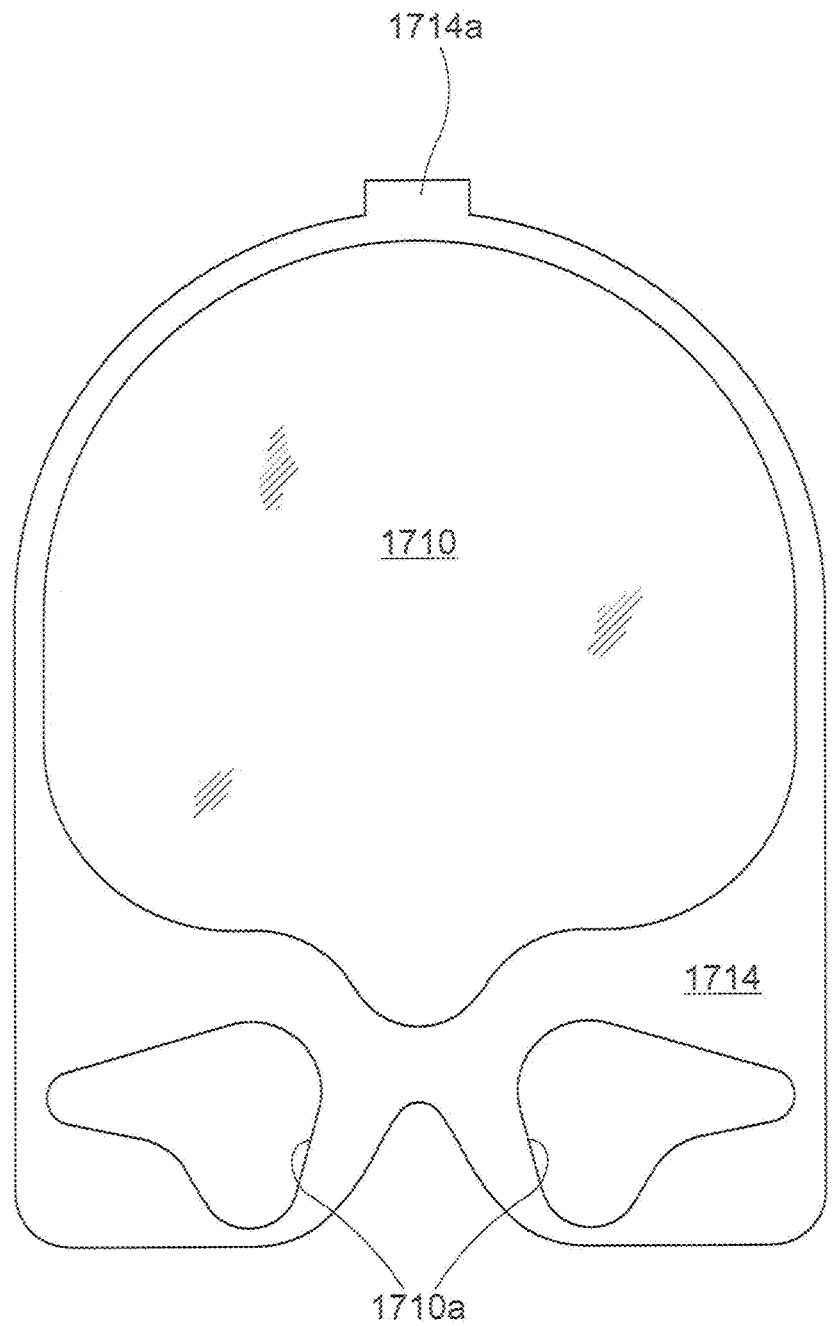
Figure 15C:
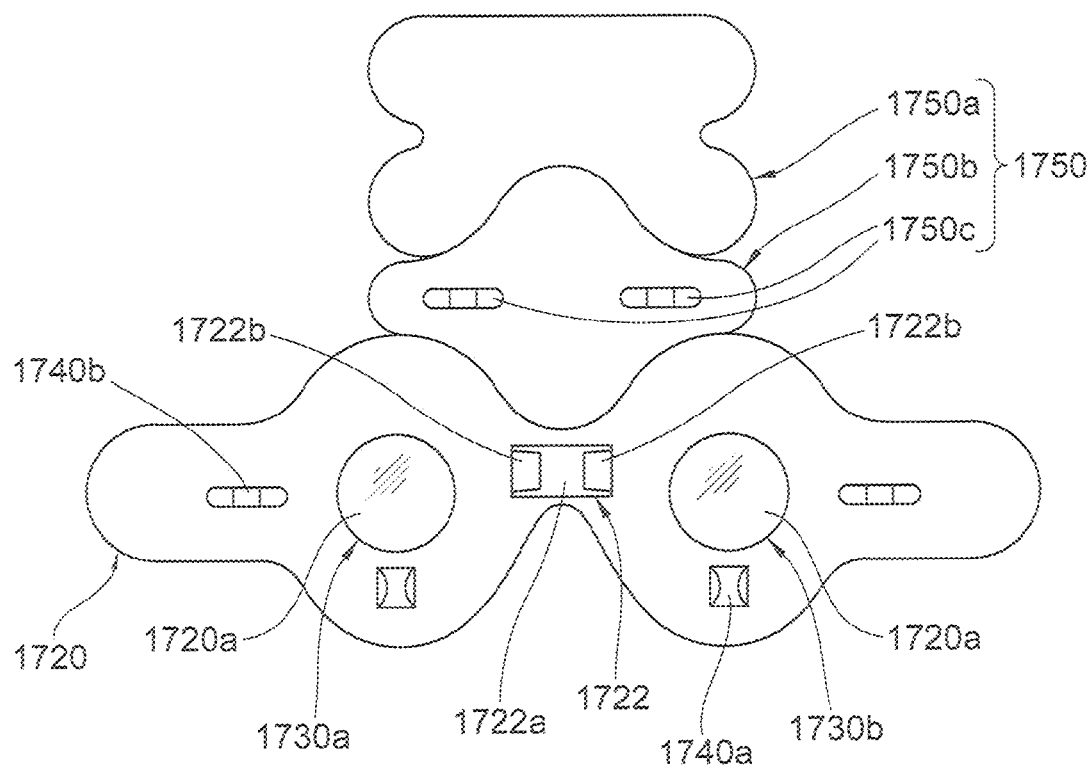
Figure 15D:
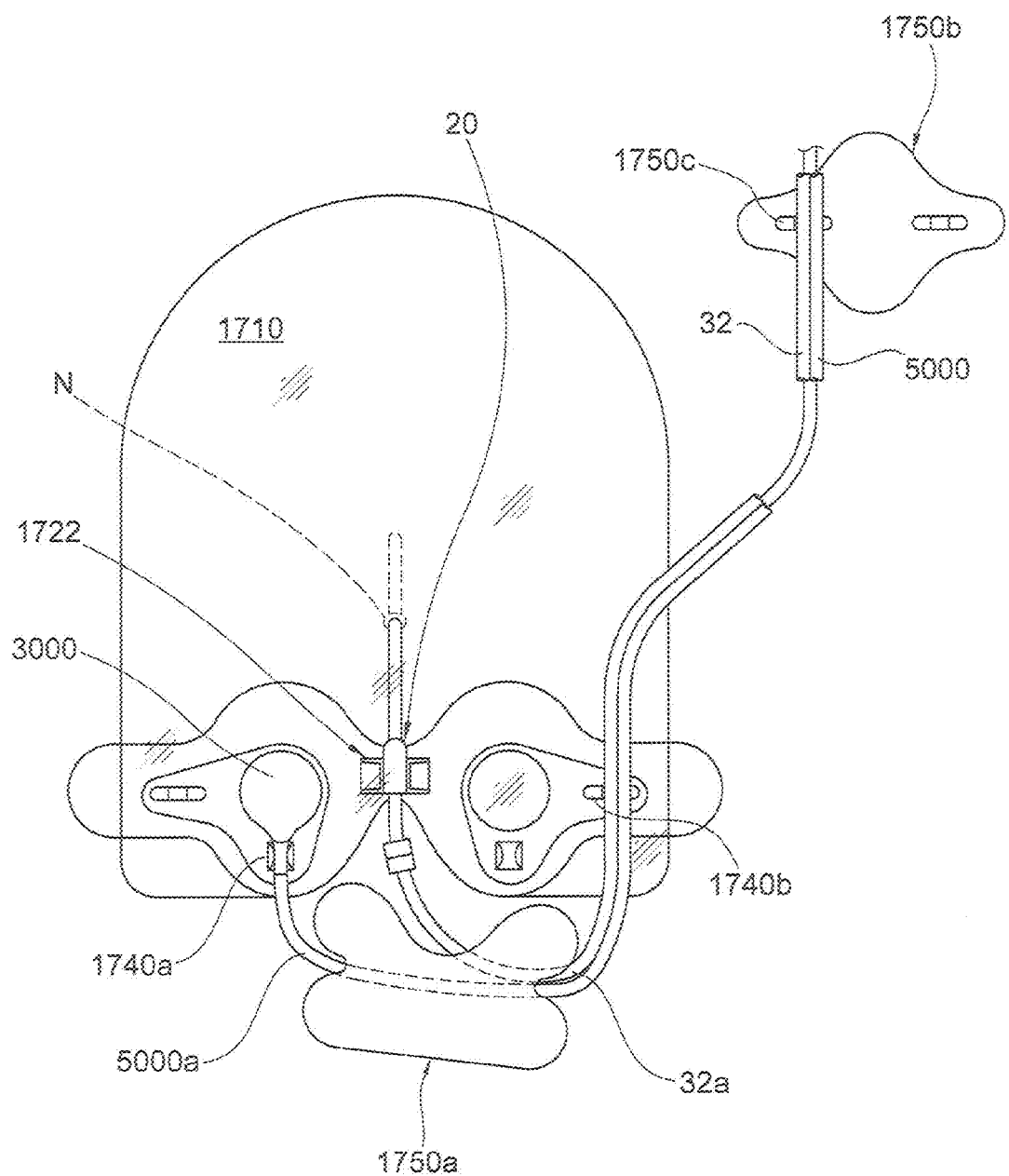

Referring particularly to FIG. 15B, a framework 1714 preferably supports pane 1710 while being laid over the cannulation site N. Preferably, framework 1714 includes paper or another suitable material that has greater resistance to deformation than does pane 1710 but is flexible enough to conform to the contours of the skin S. Accordingly, framework 1714 preferably maintains the approximate shape of the outer peripheral edge of pane 1710 and of any apertures 1710*a* (two are shown in FIGS. 15A, 15B and 15D) while the contamination barrier is being laid over the cannulation site N and frame 1720. According to one embodiment of dressing 1700, a coupling between pane 1710 and framework 1714 is preferably relatively weaker than the bond between pane 1710 and the epidermis E. Accordingly, framework 1714 may be released after pane 1710 bonds to the epidermis E. Preferably, a tab 1714*a* facilitates pulling framework 1714 from pane 1710.

Frame 1720 preferably has greater resistance to deformation than does pane 1710. Preferably, frame 1720 preferably includes polyvinyl chloride, polyethylene, polypropylene, or another suitable material that is relatively rigid with respect to pane 1710. For example, frame 1720 may include a pad of polyvinyl chloride foam. Frame 1720 preferably distributes forces, e.g., due to pulling or snagging sensor cable 5000, over an area of the skin S that is larger than that overlaid by superficies 3300 (not shown in FIGS. 15A-15D).

Frame 1720 preferably links cannula 20 and electromagnetic radiation sensor 3000. Preferably, frame 1720 includes (i) a mount 1722 for cooperatively engaging cannula 20; and (ii) at least one fitting—a first fitting 1730*a* and a second fitting 1730*b* are shown in FIGS. 15A, 15C and 15D—for coupling with electromagnetic radiation sensor 3000. Accordingly, frame 1720 preferably includes a link for establishing and maintaining a positional relationship between cannula 20 and electromagnetic radiation sensor 3000. According to one embodiment, mount 1722 preferably includes a base 1722*a* and one or more resilient projections 1722*b* extending from base 1722*a*. Preferably, base 1722*a* includes an interface for coupling mount 1722 with frame 1720, e.g., via an adhesive, and projection(s) 1722*b* resiliently capture a portion of cannula 20. Therefore, mount 1722 preferably establishes and maintains a positional relationship between cannula 20 and frame 1720. Preferably, individual fittings, e.g., first fitting 1730*a* or second fitting 1730*b*, may be comparable to fittings 1110, 1210, 1310, 1430 or 1530*a*/1530*b* discussed above and therefore each may retain electromagnetic radiation sensor 3000. Therefore, each individual fitting preferably establishes and maintains a positional relationship between electromagnetic radiation sensor 3000 and frame 1720. Thus, according to one embodiment, frame 1720, mount 1722, and first fitting 1730*a* or second fitting 1730*b* preferably link cannula 20 and electromagnetic radiation sensor 3000 by establishing and maintaining their relative positional relationship.

Referring particularly to FIG. 15C, frame 1720 preferably prevents contiguous engagement between electromagnetic radiation sensor 3000 and the epidermis E. Preferably, a barrier layer 1720*a* extends across the pocket of individual fittings, e.g., first fitting 1730*a* and second fitting 1730*b*, and is interposed between superficies 3300 and the epidermis E in the first arrangements of individual fittings 1730*a* or 1730*b*. Barrier layer 1720*a* may be the same material as pane 1710 or another material that is substantially impervious to solids, liquids, microorganisms and/or viruses, and substantially transparent to emitted and collected electromagnetic radiation 3002 and 3006.

Strain relief devices preferably redirect forces from electromagnetic radiation sensor 3000 to dressing 1700. Preferably, individual fittings, e.g., first fitting 1730*a* or second fitting 1730*b*, each include a set of strain relief devices that contiguously engage sensor cable 5000 in the first arrangement. According to one embodiment, each set of strain relief devices preferably includes a first fixture 1740a and a second fixture 1740b. Individual fixtures 1740a or 1740b preferably each include a plurality of posts separated by a gap that is smaller than the diameter of sensor cable 5000 and/or the diameter of tubing 32. Accordingly, sensor cable 5000 and/or tubing 32 may be retained by a resilient interference fit between a pair of posts that preferably limit lateral and/or longitudinal movement of sensor cable 5000 or tubing 32 relative to frame 1720.

Preferably, first and second fixtures 1740a and 1740b are disposed on opposite sides of mount 1722. Each of FIGS. 15A, 15C and 15D indicate only one of two pairs of fixtures that are shown. In the first arrangement, first fixture 1740a preferably retains sensor cable 5000 proximate a first one of the first and second fittings 1730a and 1730b, and second fixture 1740b preferably retains sensor cable 5000 and tubing 32 proximate a second one of the first and second fittings 1730a and 1730b. First fixture 1740a of first fitting 1730a is shown on the left-hand side of mount 1722 as viewed in FIG. 15D and second fixture 1740b of first fitting 1730a is shown on the right-hand side of mount 1722 as viewed in FIG. 15D. According to one embodiment, first fixture 1740a preferably cooperates with sensor cable 5000 to eliminate or at least minimize rotation of electromagnetic radiation sensor 3000 with respect to first fitting 1730a, and second fixture 1740b preferably establishes first bight 5000a and second bight 32a for sensor cable 5000 and tubing 32, respectively.

A method of implementing dressing 1700 will now be discussed with reference to FIG. 15D. Cannula 20 is inserted at cannulation site N in a typical manner. Preferably, frame 1720 is bonded to the epidermis E (not indicated) with projection(s) 1722b of mount 1722 engaging a portion of cannula 20. Pane 1710 and framework 1714 preferably are overlaid on frame 1720 with apertures 1710a cincturing first fitting 1730a, second fitting 1730b, and first and second fixtures 1740a and 1740b. Preferably, adhesive 1712 bonds pane 1710 to the epidermis E, and framework 1714 is separated from pane 1710. Adhesive 1712 preferably also adheres pane 1710 over the portion of cannula 20 that is engaged by mount 1722 so that cannula 20 is coupled to frame 1720. Tubing 32 is coupled with cannula 20 in a typical manner and preferably also engages second fixture 1740b to form second bight 32a. Preferably, electromagnetic radiation sensor 3000 is coupled to an individual fitting, e.g., the fitting on the left-hand side of mount 1722 as viewed in FIG. 15D, with sensor cable 5000 engaging first fixture 1740a. Sensor cable 5000 preferably also engages second fixture 1740b to form first bight 5000a. Electromagnetic radiation sensor 3000 is thereby coupled to frame 1720. Preferably, a lead management system 1750 limits the forces that may be transmitted to dressing 1700 as a result of pulling or snagging tubing 32 or sensor cable 5000. Lead management system 1750 preferably bonds to the epidermis E, e.g., with an adhesive, and includes a patch 1750a and a board 1750b. According to one embodiment, patch 1750a preferably is shaped and sized to overlay first and second bights 5000a and 32a, and board 1750b preferably includes at least one fixture 1750c that is similar to second fixture 1740b in construction and function. Preferably, board 1750b is spaced from first and second bights 5000a and 32a along the lengths of tubing 32 and sensor cable 5000. According to one embodiment, frame 1720, patch 1750a and board 1750b preferably share a similar construction and may be manufactured concurrently as a unit, which may then be separated when implementing dressing 1700.

Removing dressing 1700 preferably occurs after releasing electromagnetic radiation sensor 3000 from one of the first and second fittings 1730a and 1730b. Preferably, pane 1710 is peeled off beginning with second area 1712b while wings 1720b (two are indicated on FIG. 15A) are held to separate pane 1710 from frame 1720. Cannula 20 preferably is disengaged from mount 1722 and extracted from the cannulation site N, and frame 1720 is peeled off the epidermis E. A barrier film such as Cavilon™, manufactured by 3M (St. Paul, Minn., USA), or another topical agent may be used when implementing dressing 1700 for protecting the epidermis E from adhesive trauma due to peeling off pane 1710 and/or frame 1720.

Dressing 1700 is advantageous at least because there is a link between cannula 20 and electromagnetic radiation sensor 3000 when sensing if fluid is infusing the perivascular tissue P around transcutaneous sleeve 20c. Preferably, frame 1720, mount 1722, and individual fittings, e.g., first fitting 1730a or second fitting 1730b, establish and maintain a relative positional relationship that links cannula 20 and electromagnetic radiation sensor 3000. Dressing 1700 is also advantageous because a contamination barrier is implemented in a typical manner, e.g., overlying the cannulation site N, and concurrently cooperates with the link between cannula 20 and electromagnetic radiation sensor 3000.

An eighth embodiment of dressing 1000 is shown in FIGS. 16A-16D. Appliances 1800a and 1800b preferably include (i) a contamination barrier that overlies the cannulation site N (not shown in FIGS. 16A-16D); (ii) a molded frame that locates electromagnetic radiation sensor 3000 (not shown in FIGS. 16A-16D) to sense if fluid is infusing the perivascular tissue P around transcutaneous sleeve 20c; and (iii) a plurality of options for relatively locating electromagnetic radiation sensor 3000 and cannula 20 (not shown in FIGS. 16A-16D). According to one embodiment, pane 1810 includes a contamination barrier that preferably is substantially impervious to solids, liquids, microorganisms and/or viruses, and may be semi-permeable to allow air or vapor to pass for permitting the skin S to breathe. Preferably, appliance 1800a (FIGS. 16A and 16B) includes a first frame 1820a that is integrally molded with a first fitting 1830a, and appliance 1800b (FIGS. 16C and 16D) includes a second frame 1820b over-molding a second fitting 1830b.

Employing molding to manufacture appliances 1800a and 1800b preferably reduces the number of independent components included in appliances 1800a and 1800b as compared to, for example, appliances 1400, 1500, 1600a/1600b and 1700. Preferably, the phrase "independent component" as it is used herein refers to a single part that (a) has a substantially uniform composition; and (b) is coupled with other parts in an assemblage. Appliance 1800a preferably reduces the number of independent components by at least two as compared to, for example, appliances 1400, 1500, 1600a/1600b and 1700 because (i) first frame 1820a and first fitting 1830a may be formed as a single independent component, e.g., integrally molded with a homogeneous chemical compound, before assembling appliance 1800a; and (ii) an adhesive for coupling first frame 1820a with first fitting 1830a may be eliminated. Appliance 1800b preferably reduces the number of independent components by at least one as compared to, for example, appliances 1400, 1500, 1600a/1600b and 1700 because an adhesive for coupling first frame 1820a with first fitting 1830a is eliminated. Preferably, further reductions are possible in the number of independent components included in appliances 1800a and 1800b as compared to appliances 1500 or 1700. For example, as compared to appliances 1500 and 1700, a further reduction of at least one additional independent component may be possible because first or second frames 1820a or 1820b and strain relief device(s) for sensor cable 5000 may be formed as a single independent component, e.g., integrally molded with a homogeneous chemical compound, before assembling appliance 1800a or 1800b. And as compared to appliance 1700, a yet further reduction of at least two additional independent components may be possible because (i) first or second frames 1820a or 1820b and a mount for cannula 20 may be formed as a single independent component, e.g., integrally molded with a homogeneous chemical compound, before assembling the dressing; and (ii) an adhesive for coupling the mount with first or second frames 1820a or 1820b may be eliminated. Thus, employing molding may reduce the number of independent components that preferably are included in appliances 1800a and 1800b.

Appliance 1800a (or appliance 1800b) preferably includes a pane 1810, frame 1820a (or frame 1820b), and fitting 1830a (or fitting 1830b) that function similar to, for example, pane 1610, frame 1620 and fitting 1630, respectively. Accordingly, pane 1810 preferably is transparent or translucent to visible light for viewing the cannulation site N; frame 1820a (or frame 1820b) preferably maintains the shape of pane 1810 while appliance 1800a (or appliance 1800b) is laid over the cannulation site N; and a first arrangement of fitting 1830a (or fitting 1830b) preferably retains electromagnetic radiation sensor 3000 relative to appliance 1800a (or appliance 1800b) for monitoring an intravascular infusion by cannula 20 and a second arrangement of fitting 1830a (or fitting 1830b) preferably releases electromagnetic radiation sensor 3000 from the first arrangement.

Pane 1810 preferably uses an adhesive 1812 to bond with the epidermis E in the vicinity of the cannulation site N. Preferably, pane 1810 includes a polyurethane film or another suitable material for providing a contamination barrier that may be transparent or translucent. Adhesive 1812 preferably couples pane 1810 to the epidermis E. Preferably, adhesive 1812 includes an acrylic adhesive that is suitable for contact with the epidermis E or another medical grade adhesive that is biocompatible according ISO 10993 and/or USP Class VI. Adhesive 1812 may be applied to pane 1810 on the entire surface that confronts the epidermis E, or adhesive 1812 may be omitted from one or more portions of the surface. Also, the strength of the bond between pane 1810 and the epidermis E may vary according to different embodiments of the dressing. For example, stronger or more adhesive 1812 may be used for coupling appliance 1800a or appliance 1800b to relatively robust skin and weaker or less adhesive 1812 may be used for coupling appliance 1800a or appliance 1800b to relatively delicate skin.

Appliances 1800a and 1800b each preferably include a plurality of options for positioning or orienting the appliances on the skin S. Preferably, appliance 1800a includes a first guide 1814a at a first location relative to fitting 1830a, e.g., on the right-hand side of fitting 1830a as viewed in FIG. 16A, and a second guide 1814b at a second location relative to fitting 1830a, e.g., on the left-hand side of fitting 1830a as viewed in FIG. 16A. Similarly, appliance 1800b includes first guide 1814a located on the right-hand side of fitting 1830b as viewed in FIG. 16C, and second guide 1814b located on the left-hand side of fitting 1830b as viewed in FIG. 16C. The most suitable one of first guide 1814a or second guide 1814b preferably is selected based on one or more factors including: (i) location of the cannulation site N; (ii) orientation of cannula 20; (iii) avoiding movement of cannula 20 or electromagnetic radiation sensor 3000 due to pulling or snagging tubing 32 or sensor cable 5000; and (iv) comfort of the patient. According to one embodiment, individual guides 1814a and 1814b preferably include a notch or some other feature of appliance 1800a or 1800b that may be sized or shaped to receive a portion of cannula 20. According to another embodiment, individual guides 1814a and 1814b preferably include a mount (not shown) for cooperatively engaging cannula 20. Alternate first and second guides 1814a and 1814b are advantageous at least because a choice is available for how electromagnetic radiation sensor 3000 is located relative to cannula 20.

First and second frames 1820a and 1820b preferably have greater resistance to deformation than does pane 1810. Accordingly, individual frames, e.g., first frame 1820a or second frame 1820b, may maintain the shape of pane 1810 while appliance 1800a or appliance 1800b is laid over the cannulation site N. First and second frames 1820a and 1820b preferably are formed as single independent components, e.g., integrally molded with a homogenous chemical compound, rather than being built-up as a laminate. Preferably, individual frames, e.g., first frame 1820a or second frame 1820b, include polydimethylsiloxanes or another suitable material for molding the frames. Advantageously, appliances 1800a and 800b preferably resist absorbing fluids as compared to typical woven or fabric dressings.

First and second fittings 1830a and 1830b preferably are capable of retaining electromagnetic radiation sensor 3000. Preferably, individual fittings, e.g., first fitting 1830a or second fitting 1830b, each include a pocket 1832, a wall 1834, and a tab 1836. Pocket 1832 preferably receives electromagnetic radiation sensor 3000 (not shown in FIGS. 16A-16D) in the first arrangement. Preferably, pane 1810 extends across pocket 1832 and is interposed between superficies 3300 and the epidermis E in the first arrangement of the individual fittings. According to one embodiment, wall 1834 preferably includes a plurality of individual segments disposed partially around pocket 1832. Preferably, at least one tab 1836 projects from wall 1834 and overlies a portion of electromagnetic radiation sensor 3000 in the first arrangement. Elastic deformation of wall 1834 or tab 1836 preferably permits electromagnetic radiation sensor 3000 to snap-in to pocket 1832 in the first arrangement and to snap-out from pocket 1832 in the second arrangement. According to one embodiment, tab 1836 preferably biases superficies 3300 toward the skin S by contiguously engaging electromagnetic radiation sensor 3000 in the first arrangement. According to other embodiments, individual fittings may include a latch, a cap, a resilient element, or another suitable device which, in the first arrangement, retains electromagnetic radiation sensor 3000 in pocket 1832 and preferably biases superficies 3300 toward the epidermis E, and in the second arrangement, releases electromagnetic radiation sensor 3000 from the first arrangement so as to permit movement out of pocket 1832.

Appliances 1800a and 1800b preferably maintain an approximately consistent positional relationship between electromagnetic radiation sensor 3000 and the perivascular tissue P. According to an embodiment of appliance 1800a, frame 1820a preferably distributes forces acting on electromagnetic radiation sensor 3000 due to, e.g., pulling or snagging sensor cable 5000, over an area of the skin S that is larger than that overlaid by superficies 3300. Preferably, one or more arms 1838 (four are shown in FIG. 16C) are coupled with wall 1834 according to an embodiment of appliance 1800b. Arm(s) 1838 preferably extend away from pocket 1832, e.g., beyond an area of the skin S that is overlaid by superficies 3300 in the first arrangement of fitting 1830b. Accordingly, forces acting on electromagnetic radiation sensor 3000 due to, e.g., pulling or snagging sensor cable 5000, may be distributed by arm(s) 1838 and frame 1820b over an area of the skin S that is larger than that overlaid by superficies 3300. Appliances 1800a and 1800b therefore preferably enhance an approximately consistent positional relationship between electromagnetic radiation sensor 3000 and the perivascular tissue P when sensing infiltration or extravasation.

Strain relief devices preferably redirect forces from sensor cable 5000 to appliance 1800a or appliance 1800b. Preferably, first frame 1820a or second fitting 1830b include at least one strain relief device that contiguously engages sensor cable 5000 in the first arrangement. First frame 1820a and a strain relief device 1840 (FIGS. 16A and 16B) preferably are formed as a single independent component, e.g., integrally molded with a homogeneous chemical compound, before assembling appliance 1800a. Second fitting 1830b and first and second fixtures 1840a and 1840b (FIGS. 16C and 16D) preferably are formed as a single independent component, e.g., integrally molded with a homogeneous chemical compound, before assembling appliance 1800b. According to an embodiment of appliance 1800b, portions of first and second fixtures 1840a and 1840b preferably are exposed with respect to frame 1820b. Preferably, strain relief device 1840, first fixture 1840a, and second fixture 1840b each include a plurality of posts separated by a gap that is smaller than the diameter of sensor cable 5000. Accordingly, sensor cable 5000 may be retained by a resilient interference fit between a pair of posts that preferably limit lateral and/or longitudinal movement of sensor cable 5000 relative to frame 1820a or frame 1820b.

Molding during manufacturing of appliance 1800a and 1800b preferably includes at least one of (i) integrally molding a single independent component that fulfills more than one role in an assemblage; or (ii) over-molding a first independent component with another independent component in an assemblage. Preferably, first frame 1820a is integrally molded with wall 1834 and tab 1836 as an independent component included in appliance 1800a. Roles including maintaining the shape of pane 1810 and retaining/releasing electromagnetic radiation sensor 3000 are therefore fulfilled by a single independent component in appliance 1800a. According to an embodiment of appliance 1800a, strain relief device 1840 preferably also is integrally molded with first frame 1820a as an independent component included in appliance 1800a. Accordingly, the additional role of limiting relative movement of sensor cable 5000 is also fulfilled by a single independent component in appliance 1800a. According to an embodiment of appliance 1800b, preferably an initial shot in a multi-shot mold forms a first independent component and a subsequent shot in the multi-shot mold assembles appliance 1800b, including the independent component formed with the initial shot. Preferably, second frame 1820b over-molds second fitting 1830b in appliance 1800b. For example, wall 1834 and tab 1836 preferably are integrally molded with second fitting 1830b as an independent component before being over-molded with second frame 1820b. According to embodiments of appliance 1800b, first fixture 1840a and/or second fixture 1840b preferably also are integrally molded with second fitting 1830b as an independent component before being over-molded with second frame 1820b. Employing molding in manufacturing appliances 1800a and 1800b is advantageous at least because fewer independent components are preferably assembled as compared to, for example, appliances 1400, 1500, 1600a/1600b and 1700.

Sensor

Figure 17:
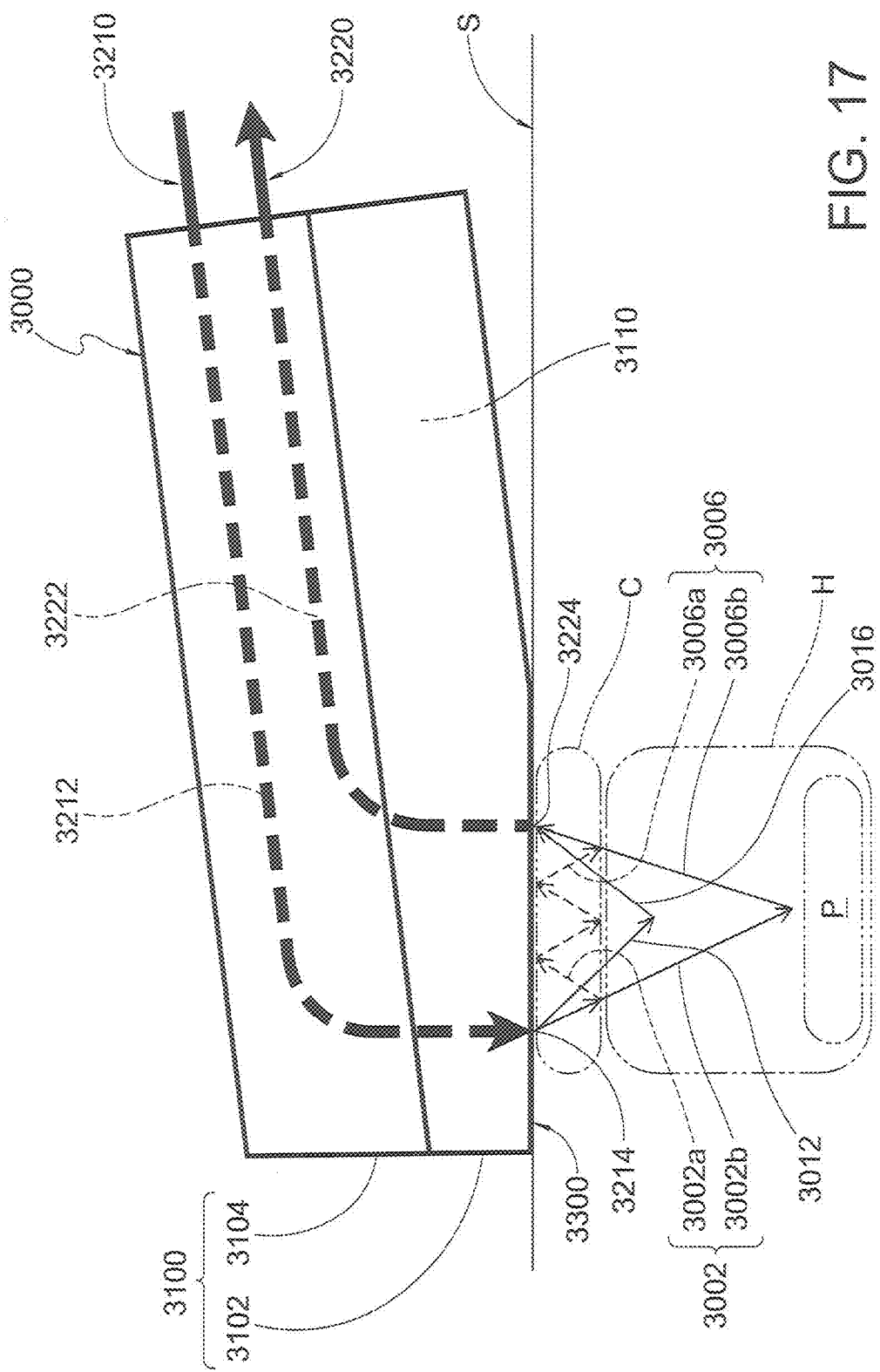
FIG. 17 is a schematic view illustrating an electromagnetic radiation sensor according to the present disclosure. The electromagnetic radiation sensor is shown contiguously engaging Animalia skin.

FIG. 17 shows an embodiment according to the present disclosure of the electromagnetic radiation sensor 3000 that preferably includes an anatomic sensor. As the terminology is used herein, "anatomic" preferably refers to the structure of an Animalia body and an "anatomic sensor" preferably is concerned with sensing a change over time of the structure of the Animalia body. By comparison, a physiological sensor is concerned with sensing the functions or activities of an Animalia body, e.g., pulse or blood chemistry, at a point in time.

The electromagnetic radiation signals emitted by electromagnetic radiation sensor 3000 preferably are not harmful to an Animalia body. According to one embodiment, electromagnetic radiation sensor 3000 preferably emits electromagnetic radiation signals at wavelengths in the visible light or infrared radiation portions of the electromagnetic spectrum. Preferably, electromagnetic radiation sensor 3000 emits wavelengths in a range between approximately 380 nanometers and approximately 1 millimeter. These wavelengths generally correspond to a frequency range of approximately 790 terahertz to approximately 300 gigahertz. According to other embodiments, electromagnetic radiation sensor 3000 may emit electromagnetic radiation signals in shorter wavelength portions of the electromagnetic spectrum, e.g., ultraviolet light, X-rays or gamma rays, preferably when radiation power and/or signal duration are such that tissue harm is minimized.

Electromagnetic radiation sensor 3000 preferably aids in diagnosing infiltration or extravasation. Preferably, first electromagnetic radiation 3002 is emitted via superficies 3300 of electromagnetic radiation sensor 3000 and first electromagnetic radiation 3006 is collected via superficies 3300. First emitted electromagnetic radiation 3002 preferably includes (i) cutaneous electromagnetic radiation 3002a that minimally penetrates the skin S; and (ii) transcutaneous electromagnetic radiation 3002b that passes through the target area of the skin S into the perivascular tissue P. The perivascular tissue P in the vicinity of blood vessel V preferably includes the cells or compartments that may become unintentionally infused, e.g., infiltrated or extravasated by fluid exiting from cannula 20. First collected electromagnetic radiation 3006 preferably includes (i) a noise component 3006a due at least in part to cutaneous electromagnetic radiation 3002a; and (ii) a signal component 3006b that is a portion of transcutaneous electromagnetic radiation 3002b that is at least one of specularly reflected, diffusely reflected (e.g., due to elastic or inelastic scattering), fluoresced (e.g., due to endogenous or exogenous factors), or otherwise redirected from the perivascular tissue P before passing through the skin S.

The wavelength of first emitted electromagnetic radiation 3002 preferably is longer than approximately 750 nanometers. The frequency of first emitted electromagnetic radiation 3002 therefore is no more than approximately 400 terahertz. According to one embodiment, first emitted electromagnetic radiation 3002 preferably is in the near-infrared radiation portion of the electromagnetic spectrum. As the terminology is used herein, "near-infrared" preferably refers to electromagnetic radiation having wavelengths between approximately 750 nanometers and approximately 2,100 nanometers. These wavelengths generally correspond to a frequency range of approximately 400 terahertz to approximately 145 terahertz. A desirable range in the near-infrared portion of the electromagnetic spectrum preferably includes wavelengths between approximately 800 nanometers and approximately 1,050 nanometers. These wavelengths generally correspond to a frequency range of approximately 375 terahertz to approximately 285 terahertz.

First emitted and collected electromagnetic radiation 3002 and 3006 preferably share one or more wavelengths. According to one embodiment, first emitted and collected electromagnetic radiation 3002 and 3006 preferably share a single peak wavelength, e.g., approximately 940 nanometers (approximately 320 terahertz). As the terminology is used herein, "peak wavelength" preferably refers to an interval of wavelengths including a spectral line of peak power. The interval preferably includes wavelengths having at least half of the peak power. Preferably, the wavelength interval is +/− approximately 20 nanometers with respect to the spectral line. According to other embodiments, first emitted and collected electromagnetic radiation 3002 and 3006 preferably share a plurality of peak wavelengths, e.g., approximately 940 nanometers and approximately 1,050 nanometers. According to other embodiments, a first one of first emitted and collected electromagnetic radiation 3002 and 3006 preferably spans a first range of wavelengths, e.g., from approximately 700 nanometers to approximately 1000 nanometers. This wavelength range generally corresponds to a frequency range from approximately 430 terahertz to approximately 300 terahertz. A second one of first emitted and collected electromagnetic radiation 3002 and 3006 preferably shares with the first range a single peak wavelength, a plurality of peak wavelengths, or a second range of wavelengths. Preferably, patient monitoring device 6000 performs an electromagnetic radiation power analysis at the wavelength(s) shared by first emitted and collected electromagnetic radiation 3002 and 3006 for indicating an anatomical change over time in the perivascular tissue P.

The inventors discovered a problem regarding accurately alerting a healthcare giver to perform an infiltration/extravasation examination. The examination that healthcare givers perform typically includes palpating the skin S in the vicinity of the target area, observing the skin S in the vicinity of the target area, and/or comparing limbs that include and do not include the target area of the skin S. Typically, the object of the examination is to identify, for example, (i) edema, pain or numbness in the vicinity of the cannulation site N; (ii) blanching, discoloration, inflammation or coolness of the skin S in the vicinity of the cannulation site N; (iii) breakdown, tautness or stretching of the skin S; or (iv) drainage from the cannulation site N. False alerts to perform an infiltration/extravasation examination may distract healthcare givers or reduce confidence in the alerting system. The inventors further discovered, inter alia, the problem is first collected electromagnetic radiation 3006 may not accurately alert healthcare givers to perform an infiltration/extravasation examination.

An Animalia body typically includes macrovascular and microvascular systems for circulating blood between the heart and tissues. Typically, the macrovascular system includes the relatively large (approximately 1.0-10.0 millimeter diameter) arteries and veins that deliver and return blood with respect to the heart, and the microvascular system includes the relatively small blood vessels that are embedded within the tissues. The microvascular system typically includes arterioles (approximately 0.1 millimeter diameter), capillaries (approximately 0.01 millimeter diameter), and venules (approximately 0.1 millimeter diameter). Preferably, the arterioles carry blood from arteries to capillaries and the venules carry blood from capillaries to veins.

Tissue blood perfusion is a physiological function that typically is regulated by the microvascular system. As the terminology is used herein, "blood perfusion" preferably refers to a delivery process that includes (i) transporting nutrients, e.g., oxygen, to capillaries; (ii) exchanging the nutrients and waste, e.g., carbon dioxide, through the capillaries between blood and interstitial fluid; and (iii) transporting the waste from the capillaries. Typically, tissue blood perfusion is evaluated based on blood flow per unit volume of tissue, e.g., (milliliters/minute)$_{blood}$/milliliter$_{tissue}$, or blood flow per unit mass of tissue, e.g., (milliliters/minute)$_{blood}$/gram$_{tissue}$. Body temperature and blood pressure are additional examples of physiological functions that typically are at least partially regulated by the microvascular system.

The microvascular system typically includes pre-capillary and post-capillary regulators for tissue blood perfusion. Typically, pre-capillary regulation includes modulating blood flow entering the capillaries and venules by contracting and relaxing pre-capillary sphincters and smooth muscles on the walls of the arterioles. Post-capillary regulation typically includes microscopic venous valves that restrict blood flow from post-capillary venules back into capillaries.

Figure 34C:
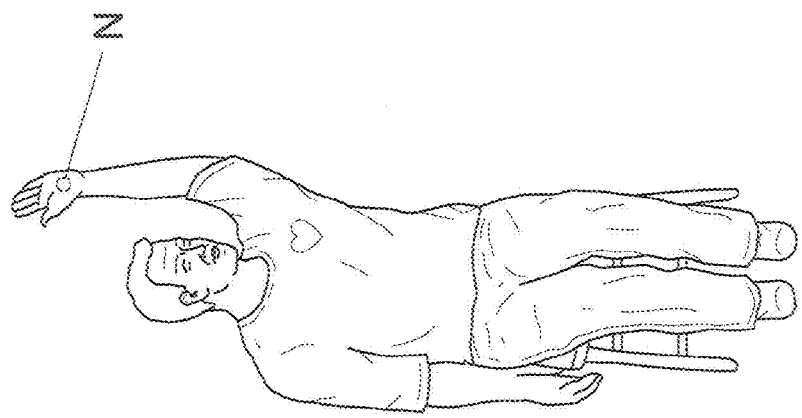
FIGS. 34A-34C are schematic views illustrating level, dependency and elevation relative to a patient's heart of the cannulation site shown in FIG. 33A.
Figure 34B:
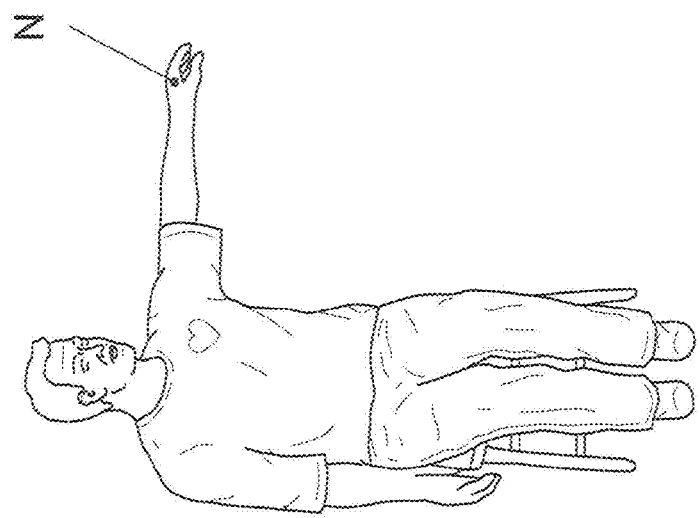
Figure 34A:
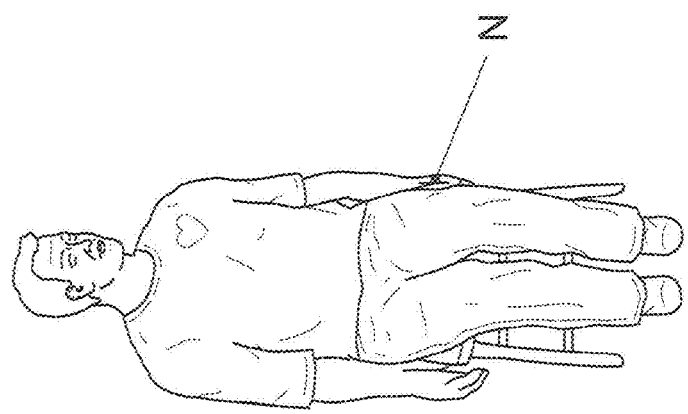

A posture change of an Animalia body typically elicits a vascular response including the microvascular system regulating tissue blood perfusion. As the terminology is used herein, "posture change" preferably refers to the result of actions or activities that modify the elevation of the cannulation site N relative to a patient's heart. Typically, posture changes include raising or lowering a limb. FIG. 34A schematically illustrates a first posture with preferably nominal tissue blood perfusion because the cannulation site N is relatively level with respect to the heart. FIG. 34B schematically illustrates a second posture with the cannulation site N relatively dependent with respect to the heart. Typically, the tissue blood perfusion in the second posture increases relative to the nominal tissue blood perfusion in the first posture because the microscopic venous valves preferably are at least partially inverted such that flow from post-capillary venules back into capillaries is less restricted. Accordingly, there preferably is an increased volume of blood in the microvascular system in the second posture as compared with the first posture. FIG. 34C schematically illustrates a third posture with the cannulation site N relatively elevated with respect to the heart. Typically, the tissue blood perfusion in the third posture decreases relative to the nominal tissue blood perfusion in the first posture because the pre-capillary sphincters and smooth muscles on the walls of the arterioles are less effective modulating blood flow against gravity. Accordingly, there preferably is a decreased volume of blood in the microvascular system in the third posture as compared with the first posture The inventors discovered a source of the problem regarding accurately alerting a healthcare giver to perform an infiltration/extravasation examination is changing tissue blood volume affects the propagation of first emitted and collected electromagnetic radiation 3002 and 3006. As the terminology is used herein, "tissue blood volume" preferably refers to a volume of blood along a monitoring path of sensor 3000, and "monitoring path" preferably refers to a volume of tissue in which first emitted and collected electromagnetic radiation 3002 and 3006 propagate. Thus, tissue blood volume preferably is a measure of blood concentration in tissue. The inventors further discovered, inter alia, tissue blood volume is affected by patient posture changes. Typically, lowering the cannulation site N, e.g., changing posture from the first posture (FIG. 34A) to the second posture (FIG. 34B), increases the tissue blood volume and raising the cannulation site N, e.g., changing posture from the first posture (FIG. 34A) to the third posture (FIG. 34C), decreases the tissue blood volume. The inventors further discovered, inter alia, tissue blood volume changes along the monitoring path of sensor 3000 affect the propagation of first emitted and collected electromagnetic radiation 3002 and 3006 such that first collected electromagnetic radiation 3006 responds to tissue blood volume changes as well as to infiltration/extravasation events. Thus, the inventors discovered, inter alia, that tissue blood volume changes due to patient posture changes might falsely alert healthcare givers to perform an infiltration/extravasation examination.

Electromagnetic radiation sensor 3000 preferably mitigates false alerts caused by tissue blood volume changes.

Preferably, a second wavelength is used to determine the accuracy of an alert to perform an infiltration/extravasation examination by distinguishing between tissue blood volume changes and infiltration/extravasation events. According to one embodiment, a second electromagnetic radiation 3012 is emitted via superficies 3300 of electromagnetic radiation sensor 3000 and a second electromagnetic radiation 3016 is collected via superficies 3300. Second collected electromagnetic radiation 3016 preferably is a portion of second emitted electromagnetic radiation 3012 that is at least one of specularly reflected, diffusely reflected (e.g., due to elastic or inelastic scattering), fluoresced (e.g., due to endogenous or exogenous factors), or otherwise redirected from subcutaneous tissue.

The wavelength of second emitted and collected electromagnetic radiation 3012 and 3016 preferably is shorter than approximately 750 nanometers. The frequency therefore is at least approximately 400 terahertz. Preferably, second emitted and collected electromagnetic radiation 3012 and 3016 preferably are in the visible light portion of the electromagnetic spectrum. According to one embodiment, second emitted and collected electromagnetic radiation 3012 and 3016 preferably are in the yellow to red visible light portions of the electromagnetic spectrum. As the terminology is used herein, "yellow to red" preferably refers to electromagnetic radiation having wavelengths between approximately 570 nanometers and approximately 750 nanometers. These wavelengths generally correspond to a frequency range of approximately 525 terahertz to approximately 400 terahertz. A desirable range for second emitted and collected electromagnetic radiation 3012 and 3016 preferably includes wavelengths between approximately 570 nanometers and approximately 620 nanometers. These wavelengths generally correspond to a frequency range of approximately 525 terahertz to approximately 485 terahertz. According to other embodiments, second emitted and collected electromagnetic radiation 3012 and 3016 preferably are approximately at an isosbestic wavelength to minimize the effect of blood oxygenation on measuring tissue blood volume. As the terminology is used herein, "isosbestic wavelength" preferably refers to a wavelength at which oxyhemoglobin and deoxyhemoglobin have generally the same molar absorptivity. Conversely, absorptivity at non-isosbestic wavelengths typically is different for oxyhemoglobin and deoxyhemoglobin. For example, oxyhemoglobin typically is more absorptive than deoxyhemoglobin at non-isosbestic wavelengths of infrared light; and deoxyhemoglobin typically is more absorptive than oxyhemoglobin at non-isosbestic wavelengths of red visible light. Tissue blood volume preferably includes a summation of oxyhemoglobin and deoxyhemoglobin components. Preferably, second emitted and collected electromagnetic radiation 3012 and 3016 are at an approximately isosbestic wavelength for measuring the oxyhemoglobin and deoxyhemoglobin components of tissue blood volume with a single wavelength. According to other embodiments, second emitted and collected electromagnetic radiation 3012 and 3016 include two wavelengths: one for particularly measuring the oxyhemoglobin component of tissue blood volume and another for particularly measuring the deoxyhemoglobin component of tissue blood volume.

Figure 35A:
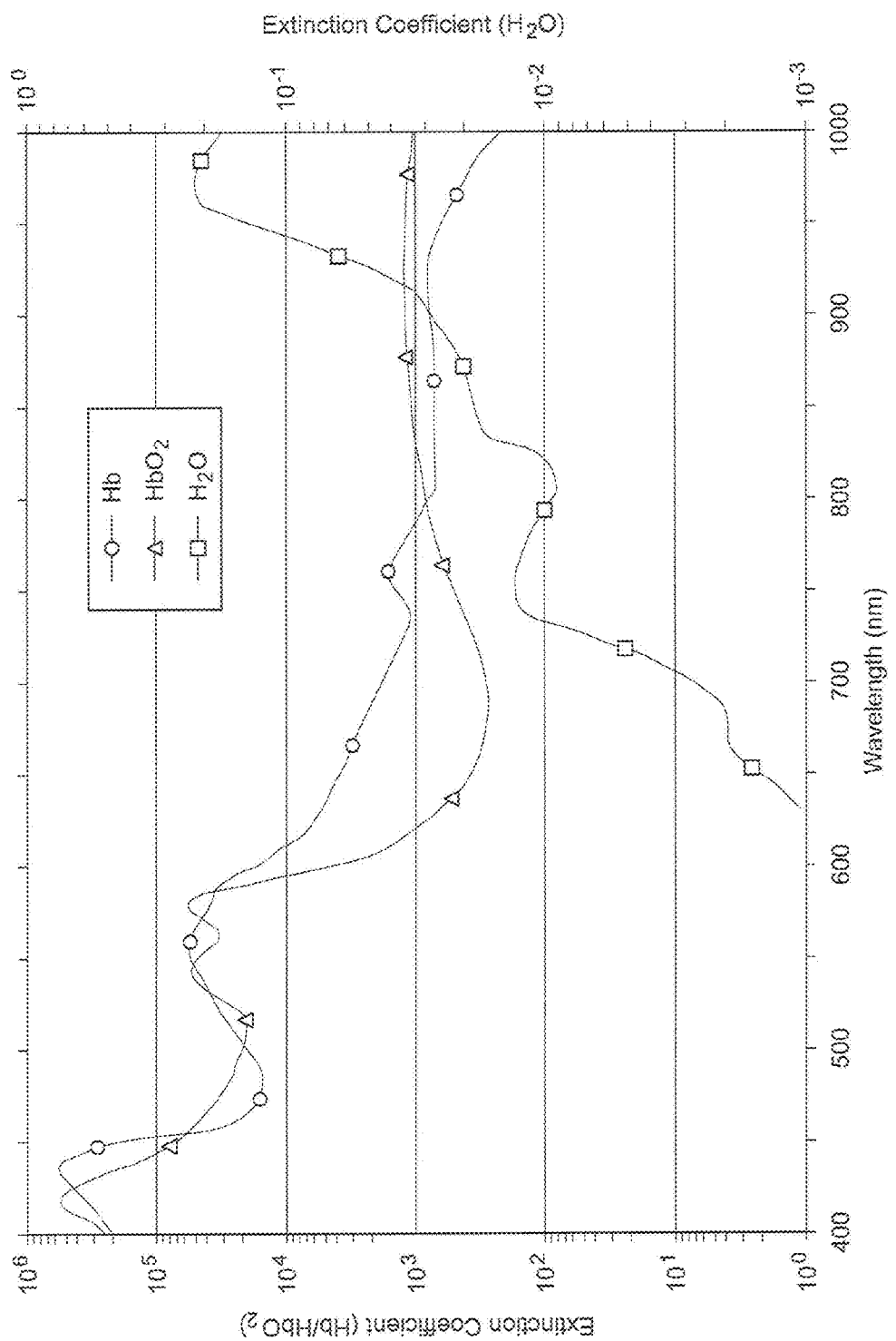
FIG. 35A is a graph of extinction coefficients for deoxyhemoglobin, oxyhemoglobin and water at electromagnetic radiation wavelengths between 400 nanometers and 1000 nanometers.

There are eight isosbestic wavelengths between approximately 400 nanometers and approximately 1,000 nanometers. Isosbestic wavelengths typically are indicated by intersections of the extinction curves for oxyhemoglobin ($HbO_2$) and deoxyhemoglobin (Hb). Referring to FIG. 35A, known isosbestic points of deoxyhemoglobin and oxyhemoglobin are shown at approximately 421 nanometers (approximately 712 terahertz), approximately 449 nanometers (approximately 668 terahertz), approximately 506 nanometers (approximately 592 terahertz), approximately 522 nanometers (approximately 574 terahertz), approximately 548 nanometers (approximately 547 terahertz), approximately 569 nanometers (approximately 527 terahertz), approximately 586 nanometers (approximately 512 terahertz), and approximately 808 nanometers (approximately 371 terahertz). According to one embodiment, a generally isosbestic wavelength for second emitted electromagnetic radiation 3012 preferably is approximately 586 nanometers.

Figure 35B:
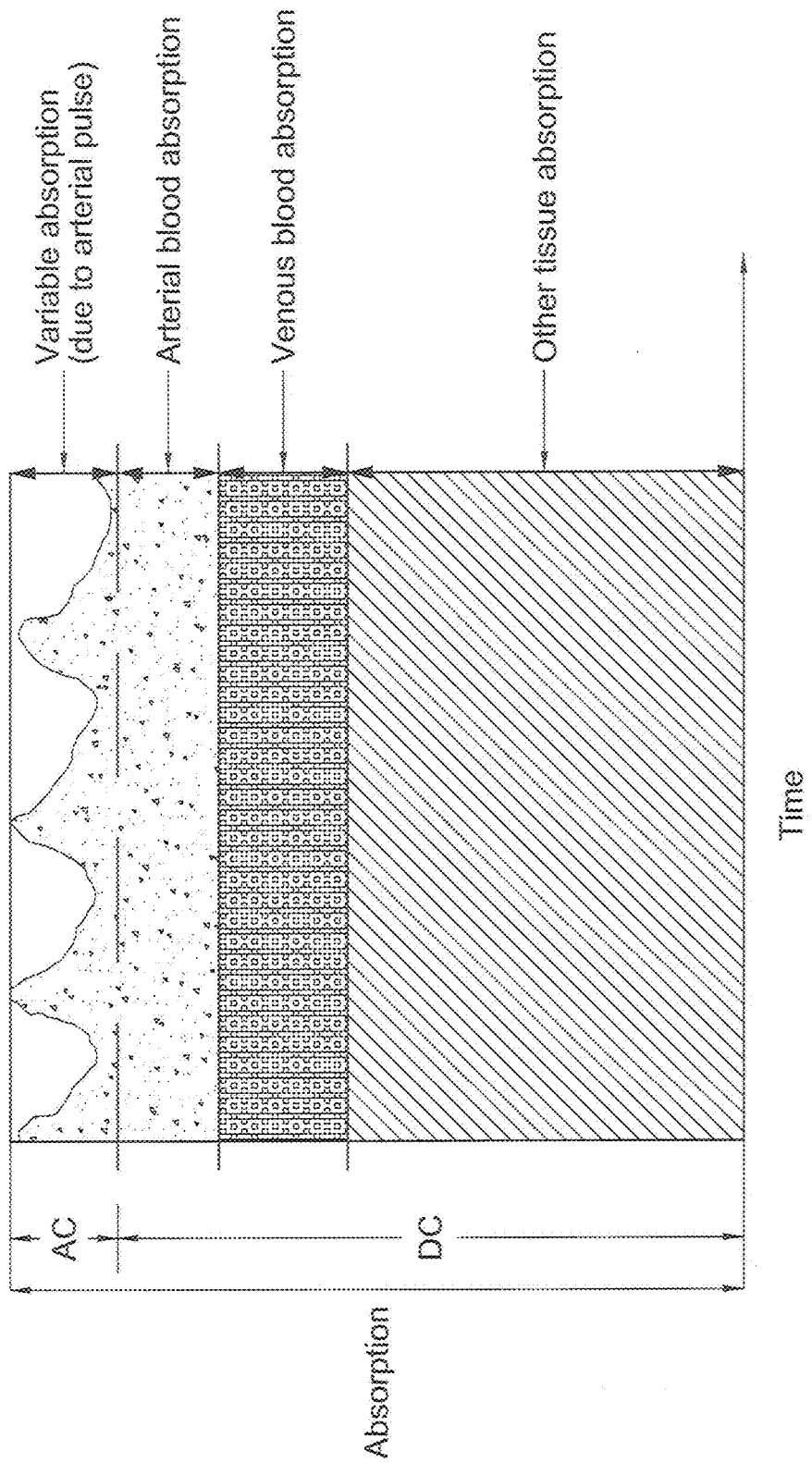
FIG. 35B is a schematic view illustrating materials in the propagation path of typical pulse oximetry systems. The relative proportions of the materials are not to scale.

According to one embodiment, second emitted and collected electromagnetic radiation 3012 and 3016 preferably are at an approximately isosbestic wavelength in contradistinction to typical pulse oximeters. Typically, pulse oximetry propagates non-isosbestic wavelengths of visible light and near-infrared radiation through biological materials including tissue, oxyhemoglobin and deoxyhemoglobin. The Beer-Lambert law relates absorption of the visible light and near-infrared radiation with (i) the absorption coefficient of a material; and (ii) the propagation path length through that material. FIG. 35B schematically illustrates the materials in the propagation path of typical pulse oximetry systems. Typically, absorption incudes a fixed component DC, which generally includes absorption by tissue, venous blood (deoxyhemoglobin) and non-pulsatile arterial blood (non-pulsatile oxyhemoglobin), and a fluctuating component AC, which generally includes absorption by pulsatile arterial blood (pulsatile oxyhemoglobin). The fluctuating component AC as compared to the fixed component DC typically is relatively small (e.g., approximately 2% of absorption) and therefore relatively difficult to accurately measure.

Pulse oximetry typically uses two non-isosbestic wavelengths for calculating blood oxygen saturation. The principle of pulse oximetry is based on different absorption characteristics of oxyhemoglobin and deoxyhemoglobin at wavelengths typically in the visible light and near-infrared radiation portions of the electromagnetic radiation spectrum. Typically, the visible light is at approximately 660 nanometers (approximately 455 terahertz) and the near-infrared radiation is at approximately 940 nanometers (approximately 320 terahertz). Pulse oximeters typically compute a normalized absorption ratio of the visible light to the near-infrared radiation according to the following equation:

$$\frac{visible}{infrared} = \frac{AC_{visible}}{DC_{visible}} \bigg/ \frac{AC_{infrared}}{DC_{infrared}}$$

and then plug the normalized absorption ratio into an algorithm or lookup table for determining blood oxygen saturation. Typically, increasing the differences between the absorption characteristics magnifies the fluctuating component AC as compared to the fixed component DC, thereby expanding the range of the normalized absorption ratio and improving accuracy in determining blood oxygen saturation. Increasing the difference between absorption coefficients of oxyhemoglobin and deoxyhemoglobin at non-isosbestic wavelengths therefore is a fundamental of accurate pulse oximetry. Moreover, measuring absorption at two wavelengths and using both measurements in a computation are required in pulse oximetry before a result, e.g., blood oxygen saturation or pulse rate, can be determined. Pulse oximetry typically cannot determine the result by measuring absorption at only one wavelength. By comparison, the second wavelength of electromagnetic radiation sensor 3000 preferably is at an approximately isosbestic wavelength because of the generally similar absorption coefficients of oxyhemoglobin and deoxyhemoglobin. According to one embodiment, the two wavelengths of electromagnetic radiation sensor 3000 independently provide (i) alerts to perform an infiltration/extravasation examination; and (ii) indications of a tissue blood volume change. System 100 therefore preferably uses the first and second wavelengths of electromagnetic radiation sensor 3000 to, respectively, analyze anatomical changes over time in the perivascular tissue P and verify the cause of the anatomical change.

Electromagnetic radiation sensor 3000 preferably also detects tissue blood volume changes in addition to those due to patient posture changes. The inventors further discovered, inter alia, electromagnetic radiation sensor 3000 detects tissue blood volume changes caused by (i) the application of certain devices; or (ii) the introduction of certain medicines. For example, electromagnetic radiation sensor 3000 preferably detects the application of sphygmomanometers, tourniquets, dressings or other devices that affect circulation and therefore affect blood perfusion in capillary beds of limbs including the cannulation site N. Other sources of tissue blood volume changes that electromagnetic radiation sensor 3000 preferably detects include the introduction of markers (e.g., methylene blue), anticoagulants, or medicines to control anemia or other blood conditions. Preferably, healthcare givers take into account such additional sources of tissue blood volume changers when deciding to perform an infiltration/extravasation examination.

Referring again to FIG. 17, electromagnetic radiation sensor 3000 preferably includes waveguides to transmit first and second emitted and collected electromagnetic radiation 3002, 3006, 3012 and 3016. As the terminology is used herein, "waveguide" preferably refers to a duct, pipe, fiber or other device that generally confines and directs the propagation of electromagnetic radiation along a path. Preferably, an emission waveguide 3210 includes an emitter face 3214 for emitting first and second emitted electromagnetic radiation 3002 and 3012, and a detection waveguide 3220 includes a detector face 3224 for collecting first and second collected electromagnetic radiation 3006 and 3016. According to one embodiment, emission waveguide 3210 preferably includes a set of emission optical fibers 3212 and detection waveguide 3220 preferably includes a set of detection optical fibers 3222. Individual emission and detection optical fibers 3212 and 3222 preferably each have an end face. Preferably, an aggregation of end faces of emission optical fibers 3212 forms emitter face 3214 and an aggregation of end faces of detection optical fibers 3222 forms detector face 3224.

Figure 18A:
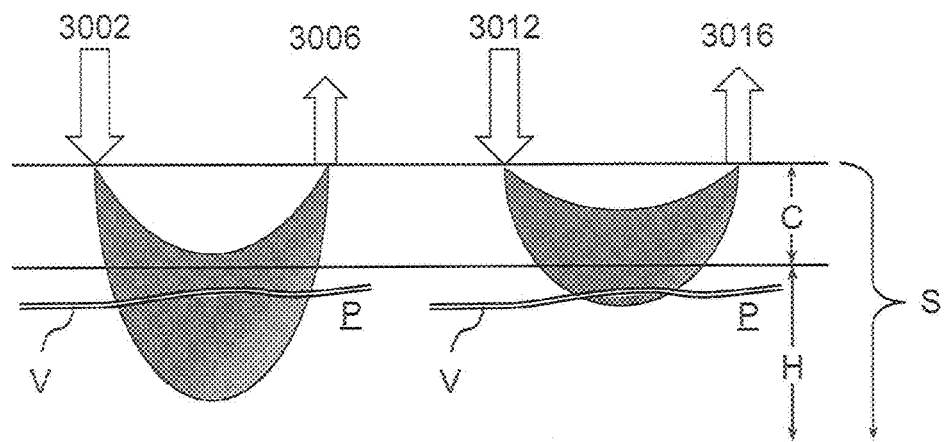
FIGS. 18A-18C are schematic cross-section views explaining how an anatomical change over time in perivascular tissue impacts the electromagnetic radiation sensor shown in FIG. 17.
Figure 18B:
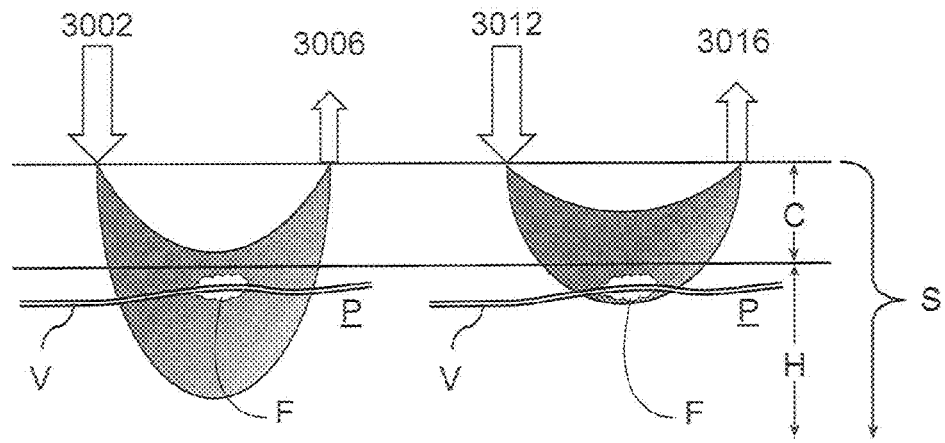
Figure 18C:
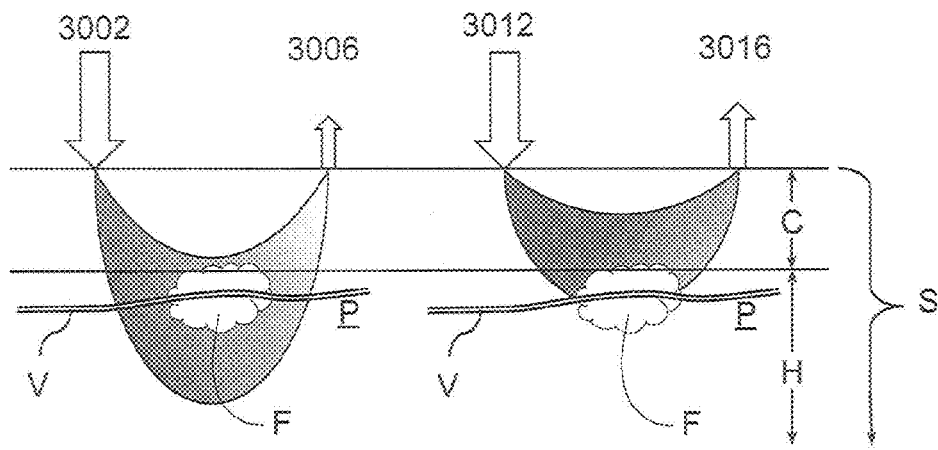

FIGS. 18A-18C schematically illustrate how an evolving infiltration/extravasation event preferably affects the electromagnetic radiation signals of electromagnetic radiation sensor 3000. FIGS. 18A-18C include individual schematic illustrations of the monitoring paths for (i) first emitted and collected electromagnetic radiation 3002 and 3006; and (ii) second emitted and collected electromagnetic radiation 3012 and 3016. According to one embodiment, the monitoring paths preferably overlap; however, they are separately shown on the left and right sides of each figure for the sake of clearly illustrating each monitoring path. Therefore, the left and right sides of individual FIGS. 18A-18C include duplicate showings of the materials (e.g., the skin S, the blood vessel V, the perivascular tissue P, and the infusate F) along the monitoring paths of electromagnetic radiation 3002, 3012, 3006 and 3016.

FIGS. 18A-18C show examples of three stages of infiltration/extravasation. FIG. 18A shows the skin S prior to an infiltration/extravasation event. Preferably, the skin S includes the cutaneous tissue C (e.g., dermis and/or the epidermis E including the stratum corneum) overlying subcutaneous tissue (e.g., the hypodermis H). The blood vessel V for intravenous therapy typically is disposed in the hypodermis H. FIG. 18B shows an infusate F beginning to accumulate in the perivascular tissue P. Accumulation of the infusate F typically begins in the hypodermis H, but may also begin in the cutaneous tissue C or at an interface of the hypodermis H with the cutaneous tissue C. FIG. 18C shows the accumulation of the infusate F expanding in the perivascular tissue P. Typically, the expanded accumulation extends further in the hypodermis H but may also extend into the cutaneous tissue C. According to one embodiment, infiltration/extravasation generally originates and/or expands in proximity to the blood vessel V as illustrated in FIGS. 18A-18C. According to other embodiments, infiltration/extravasation may originate and/or occur some distance from the blood vessel V, e.g., if pulling on the cannula C or administration set 30 causes the cannula outlet to become displaced from the blood vessel V.

The left sides of FIGS. 18A-18C schematically illustrate an optical power $\Phi_6$ of first collected electromagnetic radiation 3006 relative to an optical power $\Phi_2$ of first emitted electromagnetic radiation 3002. Preferably, first emitted electromagnetic radiation 3002 enters the skin S, at least some electromagnetic radiation propagates through the Animalia tissue, and first collected electromagnetic radiation 3006 exits the skin S. First emitted electromagnetic radiation 3002 is schematically illustrated with an arrow directed toward the skin S and first collected electromagnetic radiation 3006 is schematically illustrated with an arrow directed away from the skin S. Preferably, the relative sizes of the arrows correspond to the optical power $\Phi_2$ and the optical power $\Phi_6$. The monitoring path of first emitted and collected electromagnetic radiation 3002 and 3006 is schematically illustrated with a crescent shape that preferably includes the predominant electromagnetic radiation paths through the skin S from first emitted electromagnetic radiation 3002 to first collected electromagnetic radiation 3006. Stippling in the crescent shape schematically illustrates a distribution of optical power in the skin S with relatively weaker optical power generally indicated with less dense stippling and relatively stronger optical power generally indicated with denser stippling.

First collected electromagnetic radiation 3006 preferably is impacted by the infusate F accumulating in the perivascular tissue P. Prior to an infiltration/extravasation event (FIG. 18A), the optical power $\Phi_6$ preferably is a fraction of the optical power $\Phi_2$ due to extinction along the monitoring path. As the terminology is used herein, "extinction" preferably refers to attenuation of electromagnetic radiation due to (i) absorption; (ii) scattering; or (iii) a combination of absorption and scattering. According to one embodiment, the optical power $\Phi_6$ relative the optical power $\Phi_2$ decreases in response to the infusate F accumulating in the perivascular tissue P (FIGS. 18B and 18C).

The optical power $\Phi_6$ preferably decreases due to scattering of near-infrared electromagnetic radiation by the infusate F. Typically, the compositions of most infusates are dominated by water, which has different absorption and scattering coefficients as compared to the perivascular tissue P. At wavelengths between approximately 500 nanometers (approximately 600 terahertz) and approximately 1,300 nanometers (approximately 230 terahertz), extinction coefficients of water typically are dominated by scattering coefficients rather than absorption coefficients. Scattering therefore dominates extinction of near-infrared radiation propagating through water at wavelengths between approximately 800 nanometers and approximately 1,300 nanometers. Thus, the optical power $\Phi_6$ preferably decreases relative to the optical power $\Phi_2$ because of extinction primarily due to scattering when the infusate F accumulates in the perivascular tissue P. Decreased optical power is schematically illustrated in FIGS. 18A-18C by the changing relative sizes of the arrows corresponding to first emitted and collected electromagnetic radiation 3002 and 3006.

The right sides of FIGS. 18A-18C schematically illustrate an optical power $\Phi_{16}$ of second collected electromagnetic radiation 3016 relative to an optical power $\Phi_{12}$ of second emitted electromagnetic radiation 3012. Preferably, second emitted electromagnetic radiation 3012 enters the skin S, at least some electromagnetic radiation propagates through the Animalia tissue, and second collected electromagnetic radiation 3016 exits the skin S. Second emitted electromagnetic radiation 3012 is schematically illustrated with an arrow directed toward the skin S and second collected electromagnetic radiation 3016 is schematically illustrated with an arrow directed away from the skin S. Preferably, the relative sizes of the arrows correspond to the optical power $\Phi_{12}$ relative to the optical power $\Phi_{16}$. The monitoring path of second emitted and collected electromagnetic radiation 3012 and 3016 is schematically illustrated with a crescent shape that preferably includes the predominant electromagnetic radiation paths through the skin S from second emitted electromagnetic radiation 3012 to second collected electromagnetic radiation 3016. Stippling in the crescent shape schematically illustrates a distribution of optical power in the skin S with relatively weaker optical power generally indicated with less dense stippling and relatively stronger optical power generally indicated with denser stippling.

The infusate F accumulating in the perivascular tissue P preferably also impacts second collected electromagnetic radiation 3016. Prior to an infiltration/extravasation event (FIG. 18A), the optical power $\Phi_{16}$ preferably is a fraction of the optical power $\Phi_{12}$ due to extinction along the monitoring path. According to one embodiment, the optical power $\Phi_{16}$ preferably decreases relative to the optical power $\Phi_{12}$ in response to the infusate F accumulating in the perivascular tissue P (FIGS. 18B and 18C).

Scattering of visible light by the infusate F preferably decreases the optical power $\Phi_{16}$. According to one embodiment, second collected electromagnetic radiation 3016 preferably is in the yellow to red visible light portions of the electromagnetic spectrum. As the terminology is used herein, "yellow to red" preferably refers to electromagnetic radiation having wavelengths between approximately 570 nanometers and approximately 750 nanometers. These wavelengths generally correspond to a frequency range of approximately 525 terahertz to approximately 400 terahertz. A desirable range for second collected electromagnetic radiation 3016 preferably includes wavelengths between approximately 570 nanometers and approximately 620 nanometers. These wavelengths generally correspond to a frequency range of approximately 525 terahertz to approximately 485 terahertz. Accumulation of the infusate F causes the optical power $\Phi_{16}$ to decrease due to extinction. As discussed above, extinction coefficients at wavelengths between approximately 570 nanometers and approximately 750 nanometers typically are dominated by scattering coefficients rather than absorption coefficients. Thus, the optical power $\Phi_{16}$ preferably decreases relative to the optical power $\Phi_{12}$ because of extinction primarily due to scattering when the infusate F accumulates in the perivascular tissue P. Decreased optical power is schematically illustrated in FIGS. 18A-18C by the changing relative sizes of the arrows corresponding to second emitted and collected electromagnetic radiation 3012 and 3016.

Certain differences and similarities between first and second collected electromagnetic radiation 3006 and 3016 preferably are apparent in the three stages of infiltration/extravasation shown in FIGS. 18A-18C. Preferably, first emitted and collected electromagnetic radiation 3002 and 3006 generally penetrate deeper into the skin S than second emitted and collected electromagnetic radiation 3012 and 3016. According to one embodiment, the predominant electromagnetic radiation paths from first emitted electromagnetic radiation 3002 to first collected electromagnetic radiation 3006 preferably extend along a longer path length though the hypodermis H; whereas, the predominant electromagnetic radiation paths through the skin S from second emitted electromagnetic radiation 3012 to second collected electromagnetic radiation 3016 preferably extend a shorter path length though the cutaneous tissue C. Accordingly, the percentage of extinction solely due to the skin S (FIG. 18A) preferably is greater between first emitted and collected electromagnetic radiation 3002 and 3006 than between second emitted and collected electromagnetic radiation 3012 and 3016 because of the relative path lengths. As an infiltration/extravasation event begins (FIG. 18B) and expands (FIG. 18C), the percentage of electromagnetic power extinction due to the infusate F preferably is proportionally greater for near-infrared radiation than visible light. In particular, an extinction rate of first collected electromagnetic radiation 3006 relative to first emitted electromagnetic radiation 3002 preferably is greater than an extinction rate of second collected electromagnetic radiation 3016 relative to second emitted electromagnetic radiation 3012. According to one embodiment, comparing the stage prior to an infiltration/extravasation event (FIG. 18A) and the stage with expanded accumulation of the infusate F (FIG. 18C), preferably there is up to 40% or more decrease in the optical power $\Phi_6$ and up to 30% or more decrease in the optical power $\Phi_{16}$.

Figure 18D:
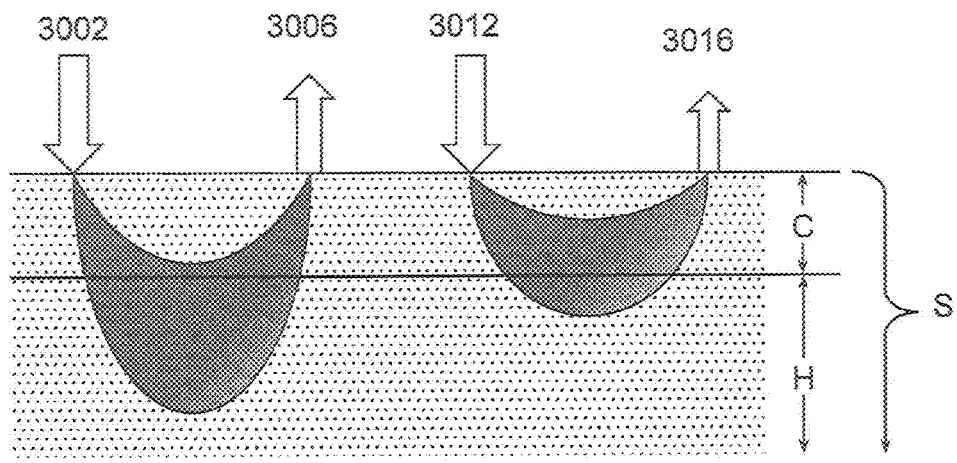
FIGS. 18D-18F are schematic cross-section views explaining how a tissue volume blood change impacts the electromagnetic radiation sensor shown in FIG. 17.
Figure 18E:
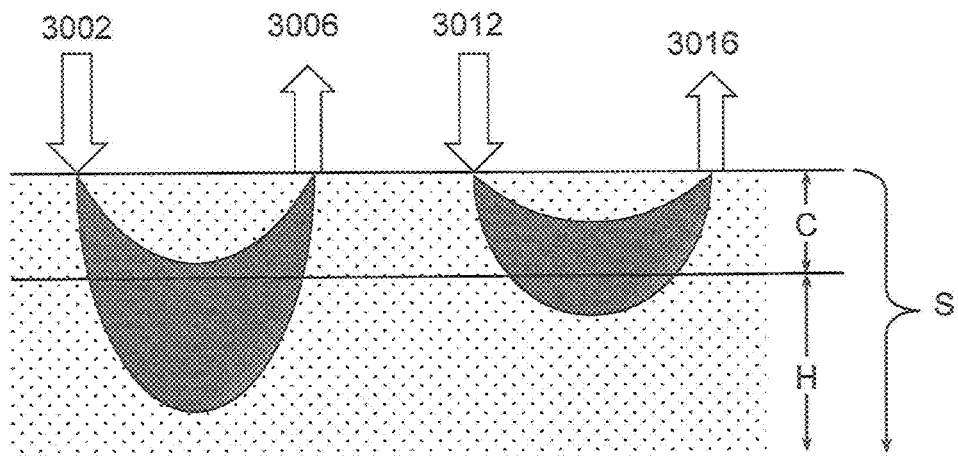
Figure 18F:
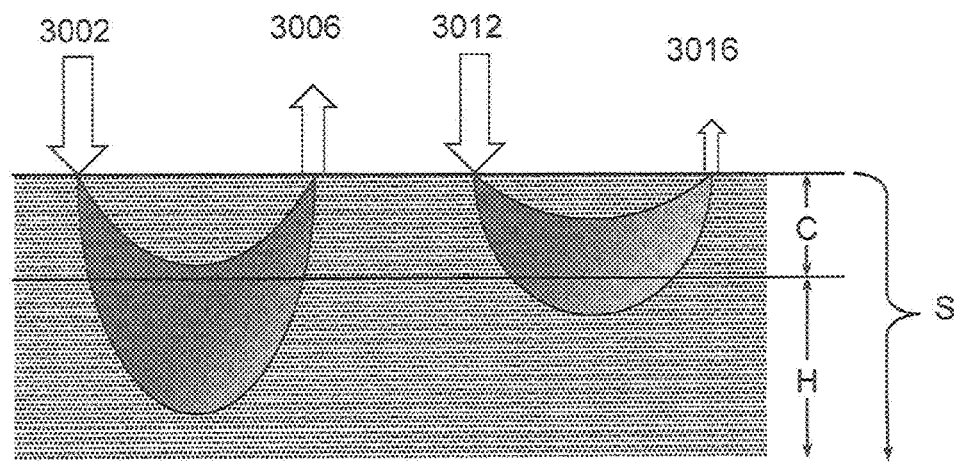

FIGS. 18D-18F schematically illustrate how changing the tissue blood volume preferably affects the electromagnetic radiation signals of electromagnetic radiation sensor 3000. FIGS. 18D-18F include individual schematic illustrations of the monitoring paths for (i) first emitted and collected electromagnetic radiation 3002 and 3006; and (ii) second emitted and collected electromagnetic radiation 3012 and 3016. According to one embodiment, the monitoring paths preferably overlap; however, they are separately shown on the left and right sides of each figure for the sake of clearly illustrating each monitoring path. The left and right sides of individual FIGS. 18D-18F include duplicate showings of the materials (e.g., the skin S including the cutaneous tissue C overlying the hypodermis H) along the monitoring paths of electromagnetic radiation 3002, 3012, 3006 and 3016.

FIGS. 18D-18F show examples of three states of the tissue blood volume. FIG. 18D schematically illustrates a certain blood volume $TBV_1$ of the skin S. FIG. 18E schematically illustrates a decreased tissue blood volume $TBV_2$ relative to the tissue blood volume $TBV_1$. FIG. 18F schematically illustrates an increased tissue blood volume $TBV_3$ relative to the tissue blood volume $TBV_1$.

The left sides of FIGS. 18D-18F schematically illustrate the optical power $\Phi_6$ relative to the optical power $\Phi_2$. Preferably, first emitted electromagnetic radiation 3002 enters the skin S, at least some electromagnetic radiation propagates through the Animalia tissue, and first collected electromagnetic radiation 3006 exits the skin S. First emitted electromagnetic radiation 3002 is schematically illustrated with an arrow directed toward the skin S and first collected electromagnetic radiation 3006 is schematically illustrated with an arrow directed away from the skin S. Preferably, the relative sizes of the arrows correspond to the optical power $\Phi_2$ relative to the optical power $\Phi_6$. The monitoring path of first emitted and collected electromagnetic radiation 3002 and 3006 is schematically illustrated with a crescent shape that preferably includes the predominant electromagnetic radiation paths through the skin S from first emitted electromagnetic radiation 3002 to first collected electromagnetic radiation 3006. Stippling in the crescent shape schematically illustrates a distribution of optical power in the skin S with relatively weaker optical power generally indicated with less dense stippling and relatively stronger optical power generally indicated with denser stippling.

First collected electromagnetic radiation 3006 preferably is impacted by changes in the tissue blood volume along the monitoring path. At the tissue blood volume $TBV_1$ (FIG. 18D), the optical power $\Phi_6$ preferably is a fraction of the optical power $\Phi_2$ because hemoglobin along the monitoring path causes electromagnetic radiation extinction. According to one embodiment, the optical power $\Phi_6$ relative to first emitted electromagnetic radiation 3002 preferably increases when the tissue blood volume $TBV_1$ changes to the decreased tissue blood volume $TBV_2$ (FIG. 18E), and the optical power $\Phi_6$ relative to first emitted electromagnetic radiation 3002 preferably decreases when the tissue blood volume $TBV_1$ changes to the increased tissue blood volume $TBV_3$ (FIG. 18F).

The optical power $\Phi_6$ preferably responds to absorption of near-infrared electromagnetic radiation by hemoglobin. Typically, hemoglobin has different absorption and scattering coefficients as compared to the perivascular tissue P. As discussed above, absorption by hemoglobin depends on blood oxygenation; however, extinction coefficients of both deoxyhemoglobin and oxyhemoglobin are dominated by absorption coefficients rather than scattering coefficients. Absorption therefore dominates extinction of near-infrared radiation propagating through deoxyhemoglobin and oxyhemoglobin. Thus, the optical power $\Phi_6$ increases relative to the optical power $\Phi_2$ as extinction preferably due to absorption decreases when there is the decreased tissue blood volume $TBV_2$ (FIG. 18E), and the optical power $\Phi_6$ decreases relative to the optical power $\Phi_2$ as extinction preferably due to absorption increases when there is the increased tissue blood volume $TBV_3$ (FIG. 18F). These optical power changes are schematically illustrated by the changing relative sizes of the arrows corresponding to first emitted and collected electromagnetic radiation 3002 and 3006.

The right sides of FIGS. 18D-18F schematically illustrate the optical power $\Phi_{16}$ relative to the optical power $\Phi_{12}$. Preferably, second emitted electromagnetic radiation 3012 enters the skin S, at least some electromagnetic radiation propagates through the Animalia tissue, and second collected electromagnetic radiation 3016 exits the skin S. Second emitted electromagnetic radiation 3012 is schematically illustrated with an arrow directed toward the skin S and second collected electromagnetic radiation 3016 is schematically illustrated with an arrow directed away from the skin S. Preferably, the relative sizes of the arrows correspond to the optical power $\Phi_{12}$ and the optical power $\Phi_{16}$. The monitoring path of second emitted and collected electromagnetic radiation 3012 and 3016 is schematically illustrated with a crescent shape that preferably includes the predominant electromagnetic radiation paths through the skin S from second emitted electromagnetic radiation 3012 to second collected electromagnetic radiation 3016. Stippling in the crescent shape schematically illustrates a distribution of optical power in the skin S with relatively weaker optical power generally indicated with less dense stippling and relatively stronger optical power generally indicated with denser stippling.

Changing tissue blood volume along the monitoring path preferably also impacts second collected electromagnetic radiation 3016. At the tissue blood volume $TBV_1$ (FIG. 18D), the optical power $\Phi_{16}$ preferably is a fraction of the optical power $\Phi_{12}$ because hemoglobin along the monitoring path causes extinction. According to one embodiment, the optical power $\Phi_{16}$ preferably increases relative to the optical power $\Phi_{12}$ when the tissue blood volume $TBV_1$ changes to the decreased tissue blood volume $TBV_2$ (FIG. 18E), and the optical power $\Phi_{16}$ preferably decreases relative to the optical power $\Phi_{12}$ when the tissue blood volume $TBV_1$ changes to the increased tissue blood volume $TBV_3$ (FIG. 18F).

Absorption of visible light by oxyhemoglobin and deoxyhemoglobin preferably changes the optical power $\Phi_{16}$. According to one embodiment, a desirable range of wavelengths for second collected electromagnetic radiation 3016 preferably is between approximately 570 nanometers (approximately 525 terahertz) and approximately 750 nanometers (approximately 400 terahertz). As discussed above, extinction coefficients of both deoxyhemoglobin and oxyhemoglobin are dominated by absorption coefficients rather than scattering coefficients. Absorption therefore dominates extinction of visible light propagating through deoxyhemoglobin and oxyhemoglobin. Thus, the optical power $\Phi_{16}$ increases relative to the optical power $\Phi_{12}$ as extinction preferably due to absorption decreases when there is the decreased tissue blood volume $TBV_2$ (FIG. 18E), and the optical power $\Phi_{16}$ decreases relative to the optical power $\Phi_{12}$ as extinction preferably due to absorption increases when there is the increased tissue blood volume $TBV_3$ (FIG. 18F). These optical power changes are schematically illustrated by the changing relative sizes of the arrows corresponding to first emitted and collected electromagnetic radiation 3012 and 3016.

Certain differences and similarities between first and second collected electromagnetic radiation 3006 and 3016 preferably are apparent in the three states of the tissue blood volume shown in FIGS. 18D-18F. The distributions of blood in the skin S for the tissue blood volume $TBV_1$, the decreased tissue blood volume $TBV_2$ and the increased tissue blood volume $TBV_3$ are illustrated as being generally uniform for the sake of explaining the impact of changing tissue blood volume; however, the distribution of blood in the skin S may not be uniform. The percentage decrease of extinction preferably is greater for visible light than near-infrared radiation when there is the decreased tissue blood volume $TBV_2$. The percentage increase of extinction preferably is greater for visible light than near-infrared radiation when there is the increased tissue blood volume $TBV_3$. Thus, the extinction of second collected electromagnetic radiation 3016 relative to second emitted electromagnetic radiation 3012 preferably is more responsive to changing tissue blood volume than is the extinction of first collected electromagnetic radiation 3006 relative to first emitted electromagnetic radiation 3002. According to one embodiment, comparing the tissue blood volume $TBV_1$ (FIG. 18D) with the increased tissue blood volume $TBV_3$ (FIG. 18F), preferably there is up to 20% or more decrease in the optical power $\Phi_6$ and up to 50% or more decrease in the optical power $\Phi_{16}$.

The inventors also discovered a different problem regarding accurately alerting healthcare givers to perform an infiltration/extravasation examination. In particular, healthcare givers may not be accurately alerted because of a relatively low signal-to-noise ratio of collected electromagnetic radiation 3006. Thus, the inventors discovered, inter alia, that noise component 3006a in collected electromagnetic radiation 3006 frequently obscures signal component 3006b that alerts healthcare givers to perform an infiltration/extravasation examination.

The inventors also discovered a source of the problem is emitted electromagnetic radiation 3002 being reflected, scattered, or otherwise redirected from various tissues/depths below the stratum corneum of the skin S. Referring again to FIG. 17, the inventors discovered that noise component 3006a of collected electromagnetic radiation 3006 includes cutaneous electromagnetic radiation 3002a that is reflected, scattered, or otherwise redirected from relatively shallow tissue, e.g., the cutaneous tissue C, and that signal component 3006b of collected electromagnetic radiation 3006 includes transcutaneous electromagnetic radiation 3002b that is reflected, scattered, or otherwise redirected from the relatively deep tissue, e.g., the hypodermis H. The inventors further discovered, inter alia, that signal component 3006b from relatively deep tissue provides more accurate indications for healthcare givers to perform an infiltration/extravasation examination and that noise component 3006a from relatively shallow tissue frequently obscures signal component 3006b.

The inventors further discovered that sensor configuration preferably is related to the signal-to-noise ratio of a skin-coupled sensor. In particular, the inventors discovered that the relative configuration of emission and detection waveguides 3210 and 3220 preferably impact the signal-to-noise ratio of collected electromagnetic radiation 3006. Thus, the inventors discovered, inter alia, that the geometry, topography and/or angles of emission and detection waveguides 3210 and 3220 preferably impact the sensitivity of electromagnetic radiation sensor 3000 to signal component 3006b relative to noise component 3006a.

Electromagnetic radiation sensor 3000 preferably includes superficies 3300 that overlies and confronts the skin S. Preferably, superficies 3300 includes a housing surface 3120, emitter face 3214, and detector face 3224. Superficies 3300 preferably may also include façades of a filler 3150 (see FIGS. 22 and 23A) that occludes apertures in housing surface 3120 around emission and detection end faces 3214 and 3224. Preferably, superficies 3300 is a three-dimensional surface contour that is generally smooth. As the terminology is used herein, "smooth" preferably refers to being substantially continuous and free of abrupt changes.

Figure 19:
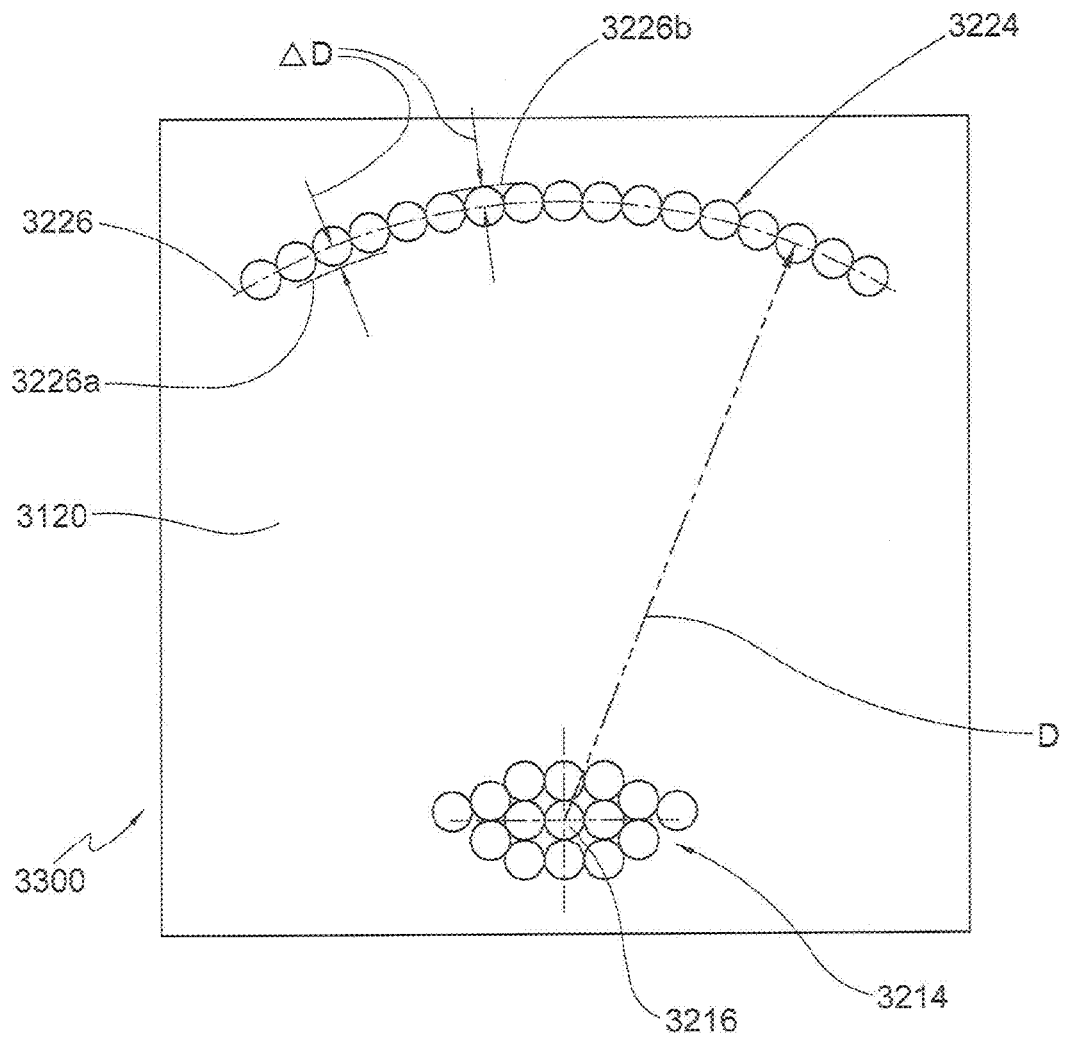
FIG. 19 is a schematic plan view illustrating a superficies geometry of the electromagnetic radiation sensor shown in FIG. 17.

FIG. 19 shows an example of superficies 3300 having a suitable geometry for observing anatomical changes over time in the perivascular tissue P. In particular, the geometry of superficies 3300 preferably includes the relative spacing and shapes of emission and detector faces 3214 and 3224. According to one embodiment, a cluster of emission optical fiber end faces preferably has a geometric centroid 3216 and an arcuate arrangement of detection optical fiber end faces preferably extends along a curve 3226. As the terminology is used herein, "cluster" preferably refers to a plurality of generally circular optical fiber end faces that are arranged such that at least one end face is approximately tangent with respect to at least three other end faces. Preferably, curve 3226 is spaced from geometric centroid 3212 by a nominal spacing distance D. Curve 3226 may be approximated by a series of line segments that correspond to individual chords of generally circular detection optical fiber end faces. Accordingly, each detection optical fiber end face preferably is tangent to at most two other end faces. The arcuate arrangement of detection optical fiber end faces includes borders with radii of curvature that preferably originate at geometric centroid 3216, e.g., similar to curve 3226. Preferably, a concave border 3226a has a radius of curvature that is less than the nominal spacing distance D by an increment ΔD, and a convex border 3226b has a radius of curvature that is greater than the nominal spacing distance D by an increment ΔD. According to one embodiment, increment ΔD is approximately equal to the radius of individual detection optical fiber end faces. According to other embodiments, detector face 3224 preferably includes individual sets of detection optical fiber end faces arranged in generally concentric curves disposed in a band between concave and convex borders 3226a and 3226b. As the terminology is used herein, "band" preferably refers to a strip or stripe that is differentiable from an adjacent area or material.

Figure 20A:
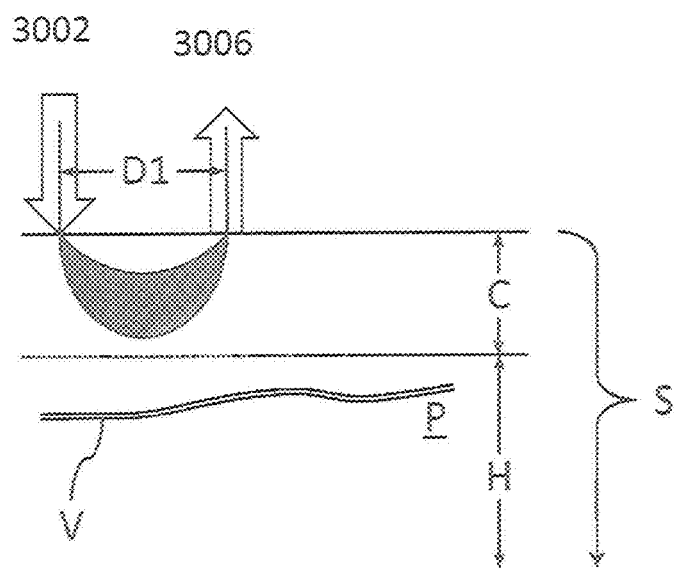
FIGS. 20A-20C are schematic cross-section views explaining the impact of different nominal spacing distances between emission and detection waveguides of the electromagnetic radiation sensor shown in FIG. 17.
Figure 20B:
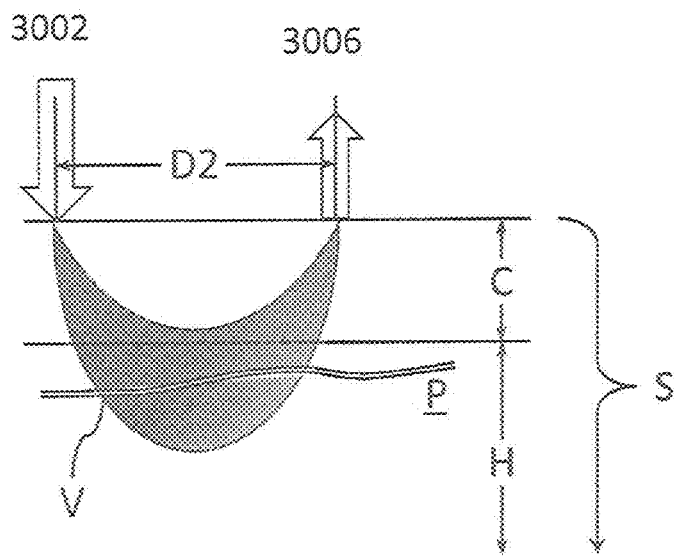
Figure 20C:
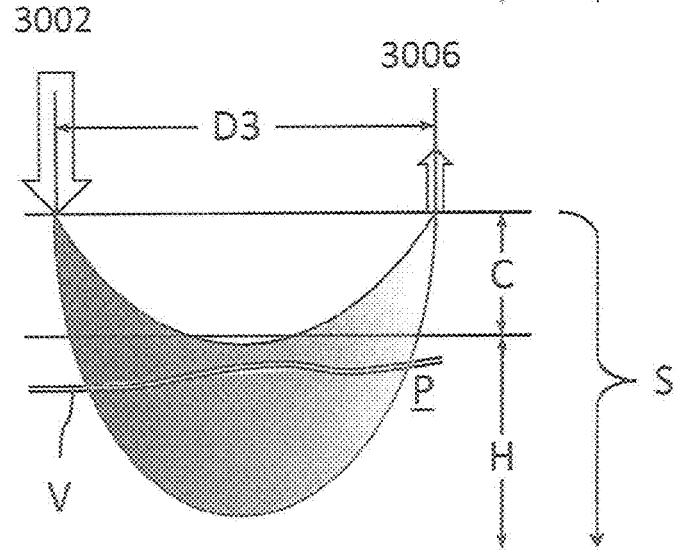

FIGS. 20A-20C illustrate how different nominal spacing distances between emission and detection waveguides 3210 and 3220 preferably impact collected electromagnetic radiation 3006. Preferably, emitted electromagnetic radiation 3002 enters the skin S from emission waveguide 3210, electromagnetic radiation propagates through the Animalia tissue, and collected electromagnetic radiation 3006 exits the Animalia tissue toward detection waveguide 3220. Emitted electromagnetic radiation 3002 is schematically illustrated with an arrow directed toward the skin S and collected electromagnetic radiation 3006 is schematically illustrated with an arrow directed away from the skin S. Preferably, the relative sizes of the arrows correspond to the optical power $\Phi_2$ and the optical power $\Phi_6$. The propagation is schematically illustrated with crescent shapes that preferably include the predominant electromagnetic radiation paths through the skin S from emitted electromagnetic radiation 3002 to collected electromagnetic radiation 3006. Stippling in the crescent shape schematically illustrates a distribution of optical power in the skin S with relatively weaker optical power generally indicated with less dense stippling and relatively stronger optical power generally indicated with denser stippling. Referring to FIG. 20A, a first nominal spacing distance D1 preferably separates emitted electromagnetic radiation 3002 and collected electromagnetic radiation 3006. At the first nominal spacing distance D1, the paths of electromagnetic radiation through the skin S generally are relatively short and predominantly extend through the cutaneous tissue C. Referring to FIG. 20B, a second nominal spacing distance D2 preferably separates emitted electromagnetic radiation 3002 and collected electromagnetic radiation 3006. At the second nominal spacing distance D2, the paths of electromagnetic radiation preferably penetrate deeper into the skin S and extend in both the cutaneous tissue C and the hypodermis H. Referring to FIG. 20C, a third nominal spacing distance D3 preferably separates emitted electromagnetic radiation 3002 and collected electromagnetic radiation 3006. At the third nominal spacing distance D3, the paths of electromagnetic radiation through the skin S generally are relatively long and predominantly extend through the hypodermis H.

The inventors discovered, inter alia, that varying the spacing distance between emission and detection waveguides 3210 and 3220 preferably changes a balance between the optical power $\Phi_6$ and the signal-to-noise ratio of collected electromagnetic radiation 3006. The optical power $\Phi_6$ preferably is greater than the optical power $\Phi_2$ for narrower nominal spacing distance D1 as compared to broader nominal spacing distance D3. On the other hand, the signal-to-noise ratio of collected electromagnetic radiation 3006 preferably is higher for broader nominal spacing distance D3 as compared to narrower nominal spacing distance D1. Preferably, there is an intermediate nominal spacing distance D2 that improves the signal-to-noise ratio as compared to narrower nominal spacing distance D1 and, as compared to broader nominal spacing distance D3, improves the optical power $\Phi_6$ relative to the optical power $\Phi_2$.

The inventors designed and analyzed a skin phantom preferably to identify an optimum range for the intermediate nominal spacing distance D2. Preferably, the skin phantom characterizes several layers of Animalia skin including at least the epidermis (including the stratum corneum), dermis, and hypodermis. Table A shows the thicknesses, refractive indices, scattering coefficients, and absorption coefficients for each layer according to one embodiment of the skin phantom. Analyzing the skin phantom preferably includes tracing the propagation of up to 200,000,000 or more rays through the skin phantom to predict changes in the optical power $\Phi_6$. Examples of suitable ray-tracing computer software include ASAP® from Breault Research Organization, Inc. (Tucson, Ariz., US) and an open source implementation of a Monte Carlo Multi-Layer (MCML) simulator from the Biophotonics Group at the Division of Atomic Physics (Lund University, Lund, SE). The MCML simulator preferably uses CUDA™ from NVDIA Corporation (Santa Clara, Calif., US) or another parallel computing platform and programming model. Preferably, a series of 1-millimeter thick sections simulate infiltrated perivascular tissue at depths up to 10 millimeters below the stratum corneum. The infiltrated perivascular tissue sections preferably are simulated with an infusate that approximates water, e.g., having a refractive index of approximately 1.33. Based on computer analysis of the skin phantom, the inventors discovered, inter alia, a relationship exists between (1) the spacing distance between emission and detection waveguides 3210 and 3220; (2) an expected depth below the stratum corneum for the perivascular tissue P at which anatomical changes over time preferably are readily observed; and (3) the wavelength of the electromagnetic radiation.

Figure 21:
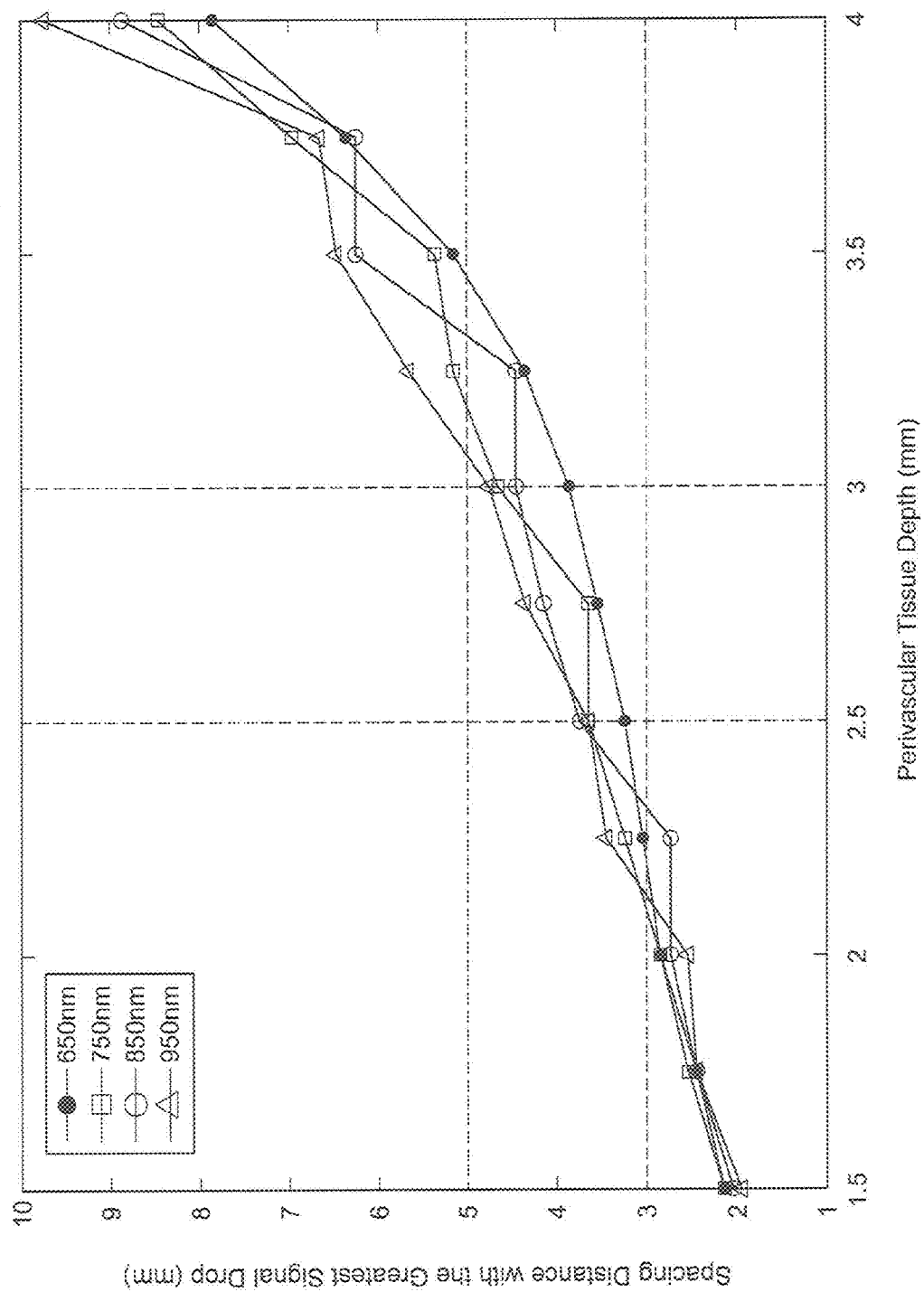
FIG. 21 is a graph illustrating a relationship between spacing, depth and wavelength for the electromagnetic radiation sensor shown in FIG. 17.

FIG. 21 shows a graphical representation of the spacing/depth/wavelength relationship based on a computer analysis of the skin phantom. In particular, FIG. 21 shows a plot of spacing distances with the greatest signal drop at various perivascular tissue depths for certain wavelengths of electromagnetic radiation. The terminology "spacing distance with the greatest signal drop" preferably refers to the spacing distance between emission and detection waveguides 3210 and 3220 that experiences the greatest drop in the optical power $\Phi_6$. The terminology "perivascular tissue depth" preferably refers to the depth below the stratum corneum of the perivascular tissue P at which anatomical changes over time are readily observed. According to the embodiment illustrated in FIG. 21, emission and detection waveguides 3210 and 3220 that preferably are separated between approximately 3 millimeters and approximately 5 millimeters are expected to readily observe anatomical changes at depths between approximately 2.5 millimeters and approximately 3 millimeters below the stratum corneum for wavelengths between approximately 650 nanometers and approximately 950 nanometers (between approximately 460 terahertz and approximately 315 terahertz). Preferably, the spacing distance range between emission and detection waveguides 3210 and 3220 is between approximately 3.7 millimeters and approximately 4.4 millimeters to observe an anatomical change over time in the perivascular tissue P at an expected depth of approximately 2.75 millimeters when the electromagnetic radiation wavelength is between approximately 650 nanometers and approximately 950 nanometers. The spacing distance between emission and detection waveguides 3210 and 3220 preferably is approximately 4.5 millimeters to observe an anatomical change over time in the perivascular tissue P at an expected depth of approximately 2.8 millimeters when the electromagnetic radiation wavelength is approximately 950 nanometers. Preferably, the spacing distance between emission and detection waveguides 3210 and 3220 is approximately 4 millimeters to observe an anatomical change over time in the perivascular tissue P at an expected depth of approximately 2.6 millimeters when the electromagnetic radiation wavelength is between approximately 850 nanometers (approximately 350 terahertz) and approximately 950 nanometers.

Electromagnetic radiation sensor 3000 preferably aids in observing anatomical changes that also occur at unexpected depths below the stratum corneum of the skin S. Preferably, the expected depth at which an anatomical change is expected to occur is related to, for example, the thickness of the cutaneous tissue C and the location of blood vessels V in the hypodermis H. Relatively thicker cutaneous tissue C and/or a blood vessel V located relatively deeper in the hypodermis H preferably increase the expected perivascular tissue depth for readily observing an anatomical change. Conversely, relatively thinner cutaneous tissue C and/or a relatively shallow blood vessel V, e.g., located close to the interface between the cutaneous tissue C and the hypodermis H, preferably decrease the expected perivascular tissue depth for readily observing an anatomical change. There may be a time delay observing anatomical changes that begin at unexpected distances from electromagnetic radiation sensor 3000. The delay may last until the anatomical change extends within the observational limits of electromagnetic radiation sensor 3000. For example, if anatomical changes over time begin at unexpected depths below the stratum corneum, observing the anatomical change may be delayed until the anatomical change extends to the expected depths below the stratum corneum.

The shapes of emission and detector faces 3214 and 3224 preferably are related to the spacing distance range between emission and detection waveguides 3210 and 3220. Preferably, each individual point of emitter face 3214 is disposed a minimum distance from each individual point of detector face 3224, and each individual point of emitter face 3214 is disposed a maximum distance from each individual point of detector face 3224. The minimum and maximum distances preferably correspond to the extremes of the range for the intermediate spacing distance D2. Preferably, the minimum distance is between approximately 2 millimeters and approximately 3.5 millimeters, and the maximum distance preferably is between approximately 4.5 millimeters and approximately 10 millimeters. According to one embodiment, each individual point of emitter face 3214 is disposed a minimum distance not less than 3 millimeters from each individual point of detector face 3224, and each individual point of emitter face 3214 is disposed a maximum distance not more than 5 millimeters from each individual point of detector face 3224. Preferably, the minimum distance is approximately 3.5 millimeters and the maximum distance is approximately 4.5 millimeters. According to other embodiments, each individual point of emitter face 3214 is spaced from each individual point of detector face 3224 such that emitted electromagnetic radiation 3002 transitions to collected electromagnetic radiation 3006 at a depth of penetration into the Animalia tissue preferably between approximately 1 millimeter and approximately 6 millimeters below the stratum corneum of the skin S. Preferably, the transition between transcutaneous electromagnetic radiation 3002b and signal component 3006b along individual electromagnetic radiation paths occur at the point of deepest penetration into the Animalia tissue. Emitted and collected electromagnetic radiation 3002 and 3006 preferably transition in the hypodermis H and may also transition in the dermis of relatively thick cutaneous tissue C. Preferably, transcutaneous electromagnetic radiation 3002*b* and signal component 3006*b* transition approximately 2.5 millimeters to approximately 3 millimeters below the stratum corneum of the skin S.

Figure 22:
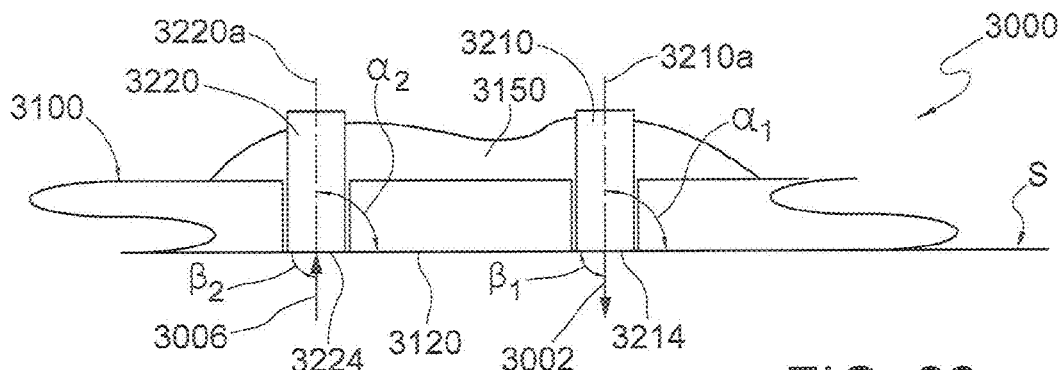
FIG. 22 is a schematic cross-section view illustrating an angular relationship between waveguides of the electromagnetic radiation sensor shown in FIG. 17.
Figure 23A:
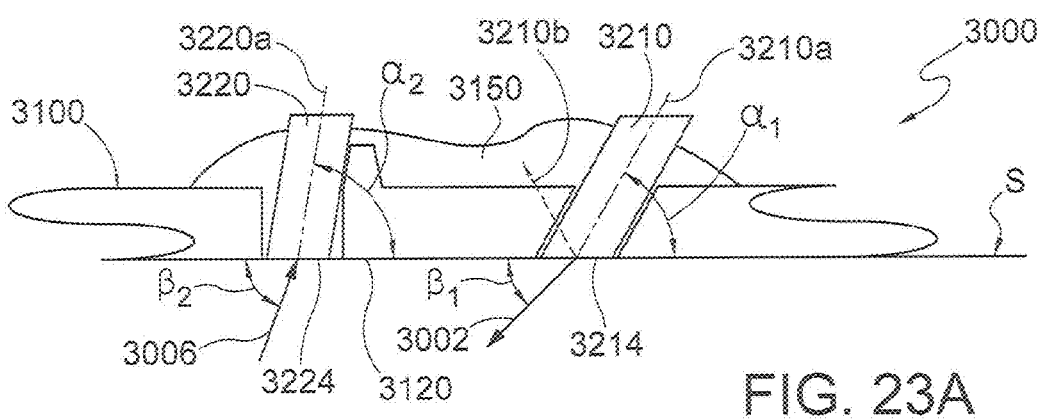
FIG. 23A is a schematic cross-section view illustrating another angular relationship between waveguides of an electromagnetic radiation sensor according to the present disclosure.
Figure 23B:
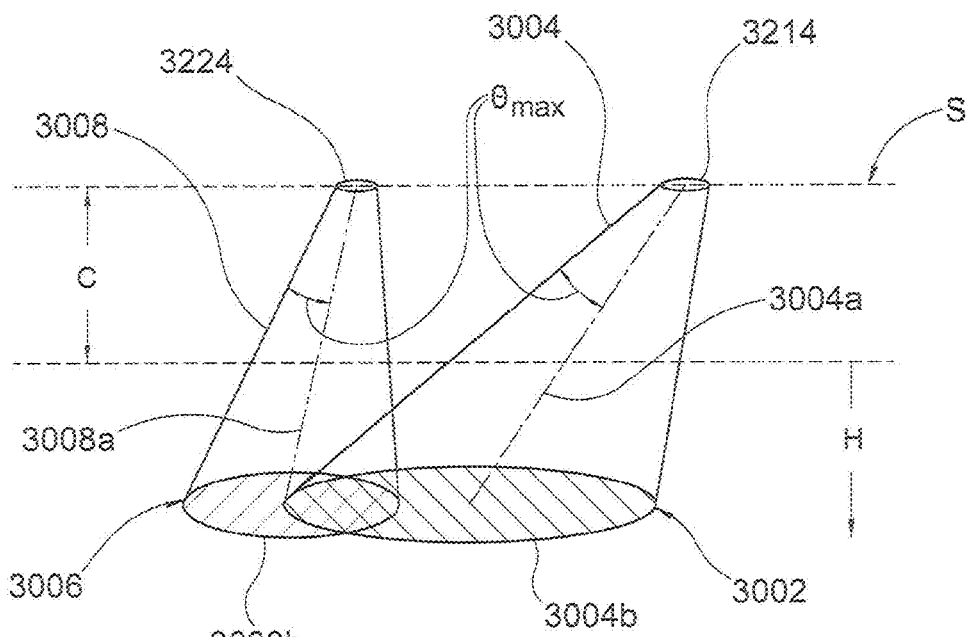
FIG. 23B illustrates a technique for representing the interplay between emitted and collected electromagnetic radiation of the waveguides shown in FIG. 23A.

The inventors also discovered, inter alia, that angles of intersection between superficies 3300 and emission and detection waveguides 3210 and 3220 preferably impact emitted and collected electromagnetic radiation 3002 and 3006. FIG. 22 shows a first embodiment of the angles of intersection, and FIGS. 23A and 23B show a second embodiment of the angles of intersection. Regardless of the embodiment, emission waveguide 3210 transmits electromagnetic radiation generally along a first path 3210*a* to emitter face 3214, and detection waveguide 3220 transmits electromagnetic radiation generally along a second path 3220*a* from detector face 3224. Superficies 3300 preferably includes housing surface 3120 and emitter and detector faces 3214 and 3224. Preferably, first path 3210*a* intersects with superficies 3300 at a first angle $\alpha_1$ and second path 3220*a* intersects with superficies 3300 at a second angle $\alpha_2$. In the case of concave or convex superficies 3300, or superficies 3300 that include projections or recesses, first and second angles $\alpha_1$ and $\alpha_2$ preferably are measured with respect to the tangent to superficies 3300. Emitted electromagnetic radiation 3002 preferably includes at least a part of the electromagnetic radiation that is transmitted along first path 3210*a*, and the electromagnetic radiation transmitted along second path 3220*a* preferably includes at least a part of collected electromagnetic radiation 3006. Preferably, emitted electromagnetic radiation 3002 exits emitter face 3214 within an emission cone 3004, and collected electromagnetic radiation 3006 enters detector face 3224 within an acceptance cone 3008. Emission and acceptance cones 3004 and 3008 preferably include ranges of angles over which electromagnetic radiation is, respectively, emitted by emission waveguide 3210 and accepted by detection waveguide 3220. Typically, each range has a maximum half-angle $\theta_{max}$ that is related to a numerical aperture NA of the corresponding waveguide as follows: NA=$\eta$ sin $\theta_{max}$, where $\eta$ is the refractive index of the material that the electromagnetic radiation is entering (e.g., from emission waveguide 3210) or exiting (e.g., to detection waveguide 3220). The numerical aperture NA of emission or detection optical fibers 3212 or 3222 typically is calculated based on the refractive indices of the optical fiber core ($\eta_{core}$) and optical fiber cladding ($\eta_{clad}$) as follows: NA=$\sqrt{\eta_{core}^2 - \eta_{clad}^2}$. Thus, the ability of a waveguide to emit or accept rays from various angles generally is related to material properties of the waveguide. Ranges of suitable numerical apertures NA for emission or detection waveguides 110 or 120 may vary considerably, e.g., between approximately 0.20 and approximately 0.60. According to one embodiment, individual emission or detection optical fibers 3212 or 3222 preferably have a numerical apertures NA of approximately 0.55. The maximum half-angle $\theta_{max}$ of a cone typically is a measure of an angle between the cone's central axis and conical surface. Accordingly, the maximum half-angle $\theta_{max}$ of emission waveguide 3210 preferably is a measure of the angle formed between a central axis 3004*a* and the conical surface of emission cone 3004, and the maximum half-angle $\theta_{max}$ of detection waveguide 3220 preferably is a measure of the angle formed between a central axis 3008*a* and the conical surface of acceptance cone 3008. The direction of central axis 3004*a* preferably is at a first angle $\beta_1$ with respect to superficies 3300 and the direction of central axis 3008*a* preferably is at a second angle $\beta_2$ with respect to superficies 3300. Therefore, first angle $\beta_1$ preferably indicates the direction of emission cone 3004 and thus also describes the angle of intersection between emitted electromagnetic radiation 3002 and superficies 3300, and second angle $\beta_2$ preferably indicates the direction of acceptance cone 3008 and thus also describes the angle of intersection between collected electromagnetic radiation 3006 and superficies 3300. In the case of concave or convex superficies 3300, or superficies 3300 that include projections or recesses, first and second angles $\beta_1$ and $\beta_2$ preferably are measured with respect to the tangent to superficies 3300.

FIG. 22 shows a generally perpendicular relationship between superficies 3300 and emission and detection waveguides 3210 and 3220. The inventors discovered, inter alia, if first and second angles $\alpha_1$ and $\alpha_2$ preferably are approximately 90 degrees with respect to superficies 3300 then (1) first and second angles $\beta_1$ and $\beta_2$ preferably also tend to be approximately 90 degrees with respect to superficies 3300; (2) emitted electromagnetic radiation 3002 preferably is minimally attenuated at the interface between the skin S and emitter face 3214; and (3) collected electromagnetic radiation 3006 preferably has an improved signal-to-noise ratio. An advantage of having emission waveguide 3210 disposed at an approximately 90 degree angle with respect to superficies 3300 preferably is maximizing the electromagnetic energy that is transferred from along the first path 3210*a* to emitted electromagnetic radiation 3002 at the interface between electromagnetic radiation sensor 3000 and the skin S. Preferably, this transfer of electromagnetic energy may be improved when internal reflection in waveguide 3210 due to emitter face 3214 is minimized. Orienting emitter face 3214 approximately perpendicular to first path 3210*a*, e.g., cleaving and/or polishing emission optical fiber(s) 3212 at approximately 90 degrees with respect to first path 3210*a*, preferably minimizes internal reflection in waveguide 3210. Specifically, less of the electromagnetic radiation transmitted along first path 3210*a* is reflected at emitter face 3214 and more of the electromagnetic radiation transmitted along first path 3210*a* exits emitter face 3214 as emitted electromagnetic radiation 3002. Another advantage of having emission waveguide 3210 disposed at an approximately 90 degree angle with respect to superficies 3300 preferably is increasing the depth below the stratum corneum that emitted electromagnetic radiation 3002 propagates into the skin S because first angle $\beta_1$ also tends to be approximately 90 degrees when first angle $\alpha_1$ is approximately 90 degrees. Preferably, as discussed above with respect to FIGS. 18A-18C and 20A-20C, the predominant electromagnetic radiation paths through the skin S are crescent-shaped and the increased propagation depth of emitted electromagnetic radiation 3002 may improve the signal-to-noise ratio of collected electromagnetic radiation 3006. Thus, according to the first embodiment shown in FIG. 22, emission and detection waveguides 3210 and 3220 preferably are disposed in a housing 3100 of electromagnetic radiation sensor 3000 such that first and second paths 3210*a* and 3220*a* are approximately perpendicular to superficies 3300 for increasing the optical power $\Phi_2$ and for improving the signal-to-noise ratio of collected electromagnetic radiation 3006.

FIGS. 23A and 23B show an oblique angular relationship between superficies 3300 and emission and detection waveguides 3210 and 3220. Preferably, at least one of first and second angles $\alpha_1$ and $\alpha_2$ are oblique with respect to superficies 3300. First and second angles $\alpha_1$ and $\alpha_2$ preferably are both oblique and inclined in generally similar directions with respect to superficies 3300. According to one embodiment, the difference between the first and second angles $\alpha_1$ and $\alpha_2$ preferably is between approximately 15 degrees and approximately 45 degrees. Preferably, the first angle $\alpha_1$ is approximately 30 degrees less than the second angle $\alpha_2$. According to other embodiments, first angle $\alpha_1$ ranges between approximately 50 degrees and approximately 70 degrees, and second angle $\alpha_2$ ranges between approximately 75 degrees and approximately 95 degrees. Preferably, first angle $\alpha_1$ is approximately 60 degrees and second angle $\alpha_2$ ranges between approximately 80 degrees and approximately 90 degrees. A consequence of first angle $\alpha_1$ being oblique with respect to superficies 3300 is that a portion of the electromagnetic radiation transmitted along first path 3210a may be reflected at emitter face 3214 in a direction 3210b rather than exiting emitter face 3214 as emitted electromagnetic radiation 3002. Another consequence is that refraction may occur at the interface between electromagnetic radiation sensor 3000 and the skin S because the emission and detection waveguides 3210 and 3220 typically have different refractive indices with respect to the skin S. Accordingly, first angles $\alpha_1$ and $\beta_1$ would likely be unequal and second angles $\alpha_2$ and $\beta_2$ would also likely be unequal.

FIG. 23B illustrates a technique for geometrically interpreting the interplay between emitted electromagnetic radiation 3002 and collected electromagnetic radiation 3006 when emission and detection waveguides 3210 and 3220 are obliquely disposed with respect to superficies 3300. Preferably, emission cone 3004 represents the range of angles over which emitted electromagnetic radiation 3002 exits emitter face 3214, and acceptance cone 3008 represents the range of angles over which collected electromagnetic radiation 3006 enters detector face 3224. Projecting emission and acceptance cones 3004 and 3008 to a common depth below the stratum corneum of the skin S preferably maps out first and second patterns 3004b and 3008b, respectively, which are shown with different hatching in FIG. 23B. Preferably, the projections of emission and acceptance cones 3004 and 3008 include a locus of common points where first and second patterns 3004b and 3008b overlap, which accordingly is illustrated with cross-hatching in FIG. 23B. In principle, the locus of common points shared by the projections of emission and acceptance cones 3004 and 3008 includes tissue that preferably is a focus of electromagnetic radiation sensor 3000 for monitoring anatomical changes over time. Accordingly, an advantage of having emission waveguide 3210 and/or detection waveguide 3220 disposed at an oblique angle with respect to superficies 3300 preferably is focusing electromagnetic radiation sensor 3000 at a particular range of depths below the stratum corneum of the skin S and/or steering electromagnetic radiation sensor 3000 in a particular relative direction. In practice, electromagnetic radiation propagating through the skin S is reflected, scattered and otherwise redirected such that there is a low probability of generally straight-line propagation that is depicted by the projections of emission and detection cones 3004 and 3008. Accordingly, FIG. 23B preferably is a geometric interpretation of the potential for electromagnetic radiation to propagate to a particular range of depths or in a particular relative direction.

Thus, the angles of intersection between superficies 3300 and emission and detection waveguides 3210 and 3220 preferably impact emitted and collected electromagnetic radiation 3002 and 3006 of electromagnetic radiation sensor 3000. Preferably, suitable angles of intersection that (i) improve the optical power $\Phi_2$; (ii) improve the signal-to-noise ratio of collected electromagnetic radiation 3006; and/or (iii) focus electromagnetic radiation sensor 3000 at particular depths/directions include, e.g., approximately perpendicular angles and oblique angles.

The discoveries made by the inventors include, inter alia, configurations of an electromagnetic radiation sensor that preferably increase the optical power of emitted electromagnetic radiation and/or improve the signal-to-noise ratio of collected electromagnetic radiation. Examples of suitable configurations include certain superficies geometries, certain superficies topographies (e.g., superficies 3300 including projections or recesses), and certain angular orientations of emission and detection waveguides. Preferably, suitable configurations include combinations of superficies geometries, superficies topographies, and/or angular orientations of the waveguides. According to one embodiment, an electromagnetic radiation sensor has a configuration that includes approximately 4 millimeters between waveguides, a convex superficies, and waveguides that intersect the superficies at approximately 90 degrees.

An electromagnetic radiation sensor according to the present disclosure preferably may be used, for example, (1) as an aid in detecting at least one of infiltration and extravasation; (2) to monitor anatomical changes in perivascular tissue; or (3) to emit and collect transcutaneous electromagnetic signals. The discoveries made by the inventors include, inter alia, that sensor configuration including geometry (e.g., shape and spacing), topography, and angles of transcutaneous electromagnetic signal emission and detection affect the accurate indications anatomical changes in perivascular tissue, including infiltration/extravasation events. For example, the discoveries made by the inventors include that the configuration of an electromagnetic radiation sensor is related to the accuracy of the sensor for aiding in diagnosing at least one of infiltration and extravasation in Animalia tissue.

Sensors according to the present disclosure preferably are manufactured by certain methods that may vary. Preferably, operations included in the manufacturing method may be performed in certain sequences that also may vary. According to one embodiment, a sensor manufacturing method preferably includes molding first and second housing portions 3102 and 3104 (see FIG. 17), which define an interior volume 3110. Preferably, superficies 3300 is molded with first housing portion 3102. At least one emission optical fiber 3212 and at least one detection optical fiber 3222 preferably extend through interior volume 3110. Preferably, portions of emission and detection optical fibers 3212 and 3222 are disposed in interior volume 3110. First and second housing portions 3102 and 3104 preferably are coupled together. Preferably, filler 3150, e.g., epoxy, is injected via a fill hole (not shown) in housing 3100 to occlude internal volume 3110 and cincture the portions of emission and detection optical fibers 3212 and 3222 in internal volume 3110. Portions of emission and detection optical fibers 3212 and 3222 disposed outside housing 3100 preferably are cleaved generally proximate to superficies 3300. Preferably, end faces of emission and detection optical fibers 3212 and 3222 are polished substantially smooth with housing surface 3120. According to one embodiment, each individual point on end faces of emission optical fibers 3212 preferably is disposed a distance not less than 3 millimeters and not more than 5 millimeters from each individual point on end faces detection optical fibers 3222.

According to other embodiments, first housing portion 3102 preferably is supported with housing surface 3120 disposed orthogonal with respect to gravity, and portions of emission and detection optical fibers 3212 and 3222 inside interior volume 3110 are fixed with respect to first housing portion 3102. The first and second angles of intersection $\alpha_1$ and α₂ between superficies 3300 and emission and detection optical fibers 3212 and 3222 therefore preferably are approximately 90 degrees. According to other embodiments, at least one of emission and detection optical fibers 3212 and 3222 is fixed relative to first housing portion 3102 at an oblique angle of intersection with respect to superficies 3300. According to other embodiments, occluding internal volume 3110 preferably includes heating at least one of housing 3100, emission optical fiber 3212, and detection optical fiber 3222. Preferably, heating facilitates flowing filler 3150 in interior volume 3110.

Figure 24:
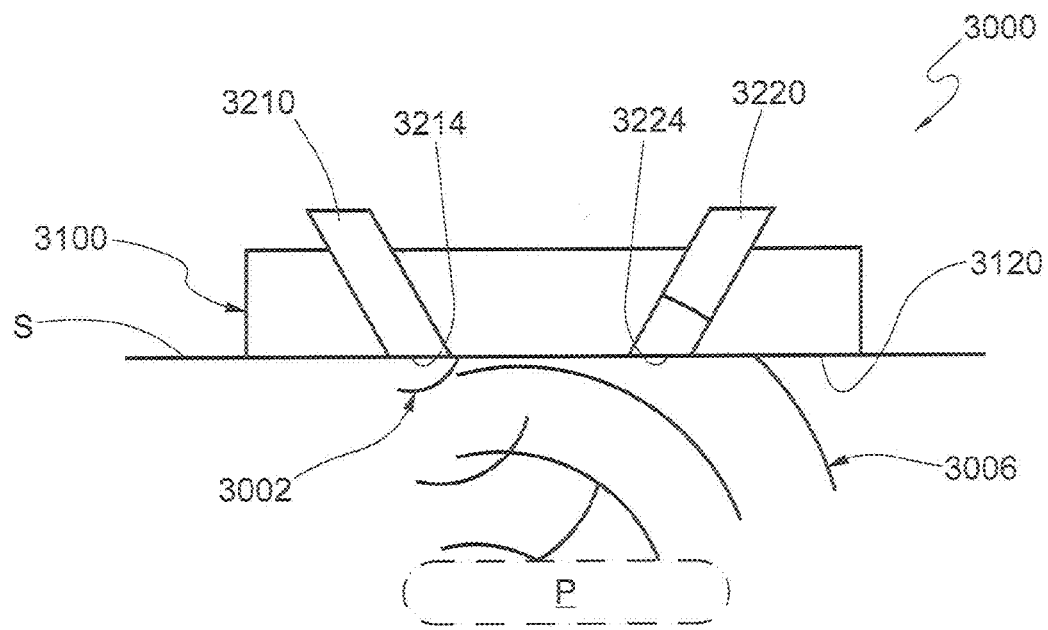
FIG. 24 is a schematic cross-section view illustrating an electromagnetic radiation sensor according to the present disclosure. The electromagnetic radiation sensor is shown contiguously engaging Animalia skin.

Electromagnetic energy sensor 3000 preferably is positioned in close proximity to the skin S. As the terminology is used herein, "close proximity" of electromagnetic energy sensor 3000 with respect to the skin S preferably refers to a relative arrangement that minimizes gaps between superficies 3300 and the epidermis E of the skin S. According to one embodiment, electromagnetic energy sensor 3000 contiguously engages the skin S as shown in FIG. 24.

The inventors discovered a problem regarding accurately identifying the occurrence of infiltration or extravasation because of a relatively low signal-to-noise ratio of collected electromagnetic radiation 3006. In particular, the inventors discovered a problem regarding a relatively large amount of noise in collected electromagnetic radiation 3006 that obscures signals indicative of infiltration/extravasation events. Another discovery by the inventors is that the amount of noise in collected electromagnetic radiation 3006 tends to correspond with the degree of patient activity. In particular, the inventors discovered that collected electromagnetic radiation 3006 tends to have a relatively lower signal-to-noise ratio among patients that are more active, e.g., restless, fidgety, etc., and that collected electromagnetic radiation 3006 tends to have a relatively higher signal-to-noise ratio among patients that were less active, e.g., calm, sleeping, etc.

The inventors also discovered that a source of the problem is an imperfect cavity that may unavoidably and/or intermittently occur between superficies 3300 and the skin S. As the terminology is used herein, "imperfect cavity" preferably refers to a generally confined space that at least partially reflects electromagnetic radiation. In particular, the inventors discovered that the source of the problem is portions of emitted electromagnetic radiation 3002 and/or collected electromagnetic radiation 3006 being reflected in the imperfect cavity between superficies 3300 and the skin S.

Figure 25:
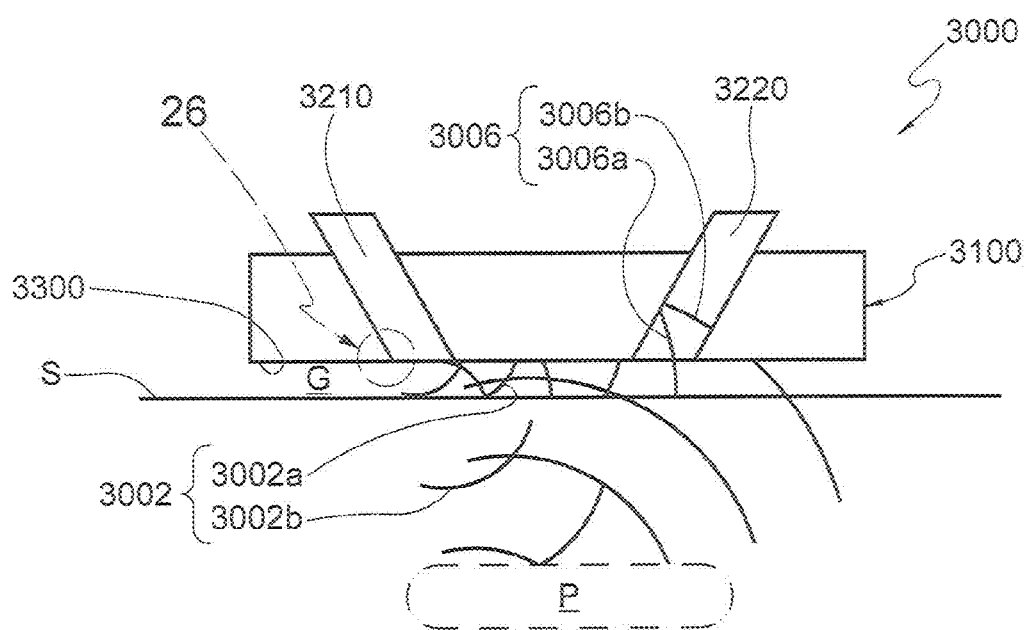
FIG. 25 is a schematic cross-section view explaining separation between the Animalia skin and the electromagnetic energy sensor shown in FIG. 24.

FIG. 25 illustrates the source of the problem discovered by the inventors. Specifically, FIG. 25 shows a cavity G disposed between electromagnetic energy sensor 3000 and the skin S. The size, shape, proportions, etc. of the cavity G are generally overemphasized in FIG. 25 to facilitate describing the source of the problem discovered by the inventors. Referring also to FIG. 17, transcutaneous electromagnetic radiation 3002b preferably passes through the cavity G and passes through the target area of the skin S toward the perivascular tissue P. Cutaneous electromagnetic radiation 3002a generally is reflected in the cavity G between the cutaneous tissue C and superficies 3300. Preferably, signal component 3006b includes at least some of transcutaneous electromagnetic radiation 3002b that is at least one of reflected, scattered or otherwise redirected from the perivascular tissue P before passing through the skin S, passing through the cavity G, and entering detection waveguide 3220 via detector face 3224. Noise component 3006a generally includes at least some of cutaneous electromagnetic radiation 3002a that is reflected in the cavity G before entering detection waveguide 3220 via detector face 3224.

Preferably, signal component 3006b provides an indication that an infiltration/extravasation event is occurring whereas noise component 3006a tends to obscure an indication that an infiltration/extravasation event is occurring. Thus, the inventors discovered, inter alia, that a cavity between superficies 3300 and the skin S affects the signal-to-noise ratio of collected electromagnetic radiation 3006.

Figure 26A:
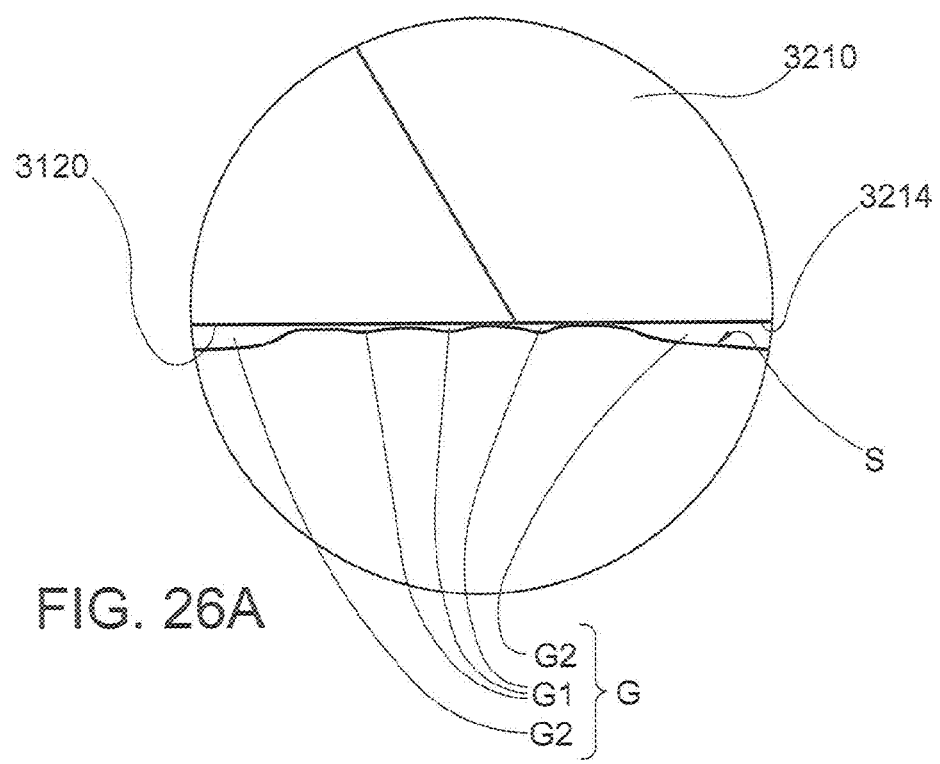
FIGS. 26A and 26B are schematic cross-section views illustrating alternative details of area XXVI shown in FIG. 25.
Figure 26B:
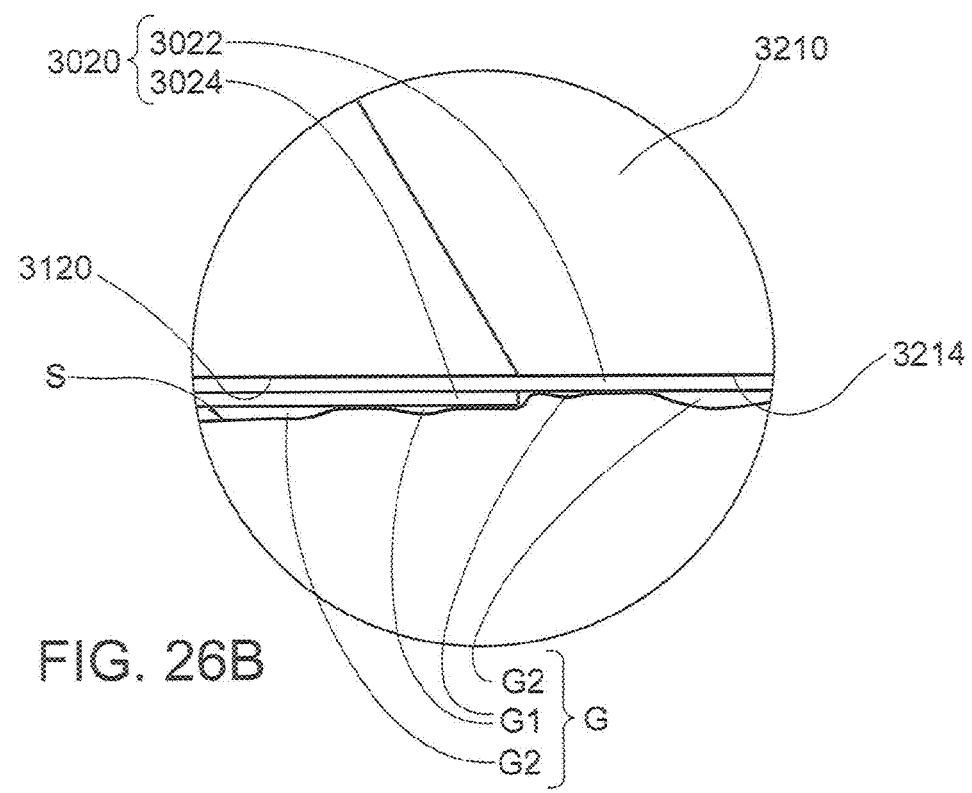

FIGS. 26A and 26B illustrate that the cavity G preferably includes one or an aggregation of individual gaps. FIG. 26A shows individual gaps between superficies 3300 and the skin S that, taken in the aggregate, preferably make up the cavity G. Preferably, the individual gaps may range in size between approximately microscopic gaps G1 (three are indicated in FIG. 26A) and approximately macroscopic gaps G2 (two are indicated in FIG. 26A). It is believed that approximately microscopic gaps G1 may be due at least in part to epidermal contours of the skin S and/or hair on the skin S, and approximately macroscopic gaps G2 may be due at least in part to relative movement between superficies 3300 and the skin S. Patient activity is an example of an occurrence that may cause the relative movement that results in approximately macroscopic gaps G2 between superficies 3300 and the skin S.

FIG. 26B shows electromagnetic energy sensor 3000 preferably isolated from the skin S by a foundation 3130. Preferably, foundation 3130 contiguously engages superficies 3300 and contiguously engages the skin S. Accordingly, the cavity G between foundation 3130 and the skin S preferably includes an aggregation of (1) approximately microscopic gaps G1 (two are indicated in FIG. 26B); and (2) approximately macroscopic gaps G2 (two are indicated in FIG. 26B). Foundation 3130 preferably is coupled with respect to electromagnetic energy sensor 3000 and includes a panel 3132 and/or adhesive 3134. Preferably, panel 3132 includes a layer disposed between electromagnetic energy sensor 3000 and the skin S. Panel 3132 preferably includes Tegaderm™, manufactured by 3M (St. Paul, Minn., USA), REACTIC™, manufactured by Smith & Nephew (London, UK), or another polymer film, e.g., polyurethane film, that is substantially impervious to solids, liquids, microorganisms and/or viruses. Preferably, panel 3132 is biocompatible, breathable, and/or transparent or translucent with respect to visible light. Panel 3132 preferably is generally transparent with respect to emitted and collected electromagnetic radiation 3002 and 3006. Preferably, adhesive 3134 bonds at least one of panel 3132 and electromagnetic energy sensor 3000 to the skin S. Adhesive 3134 preferably includes an acrylic adhesive, a synthetic rubber adhesive, or another biocompatible, medical grade adhesive. Preferably, adhesive 3134 minimally affects emitted and collected electromagnetic radiation 3002 and 3006. According to one embodiment, as shown in FIG. 26B, adhesive 3134 preferably is omitted where emitted and collected electromagnetic radiation 3002 and 3006 penetrate foundation 3130, e.g., underlying emitter and detector faces 3214 and 3224.

Figure 27:
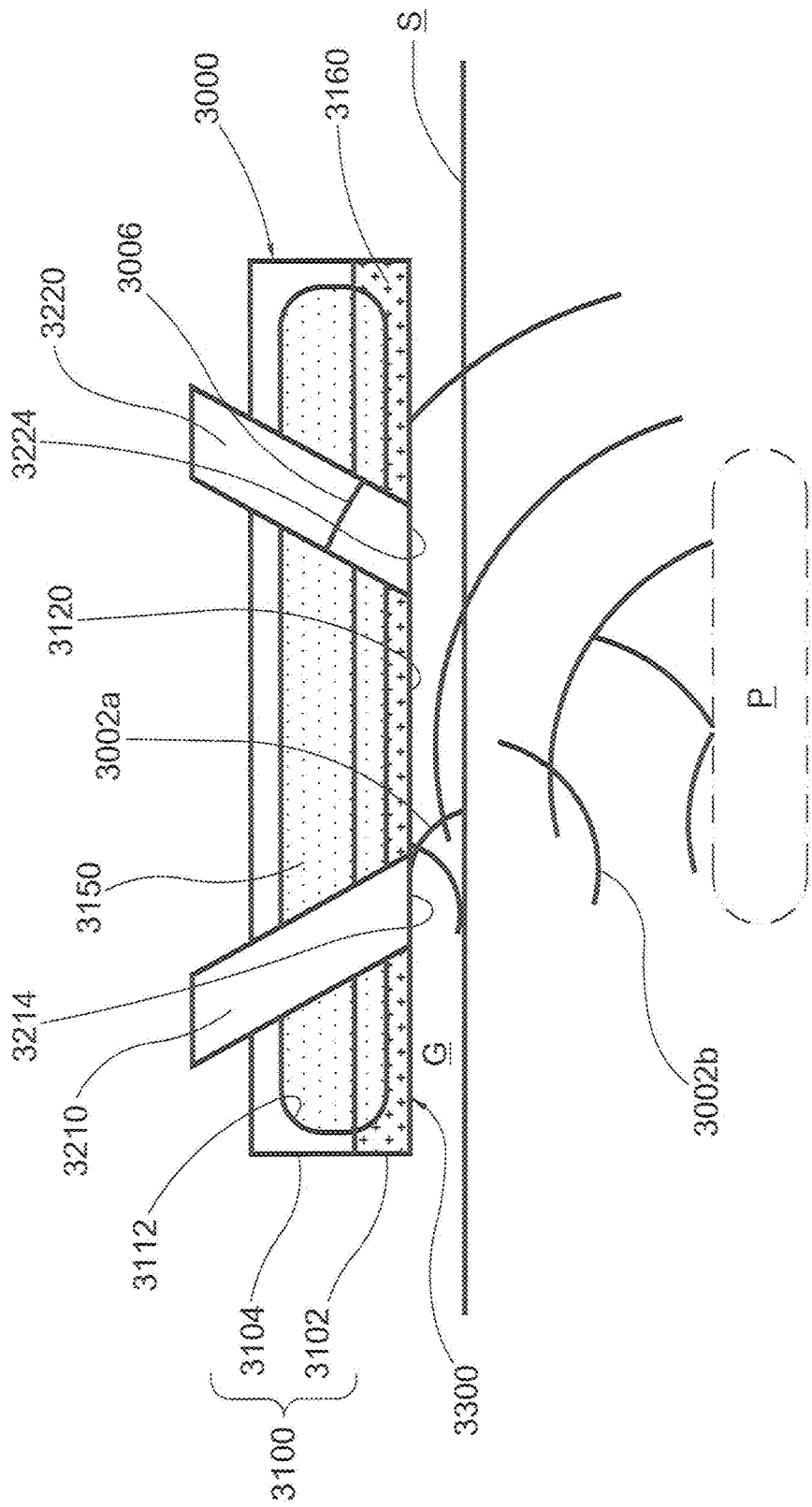
FIG. 27 is a schematic cross-section view illustrating an electromagnetic radiation sensor according to the present disclosure. The electromagnetic radiation sensor is shown separated from Animalia skin.

FIG. 27 shows a housing 3100 according to the present disclosure including an electromagnetic radiation absorber 3160. Preferably, emission and detection waveguides 3210 and 3220 extend through interior volume 3110 that is generally defined by an interior wall 3112 of housing 3100. Housing 3100 preferably includes a biocompatible material, e.g., polycarbonate, polypropylene, polyethylene, acrylonitrile butadiene styrene, or another polymer material. Preferably, filler 3150, e.g., epoxy or another potting material, fills interior volume 3110 around emission and detection waveguides 3210 and 3220. According to one embodiment, filler 3150 preferably cinctures emission and detection optical fibers 3212 and 3222 disposed in interior volume 3110. Preferably, housing 3100 includes surface 3120 that confronts the skin S and cinctures emitter and detector faces 3214 and 3224. Accordingly, superficies 3300 of electromagnetic energy sensor 3000 preferably includes emitter face 3214, detector face 3224 and surface 3120.

Absorber 3160 preferably absorbs electromagnetic radiation that impinges on surface 3120. As the terminology is used herein, "absorb" or "absorption" preferably refer to transforming electromagnetic radiation propagating in a material to another form of energy, such as heat. Preferably, absorber 3160 absorbs wavelengths of electromagnetic radiation that generally correspond to the wavelengths of emitted and collected electromagnetic radiation 3002 and 3006. According to one embodiment, absorber 3160 preferably absorbs electromagnetic radiation in the near-infrared portion of the electromagnetic spectrum. Absorber 3160 may additionally or alternatively absorb wavelengths in other parts of the electromagnetic radiation spectrum, e.g., visible light, short-wavelength infrared, mid-wavelength infrared, long-wavelength infrared, or far infrared. According to one embodiment, absorber 3160 absorbs at least 50% and preferably 90% or more of the electromagnetic radiation that impinges on surface 3120.

Absorber 3160 preferably includes a variety of form factors for inclusion with housing 3100. Preferably, absorber 3160 includes at least one of a film, a powder, a pigment, a dye, or ink. Film or ink preferably are applied on surface 3120, and powder, pigment or dye preferably are incorporated, e.g., dispersed, in the composition of housing 3100. FIG. 27 shows absorber 3160 preferably is included in first housing portion 3102; however, absorber 3160 or another electromagnetic radiation absorbing material may also be included in second housing portion 3104 and/or filler 3150. Examples of absorbers 3160 that are suitable for absorbing near-infrared electromagnetic radiation preferably include at least one of antimony-tin oxide, carbon black, copper phosphate, copper pyrophosphate, illite, indium-tin oxide, kaolin, lanthanum hexaboride, montmorillonite, nickel dithiolene dye, palladium dithiolene dye, platinum dithiolene dye, tungsten oxide, and tungsten trioxide.

Absorber 3160 preferably improves the signal-to-noise ratio of received electromagnetic radiation 3006 by reducing noise component 3006a. Preferably, electromagnetic energy that impinges on surface 3120 is absorbed rather than being reflected in the cavity G and therefore does not propagate further, e.g., toward detector face 3224. According to one embodiment, absorber 3160 preferably substantially attenuates cutaneous electromagnetic radiation 3002a and noise component 3006a as compared to electromagnetic energy sensor 3000 shown in FIG. 25.

Electromagnetic energy sensor 3000 preferably may be used, for example, (1) as an aid in detecting at least one of infiltration and extravasation; (2) to identify an anatomical change in perivascular tissue; or (3) to analyze a transcutaneous electromagnetic signal. Emitted electromagnetic radiation 3002 preferably propagates from emitter face 3214 through foundation 3130 and/or cavity G, if either of these is disposed in the path of emitted electromagnetic radiation 3002, toward the target area of the skin S. According to one embodiment, emitted electromagnetic radiation 3002 divides into cutaneous electromagnetic radiation 3002a and transcutaneous electromagnetic radiation 3002b in the cavity G.

Cutaneous electromagnetic radiation 3002a may be initially reflected in cavity G, but preferably is generally absorbed by absorber 3160. According to one embodiment, absorber 3160 absorbs at least 50% and preferably 90% or more of cutaneous electromagnetic radiation 3002a that impinges on surface 3120. Accordingly, noise component 3006a due to cutaneous electromagnetic radiation 3002a preferably is substantially eliminated or at least reduced by absorber 3160.

Transcutaneous electromagnetic radiation 3002b preferably propagates through the skin S toward the perivascular tissue P. Preferably, at least a portion of transcutaneous portion 3002b is at least one of reflected, scattered or otherwise redirected from the perivascular tissue P toward the target area of the skin S as signal component 3006b. After propagating through the target area of the skin S, signal component 3006b preferably further propagates through the cavity G and foundation 3130, if either of these is disposed in the path of signal component 3006b, toward detector face 3224. Preferably, detector face 3224 collects signal component 3006b and detection waveguide 3220 transmits collected electromagnetic radiation 3006 to patient monitoring device 6000. Preferably, patient monitoring device 6000 analyzes collected electromagnetic radiation 3006 to, for example, identify anatomical changes in perivascular tissue and/or aid in detecting an infiltration/extravasation event.

Absorber 3160 preferably also absorbs other noise in addition to that resulting from cutaneous portion 3002a. For example, absorber 3160 preferably also absorbs a portion of signal component 3006b that impinges on surface 3120 rather than being collected by detector face 3224.

Thus, absorber 3160 preferably improves the signal-to-noise ratio of collected electromagnetic radiation 3006 by absorbing noise component 3006a. Preferably, reducing noise component 3006a in collected electromagnetic radiation 3006 makes it easier for patient monitoring device 6000 to analyze signal 3006b in collected electromagnetic radiation 3006.

Changes in the size and/or volume of cavity G preferably may also be used to monitor patient activity and/or verify inspections by caregivers. Preferably, information regarding the occurrence of patient posture change may be detected by electromagnetic energy sensor 3000. Accordingly, this information may aid a caregiver in evaluating if a patient is obsessed with or distracted by cannula 20 and therefore at greater risk of disrupting the patient's infusion therapy. Similarly, electromagnetic energy sensor 3000 preferably may be used to detect caregiver examinations of the target area of the skin and/or the cannulation site N. Preferably, a caregiver periodically examines the patient during infusion therapy for indications of infiltration/extravasation events. These examinations preferably include touching and/or palpating the target area of the patient's skin. These actions by the caregiver tend to cause relative movement between electromagnetic energy sensor 3000 and the skin S. Accordingly, a record of collected electromagnetic radiation 3006 preferably includes the occurrences over time of caregiver inspections.

Sensor Cable

Electromagnetic radiation sensor 3000 may be coupled to patient monitoring device 6000 via sensor cable 5000. According to some embodiments, electromagnetic radiation sensor 3000 and patient monitoring device 6000 may be coupled wirelessly rather than via sensor cable 5000, or electromagnetic radiation sensor 3000 may incorporate certain features of patient monitoring device 6000.

Figure 28A:
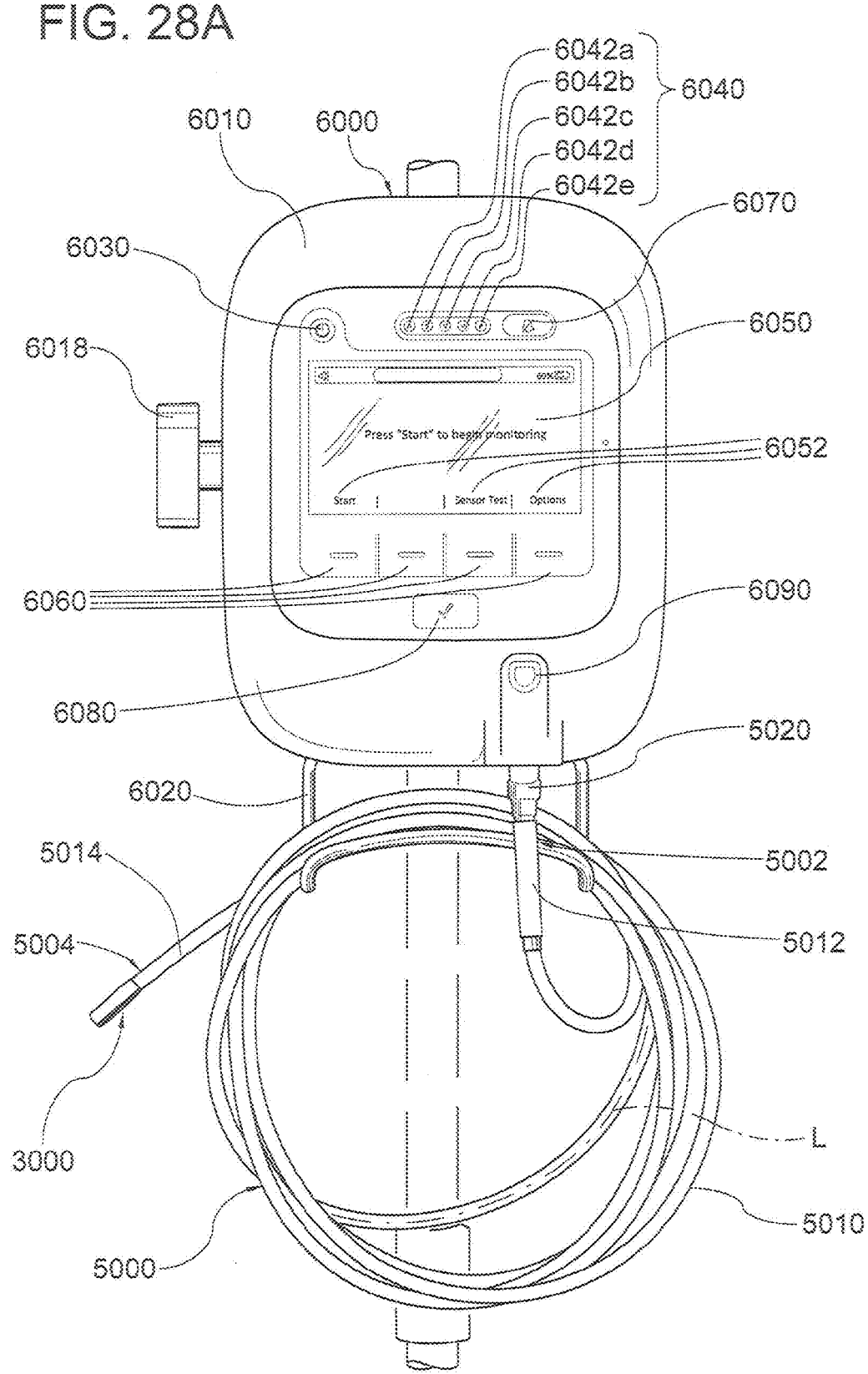
FIGS. 28A-28C are perspective views illustrating a patient monitoring device according to the present disclosure.
Figure 28B:
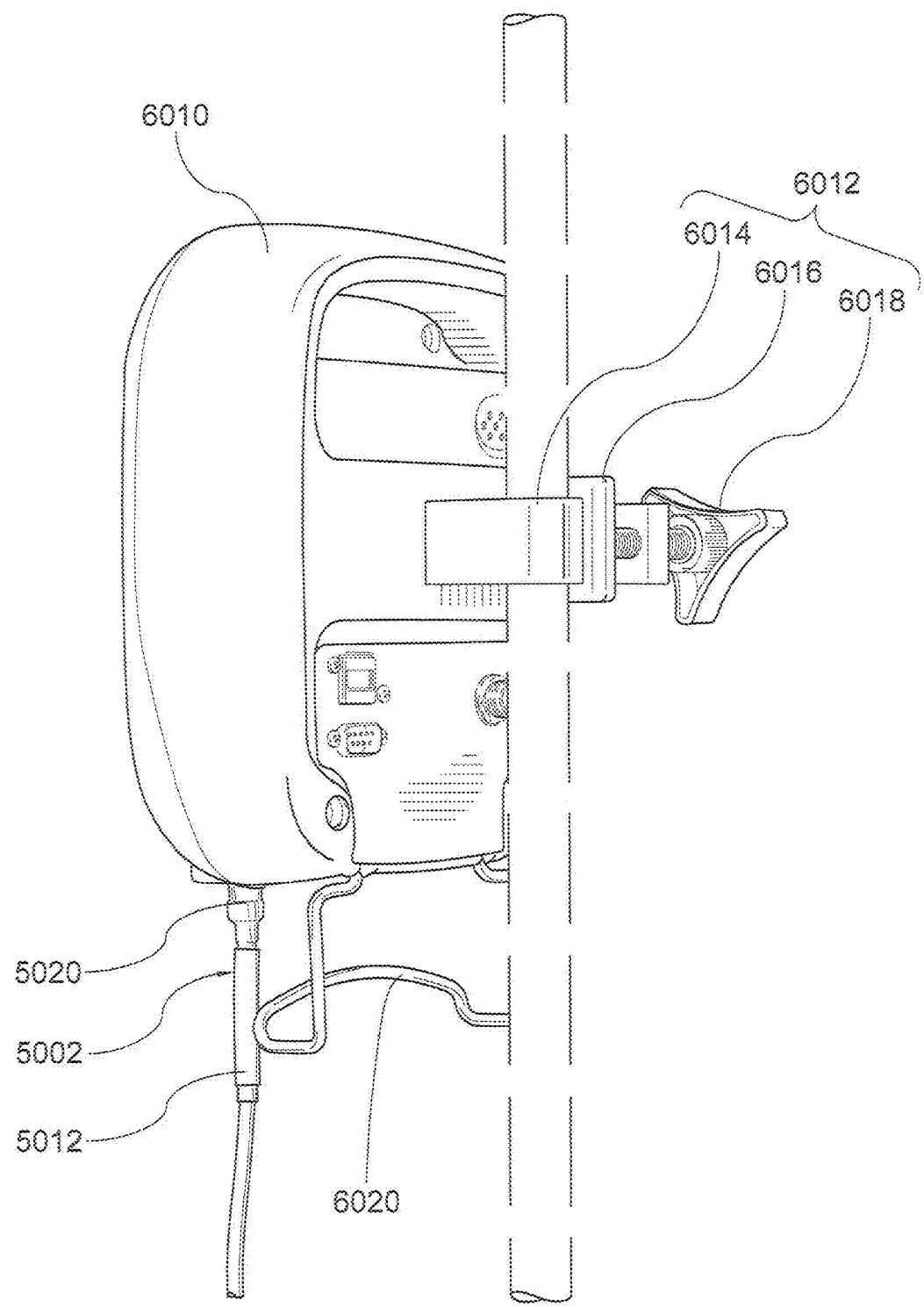
Figure 28C:
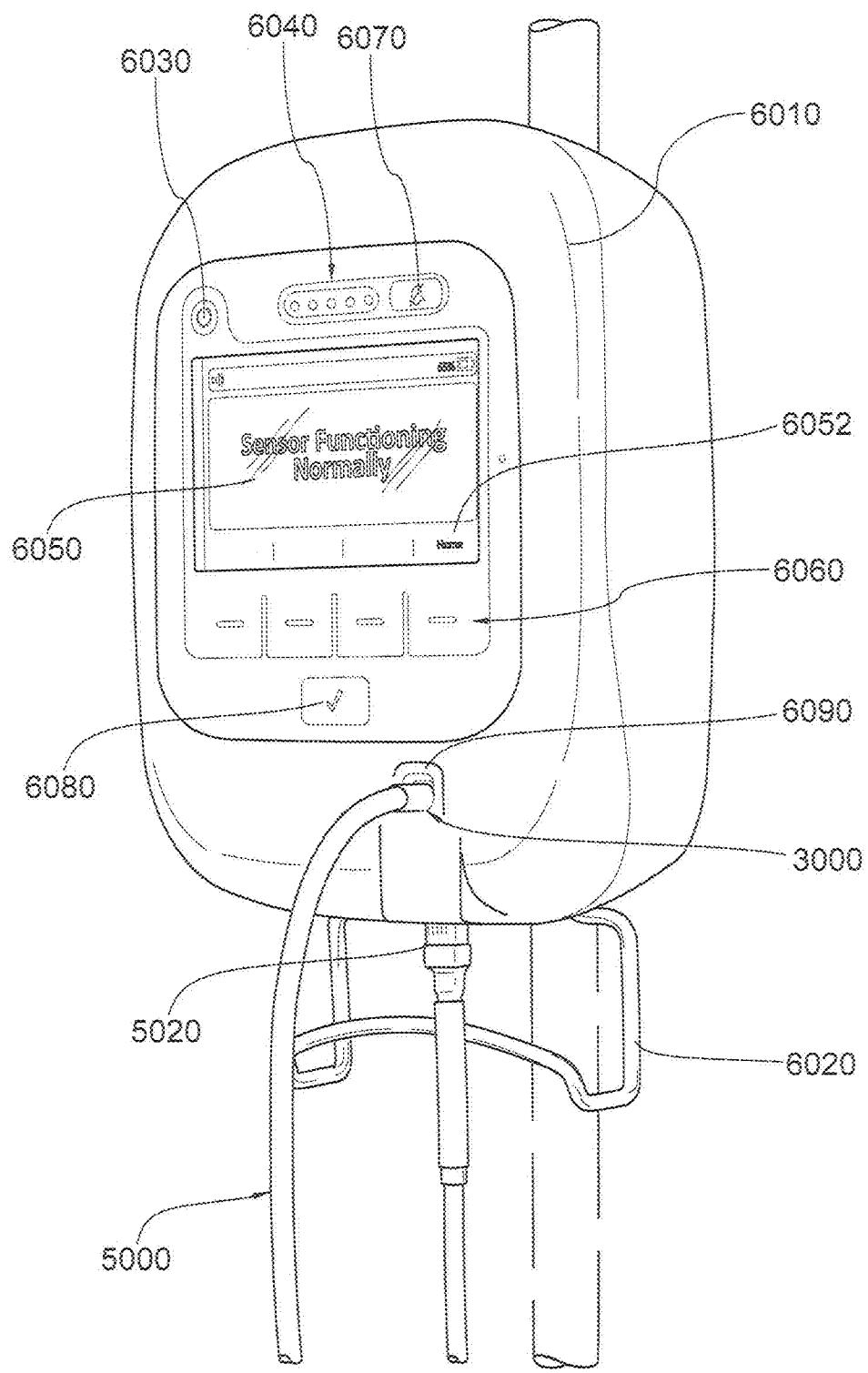

FIGS. 28A-28C illustrate an embodiment of sensor cable 5000 according to the present disclosure. Sensor cable 5000 preferably provides transmission paths for first and second light signals between patient monitoring device 6000 and electromagnetic radiation sensor 3000. According to one embodiment, sets of emission and detection optical fibers 3212 and 3222 preferably extend in sensor cable 5000 along a longitudinal axis L between first and second ends 5002 and 5004. Preferably, first end 5002 is proximate to patient monitoring device 6000 and second end 5004 is proximate to electromagnetic radiation sensor 3000. A sheath 5010 preferably cinctures sets of emission and detection optical fibers 3212 and 3222 along the longitudinal axis L between first and second ends 5002 and 5004. Preferably, sheath 5010 includes a first end 5012 coupled to a plug 5020 and includes a second end 5014 coupled to electromagnetic radiation sensor 3000. Plug 5020 preferably facilitates consistent optical coupling and recoupling with patient monitoring device 6000.

Sensor cable 5000 preferably provides a conduit for emission and detection optical fibers 3212 and 3222. According to one embodiment, each set includes several hundred optical fibers and preferably includes approximately 600 individual borosilicate optical fibers having an approximately 50 micron diameter, a numerical aperture NA of approximately 0.55, and a low hydroxyl group content, e.g., less than 50 parts per million and preferably less than 20 parts per million. One example of a suitable optical fiber material is Glass 8250 manufacture by Schott North America, Inc. (Elmsford, N.Y., US). According to other embodiments, each set may include different numbers of optical fibers possibly with different diameters, higher or lower numerical apertures, and different hydroxyl group contents. According to other embodiments, the optical fiber material may include different types of glass or plastic. The material of sheath 5010 preferably includes a medical grade thermoplastic polyurethane, e.g., Tecoflex®, manufactured by The Lubrizol Corporation (Wickliffe, Ohio, US). According to one embodiment, sheath 5010 preferably is extruded around the sets of emission and detection optical fibers 3212 and 3222. According to other embodiments, one set of emission or detection optical fibers 3212 or 3222 may be cinctured in a jacket (not shown) disposed in sheath 5010. According to other embodiments, sheath 5010 may include an element to avoid crushing emission and detection optical fibers 3212 and/or to limit the minimum bend radius of sensor cable 5000.

Patient Monitoring Device

Patient monitoring device 6000 preferably is suitable for controlling pulses of first and second emitted electromagnetic radiation 3002 and 3012, and for analyzing corresponding pulses of optical power $\Phi_6$ and $\Phi_{16}$ corresponding to first and second collected electromagnetic radiation 3006 and 3016. Preferably, the optical power $\Phi_6$ changes over time in response to (i) fluid infusing the perivascular tissue P; and (ii) changing tissue blood volume along the monitoring path of first emitted and collected electromagnetic radiation 3002 and 3006. Changes over time in the optical power $\Phi_{16}$ preferably distinguish between fluid infusing the perivascular tissue P or changing tissue blood volume. Accordingly, second emitted and collected electromagnetic radiation 3012 and 3016 preferably (i) verify that an infiltration/extravasation examination is indicated based on an anatomic change due to fluid infusing the perivascular tissue P; and (ii) eliminate or at least substantially mitigate false alerts to perform an infiltration/extravasation examination based on changing tissue blood volume.

FIGS. 28A-28C illustrate the exterior of patient monitoring device 6000 according to one embodiment of the present disclosure. Patient monitoring device 6000 preferably includes a shell 6010 supported on a pole by a clamp 6012. Preferably, shell 6010 includes an exterior surface and defines an interior space. According to one embodiment, clamp 6012 preferably is disposed on the exterior of shell 6010 and includes a fixed jaw 6014 and a moving jaw 6016. An actuator 6018, e.g., a knob and threaded rod, preferably displaces moving jaw 6016 relative to fixed jaw 6014 for gripping and releasing clamp 6012 with respect to the pole. Preferably, a bail 6020 is coupled to shell 6010 for capturing sensor cable 5000, e.g., when dressing 1000 is in the second arrangement. According to the embodiment shown in FIGS. 28A-28C, bail 6020 includes a hook coupled to shell 6010 at a plurality of junctures. According to other embodiments, bail 6020 may be coupled to shell 6010 at a single juncture or a basket or net slung from shell 6010 may be used to capture at least a portion of sensor cable 5000.

Patient monitoring device 6000 preferably includes a number of features disposed on the exterior of shell 6010. Preferably, patient monitoring device 6000 includes a power button 6030, an indicator set 6040, a display 6050, a set of soft keys 6060, a mute button 6070, a check button 6080 and a test port 6090. According to the embodiment shown in FIG. 28A, these features preferably are disposed on the front of shell 6010. Pressing power button 6030 preferably toggles ON and OFF patient monitoring device 6000.

Patient monitoring device 6000 preferably provides status reports of varying detail. Preferably, indicator set 6040 provides a basic status report and display 6050 provides a more detailed status report. According to one embodiment, indicator set 6040 includes a set of multi-color light emitting diodes 6042a-6042e providing a visible indication of at least one of three states of patient monitoring device 6000. A first state of patient monitoring device 6000 preferably includes all of multi-color light emitting diodes 6042a-6042e illuminating a first color, e.g., green. Preferably, the first state is characterized by actively monitoring for indications of infiltration or extravasation without identifying a cause for alerting a healthcare giver to evaluate the patient. A second state of patient monitoring device 6000 preferably includes all of multi-color light emitting diodes 6042a-6042e illuminating a second color, e.g., yellow. Preferably, the second state is characterized by identifying a cause for alerting the healthcare giver to evaluate the operation of system 100 with respect to the patient. For example, the second state may be indicated if the operation of system 100 is being disrupted because the patient is pulling on sensor cable 5000. A third state of patient monitoring device 6000 preferably includes all of multi-color light emitting diodes 6042a-6042e illuminating a third color, e.g., red. Preferably, the third state is characterized by patient monitoring device 6000 alerting the healthcare giver to perform an infiltration/extravasation examination. According to other embodiments, the number as well as color(s) of multi-color light emitting diodes 6042a-6042e that are illuminated may provide information regarding, for example, duration or intensity of an event that is cause for alerting a healthcare giver.

Display 6050 preferably provides detailed information regarding the use, status, and alarms of patient monitoring device 6000. Preferably, display 6050 includes color, alphanumeric characters, graphs, icons and images to convey setup and operating instructions, system maintenance and malfunction notices, system configuration statements, healthcare giver alerts, historical records, etc. According to one embodiment, display 6050 preferably displays individual labels 6052 describing a function assigned to a corresponding soft key 6060. According to other embodiments, display 6050 preferably facilitates quantifying with precision when an identifiable event occurred, its duration, its magnitude, whether an alert was issued, and the corresponding type of alert.

Mute button 6070 and check button 6080 preferably are hard keys having regularly assigned functions. Preferably, mute button 6070 temporarily silences an audible alarm. According to one embodiment, a healthcare giver preferably silences the audible alarm while performing an infiltration/extravasation examination. Preferably, the function of mute button 6070 is temporary because disabling rather than silencing the audible alarm may be detrimental to the future effectiveness of patient monitoring device 6000. Check button 6080 preferably includes one or more regularly assigned functions, e.g., registering periodic examinations of the cannulation site N. According to one embodiment, check button 6080 is preferably pressed each time a healthcare giver performs an examination of the cannulation site N. Preferably, the examination is registered in a historical record maintained by patient monitoring device 6000. According to other embodiments, the historical record may be reviewed on display 6050 and/or the historical record may be transferred off patient monitoring device 6000 to a recordkeeping system that maintains a generally comprehensive chronicle of the patient's treatment(s).

Patient monitoring device 6000 preferably includes a test arrangement for verifying the operation and calibration of system 100. According to patient monitoring device 6000 shown in FIG. 28C, the test arrangement includes preferably inserting electromagnetic radiation sensor 3000 in test port 6090, e.g., prior to electromagnetic radiation sensor 3000 being coupled with dressing 1000 in the first arrangement. Preferably, collected electromagnetic radiation 3006 in the test arrangement includes a portion of emitted electromagnetic radiation 3002 that is redirected by an optically standard material disposed in test port 6090. According to one embodiment, the optically standard material preferably includes Spectralon®, manufactured by Labsphere, Inc. (North Sutton, N.H., US), or another material having high diffuse reflectance. Preferably, collected electromagnetic radiation 3006 is collected by detector face 3224 and the corresponding light signal is transmitted via detection waveguide 3220 and plug 5020 to patient monitoring device 6000. The light signal is preferably compared with accepted calibration values. A satisfactory comparison preferably results in an affirmative indication by at least one of indicator set 6040 and display 6050; whereas, display 6050 may present instructions for additional diagnostic routines and/or guidance for recalibrating or repairing system 100 if the result is an unsatisfactory comparison.

The test arrangement shown in FIG. 28C is preferably a generally passive system for verifying the operation and calibration of system 100. According to other embodiments of patient monitoring device 6000, an active testing system preferably includes a light detector to measure the optical power $\Phi_2$ and a light source to mimic collected electromagnetic radiation 3006.

Figure 29:
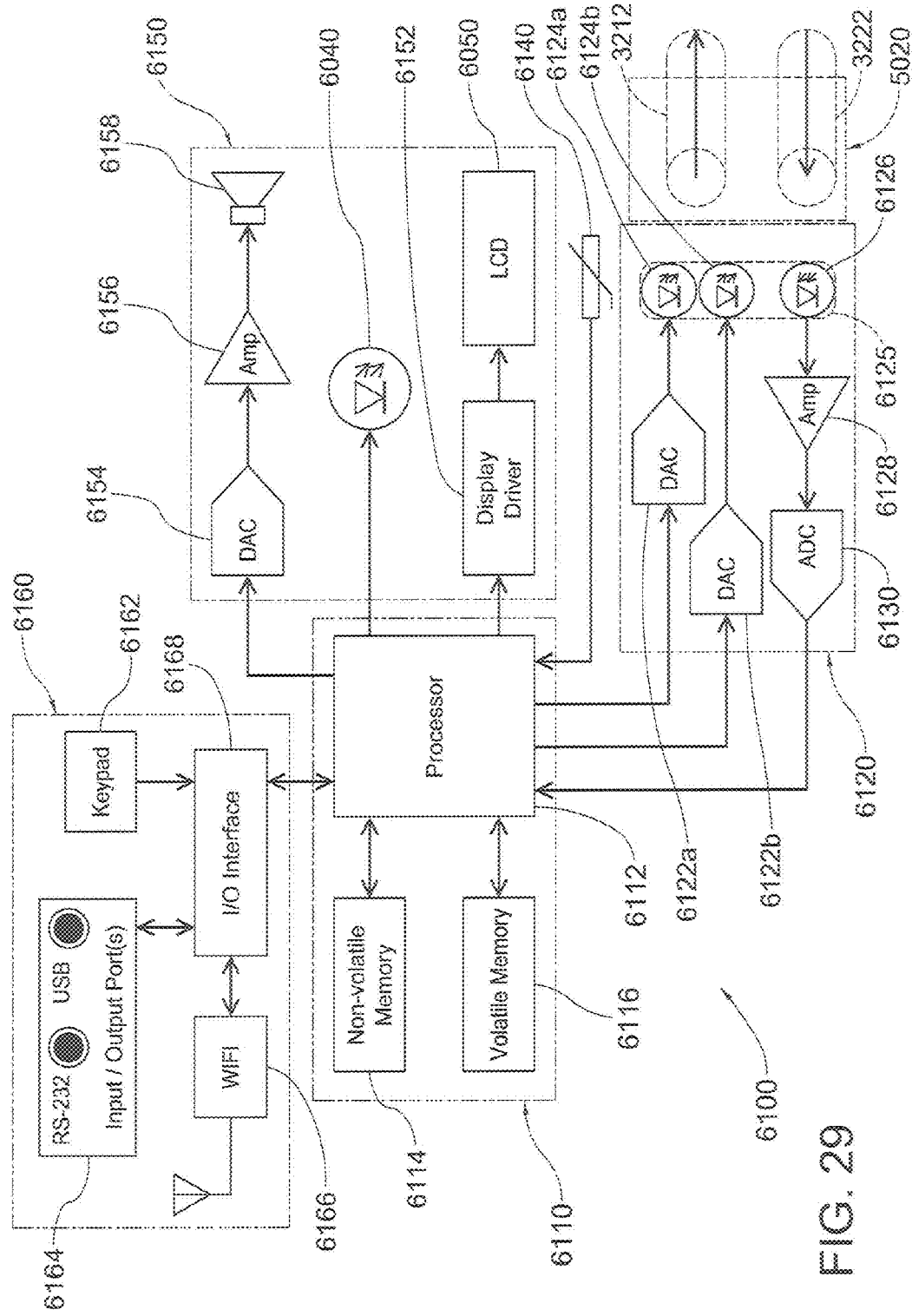
FIG. 29 is a schematic diagram illustrating one embodiment of an operating device of the patient monitoring device shown in FIGS. 28A-28C.

FIG. 29 shows a schematic block diagram of an operating device 6100 according to one embodiment of patient monitoring device 6000. Preferably, operating device 6100 includes a controller 6110, at least one optics bench 6120, a notification section 6150, and an input/output section 6160. Controller 6110 preferably is disposed in the interior space of shell 6010 and includes a processor 6112, non-volatile memory 6114, and volatile memory 6116. According to one embodiment, processor 6112 preferably includes a Peripheral Interface Controller (PIC) microcontroller. An example of a suitable processor 6112 is model number PI32MX695F512L-80I/PT manufactured by Microchip Technology Inc. (Chandler, Ariz., US). Non-volatile memory 6114 preferably includes flash memory or a memory card that is coupled with processor 6112 via a bi-directional communication link. Examples of suitable bi-directional communication links include a serial peripheral interface (SPI) bus, an inter-integrated circuit (I²C) bus, or other serial or parallel communication systems. Preferably, non-volatile memory 6114 extends the non-volatile memory available on processor 6112. According to one embodiment, non-volatile memory 6114 includes a Secure Digital (SD) memory card. Volatile memory 6116 preferably includes, for example, random-access memory (RAM) that is coupled with processor 6112 via a bi-directional communication link. Preferably, volatile memory 6116 extends the volatile memory available on processor 6112. Preferably, controller 6110 performs a number of functions including, inter alia, (1) directing the storage of raw data that is collected via sensor 3000; (2) processing the raw data according to an algorithm running on processor 6112; (3) directing the storage of processed data; (4) issuing commands to notification section 6150; and (5) responding to inputs from input/output section 6160. According to one embodiment, a timestamp is preferably stored with individual units of raw data, processed data and/or log events. Preferably, controller 6110 maintains a log of events related to patient monitoring device 6000. According to other embodiments, operating device 6100 includes an electrical power supply, e.g., a battery, and/or manages electrical power supplied from a source that preferably is external to patient monitoring device 6000. Preferably, an external source of alternating current is transformed and regulated to supply direct current to operating device 6100.

Optics bench 6120 preferably is disposed in the interior space of shell 6010 and includes a first electro-optical signal transducer, a second electro-optical signal transducer, and a third electro-optical signal transducer. Preferably, first and second electro-optical signal transducers transform corresponding first and second digital electric signals from controller 6110 to first and second emitted electromagnetic radiation 3002 and 3012. According to one embodiment, the first electro-optical signal transducer preferably includes a first digital-to-analog converter 6122a and a first light emitting diode 6124a to transform the first digital electric signal to first emitted electromagnetic radiation 3002 at a first peak wavelength $\lambda 1$, and the second electro-optical signal transducer preferably includes a second digital-to-analog converter 6122b and a second light emitting diode 6124b to transform the second digital electric signal to second emitted electromagnetic radiation 3012 at a second peak wavelength $\lambda 2$. According to other embodiments, optics bench 6120 preferably includes additional electro-optical signal transducers to transform additional digital electric signals from controller 6110 to emitted electromagnetic radiation at additional discrete peak wavelengths. The third electro-optical signal transducer of optics bench 6120 preferably includes a photodiode 6126, an operational amplifier 6128 and an analog-to-digital converter 6130 to transform first and second collected electromagnetic radiation 3006 and 3016 to a third digital electric signal. Preferably, the third digital electric signal includes the raw data at each of the first and second peak wavelengths $\lambda 1$ and $\lambda 2$ that is collected by photodiode 6126. According to one embodiment, analog-to-digital converter 6130 preferably transforms the first collected electromagnetic radiation 3006 to a first sequence of values and transforms the second collected electromagnetic radiation 3016 to a second sequence of values. Preferably, the first and second sequences of values are sent to controller 6110 via a bi-directional communication link.

Optics bench 6120 preferably includes a printed circuit board (not shown) that supports first and second digital-to-analog converters 6122a and 6122b, operational amplifier 6128, analog-to-digital converter 6130, and a transceiver 6125 that provides a common enclosure for first light emitting diode 6124a, second light emitting diode 6124b, and photodiode 6126. Preferably, plug 5020 cooperatively mates with transceiver 6125 to provide consistent optical coupling between sensor cable 5000 and optics bench 6120. A bi-directional communication link preferably provides communication between optics bench 6120 and controller 6110. Operating device 6100 shown in FIG. 29 shows a single optics bench 6120 coupled with controller 6110; however, a plurality of optics benches 6120 may be coupled with controller 6110 when, for example, it is preferable to use a single patient monitoring device 6000 with a plurality of electromagnetic radiation sensors 3000.

Preferably, the first wavelength $\lambda 1$ is sensitive to the infusate F and the second wavelength $\lambda 2$ is sensitive to blood. According to one embodiment, the first wavelength $\lambda 1$ is in the near-infrared portion of the electromagnetic spectrum, and the second wavelength $\lambda 2$ is in the yellow to red visible light portions of the electromagnetic spectrum. According to other embodiments, the second wavelength $\lambda 2$ preferably approximates an isosbestic wavelength of oxyhemoglobin and deoxyhemoglobin. Preferably, the second wavelength $\lambda 2$ is approximately at an isosbestic wavelength not greater than 586 nanometers (approximately 512 terahertz) because the next longer isosbestic wavelength at approximately 808 nanometers (approximately 371 terahertz) is sensitive to the infusate F.

Figure 30A:
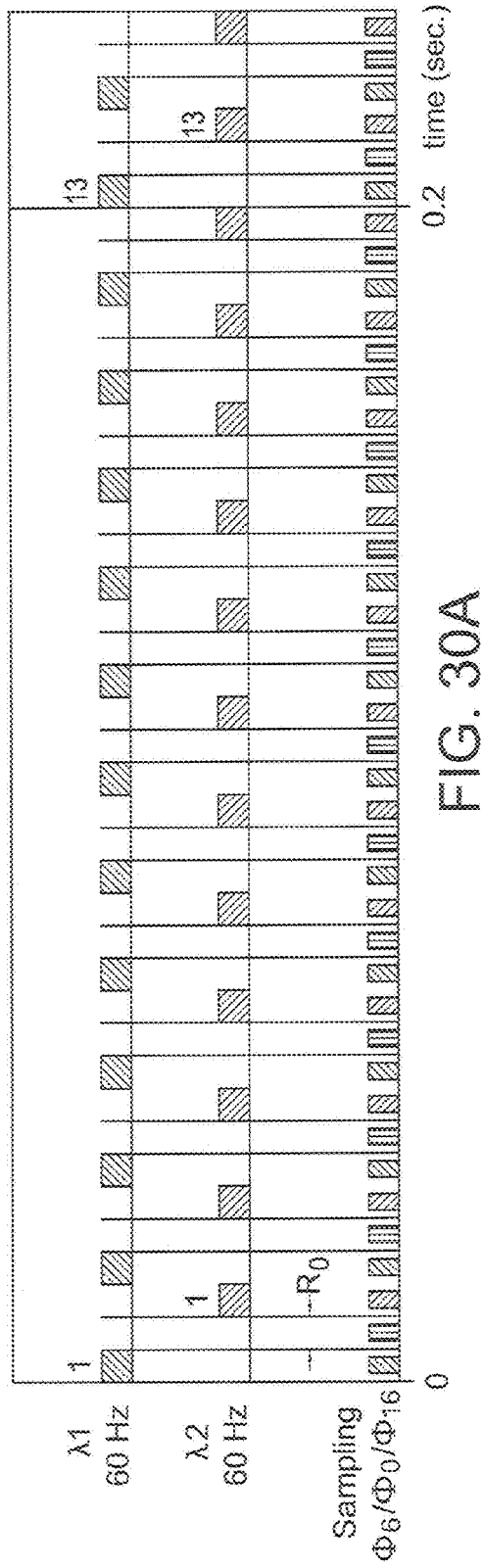
FIGS. 30A and 30B are time lines schematically illustrating embodiments of strategies for controlling the optics bench shown in FIG. 29.
Figure 30B:
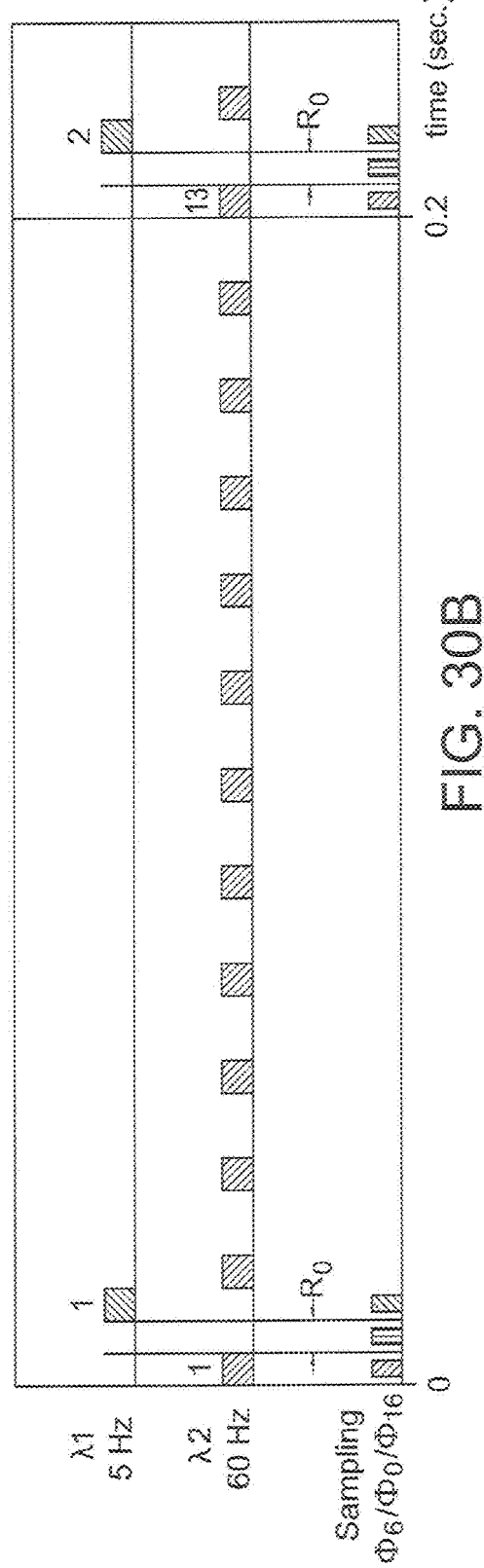

FIGS. 30A and 30B are time lines illustrating embodiments of strategies for controlling the electro-optical signal transducers of optics bench 6120 with controller 6110. According to the embodiment illustrated in FIG. 30A, the first and second electro-optical signal transducers are preferably driven at approximately 60 Hertz by the corresponding first and second digital electric signals from controller 6110. As the terminology is used herein, "drive" preferably refers to a command for cyclically activating and deactivating a device. First and second light emitting diodes 6124a and 6124b therefore are individually activated once per cycle, e.g., twelve times every 0.2 seconds. Preferably, first light emitting diode 6124a is activated during an initial period of each cycle, then there is a middle period $R_0$ during each cycle when first and second light emitting diodes 6124a and 6124b are inactive, and second light emitting diode 6124b is activated during a subsequent period of each cycle. The third digital signal from the third electro-optical signal transducer preferably is sampled three times during each cycle. Preferably, sampling durations are approximately 50% to approximately 75% of the initial, middle, or subsequent periods to isolate corresponding individual samples of (i) the optical power $\Phi_6$; (ii) a optical power $\Phi_0$ that correlates to ambient electromagnetic radiation affecting electromagnetic radiation sensor 3000 (e.g., measured during the middle period $R_0$); and (iii) the optical power $\Phi_{16}$. Accordingly, the third digital signal preferably includes a first set of values including the samples of the optical power $\Phi_6$ from each cycle, a second set of values including the samples of the optical power $\Phi_{16}$ from each cycle, and a third set of values including the samples of the optical power $\Phi_0$ from each cycle.

Second electro-optical signal transducer preferably is driven at a rate that overcomes a perception of flashing by second emitted and collected electromagnetic radiation 3012 and 3016. Preferably, the first electro-optical signal transducer can be driven at a slow rate, e.g., as low as 0.3 Hertz or lower, relative to the second electro-optical signal transducer when first emitted and collected electromagnetic radiation 3002 and 3006 include infrared radiation, which typically is imperceptible to human eyes. According to the embodiment illustrated in FIG. 30B, controller 6110 drives the first electro-optical signal transducer at approximately 5 Hertz while driving the second electro-optical signal transducer at a rate such that second emitted and collected electromagnetic radiation 3012 and 3016 preferably are perceived by human eyes as glowing rather than flashing. Preferably, the second electro-optical signal transducer is driven at a minimum of approximately 24 Hertz and preferably at approximately 60 Hertz. Accordingly, the embodiment illustrated in FIG. 30B shows first light emitting diode 6124a is activated once per cycle, e.g., one time every 0.2 seconds, and second light emitting diode 6124b is activated 12 times per cycle, e.g., 12 times every 0.2 seconds. According to other embodiments, controller 6110 preferably drives the second electro-optical signal transducer at approximately 120 Hertz or more. Similar to the embodiment shown in FIG. 30A, each cycle preferably includes a period of inactivity between activating first and second light emitting diodes 6124a and 6124b. Preferably, second light emitting diode 6124b is activated before first light emitting diode 6124a according to the embodiment illustrated in FIG. 30B. The third digital signal from the third electro-optical signal transducer preferably is sampled three times during each cycle by controller 6110 for obtaining individual samples of the optical power $\Phi_6$, the optical power $\Phi_0$, and the optical power $\Phi_{16}$. The amount of data that is processed by controller 6110 and stored in non-volatile memory 6114 preferably is reduced according to the embodiment illustrated in FIG. 30B principally because individual cycles take longer when the first electro-optical signal transducer is driven at approximately 5 Hertz or less. Other embodiments of control strategies preferably include an adaptable sampling rate for varying the sampling rates and cycle times, e.g., between those of the embodiments illustrated in FIGS. 30A and 30B.

First and second collected electromagnetic radiation 3006 and 3016 preferably are corrected to eliminate or substantially reduce the extraneous contributions of ambient electromagnetic radiation. Preferably, controller 6110 computes corrected values of the optical power $\Phi_6$ and the optical power $\Phi_{16}$ based on the corresponding value of optical power $\Phi_0$ in each cycle. According to one embodiment, controller 6110 subtracts the value of optical power $\Phi_0$ from the values of the optical power $\Phi_6$ and the optical power $\Phi_{16}$ in each cycle. The accuracy of the corrected values of the optical power $\Phi_6$ and the optical power $\Phi_{16}$ preferably increases when there are short intervals, e.g., up to approximately 1 second and preferably approximately 10 milliseconds to approximately 100 milliseconds, between (i) sampling the optical power $\Phi_6$ and the optical power $\Phi_0$; and (ii) sampling the optical power $\Phi_{16}$ and the optical power $\Phi_0$.

The corrected values of the optical power $\Phi_6$ and the optical power $\Phi_{16}$ preferably are normalized according to one embodiment of patient monitoring device 6000 before determining if an infiltration/extravasation examination is indicated or contraindicated. As the terminology is used herein, "normalize" preferably refers to transforming magnitudes of the corrected values of the optical power $\Phi_6$ and the optical power $\Phi_{16}$ to corresponding intensities that can be compared in a meaningful way. According to one embodiment, controller 6110 preferably computes (i) a first arithmetic mean ($\overline{\Phi}_6$ of a first collection of corrected values of the optical power $\Phi_6$; and (ii) a second arithmetic mean ($\overline{\Phi}_{16}$ of a second collection of corrected values of the optical power $\Phi_{16}$. Preferably, the first collection includes a finite number of consecutive corrected values of the optical power $\Phi_6$ beginning with the first cycle, and the second collection includes a finite number of consecutive corrected values of the optical power $\Phi_{16}$ beginning with the first cycle. The finite number(s) preferably correspond to a number of cycles (e.g., 5000 cycles) or a time period (e.g., 5 minutes). Controller 6110 preferably computes a first set of normalized values $\hat{\Phi}_6$ by dividing each corrected value of the optical power $\Phi_6$ by the first arithmetic mean $\overline{\Phi}_6$, and computes a second set of normalized values $\hat{\Phi}_{16}$ by dividing each corrected value of the optical power $\Phi_{16}$ by the second arithmetic mean $\overline{\Phi}_{16}$. Preferably, individual normalized values $\hat{\Phi}_6$ and $\hat{\Phi}_{16}$ are in a range between 0.3 and approximately 1.3. Typically, normalized values less than 1.0 indicate a signal decrease relative to an arithmetic mean and values greater than 1.0 indicate a signal increase relative to the arithmetic mean. Accordingly, the normalized values $\hat{\Phi}_6$ and $\hat{\Phi}_{16}$ are indicative of percentage changes in the first and second collected electromagnetic radiation 3006 and 3016 and are used by controller 6110 in computations to determine if an infiltration/extravasation examination is indicated or contraindicated. According to other embodiments of patient monitoring device 6000, optical power magnitude rather than relative intensity preferably is used in comparisons and/or computations to determine if an infiltration/extravasation examination is indicated or contraindicated. Preferably, values of optical power $\Phi_2$, $\Phi_{12}$ and $\Phi_0$, as well as the uncorrected and corrected values of optical power $\Phi_6$ and $\Phi_{16}$, are measured in or converted to a common unit of optical power, e.g., milliwatts, for use in comparisons or computations by controller 6110.

The requirement to specify finite number(s) of consecutive corrected values preferably is eliminated according to other embodiments. Preferably, controller 6110 analyzes the rates of change of the corrected values of the optical power $\Phi_6$ and the optical power $\Phi_{16}$ and identifies corresponding stable values of optical power when the corresponding rate of change is approximately zero for a preferred duration. Controller 6110 preferably computes sets of normalized values by dividing each corrected value of the optical power by the corresponding stable value rather than dividing by an arithmetic mean. Accordingly, an advantage of analyzing rates of change is that a stable value may be determined in less time than it takes to collect a finite number of corrected values.

Referring again to FIG. 29, patient monitoring device 6000 preferably includes a temperature sensor 6140 to measure temperature changes that affect at least one of first and second light emitting diodes 6124a and 6124b. Typically, the optical power $\Phi$ emanating from first and second light emitting diodes 6124a and 6124b is affected by ambient temperature changes. This accordingly affects the optical power $\Phi_6$ and $\Phi_{16}$ of first and second emitted electromagnetic radiation 3002 and 3012. Temperature sensor 6140 preferably measures the ambient temperature and provides to controller 6110 an electrical signal that may be used to adjust at least one of the first and second digital electrical signal supplied to first and second digital-to-analog converters 6122a and 6122b, respectively. Accordingly, the optical power output of at least one of first and second light emitting diodes 6124a and 6124b may be generally maintained at a preferable level for a given ambient temperature. According to one embodiment, temperature sensor 6140 preferably is disposed in transceiver 6125 in proximity to first and second light emitting diodes 6124a and 6124b. According to other embodiments, temperature sensor 6140 preferably is supported on the printed circuit board for optics bench 6120. According to other embodiments, temperature sensor 6140 preferably is disposed on a printed circuit board for controller 6110. According to other embodiments, temperature sensor 6140 preferably is supported on the exterior of shell 6010.

Notification section 6150 provides visual or audible indications preferably to describe the status of system 100 or to alert a healthcare giver to perform an infiltration/extravasation examination. Preferably, visual indicators in notification section 6150 include indicator set 6040 and display 6050. Display 6050 preferably is coupled to controller 6110 via a display driver 6152. An audible indicator preferably includes a digital-to-analog converter 6154, an audio amplifier 6156, and a speaker 6158. Preferably, display driver 6152 and digital-to-analog converter 6154 communicate with controller 6110 via a communication link. Audio amplifier 6156 preferably drives speaker 6158. According to one embodiment, the output from speaker 6158 includes at least one of an alarm or a notification. Alarms preferably comply with a standard such as IEC 60601-1-8 promulgated by the International Electrotechnical Commission. Preferably, notifications include, for example, a tone, a melody, or a synthesized voice. The embodiment of operating device 6100 shown in FIG. 29 includes a pair of visual indicators and a single audible indicator; however, other combinations of visual and audible indicators are also envisioned.

According to one embodiment, a graphical user interface preferably includes certain features of notification and input/output sections 6150 and 6160. Preferably, the graphical user interface combines in a generally common area on the exterior of shell 6010 at least one of indicator set 6040 and display 6050 with at least one of soft keys 6060, mute button 6070, and check button 6080. For example, patient monitoring device 6000 shown in FIG. 28A includes a graphical user interface that combines, inter alia, labels 6052 on display 6050 with soft keys 6060.

Input/output section 6160 preferably facilitates inputting commands to operating device 6100 or outputting data from operating device 6100. Preferably, input/output section 6160 includes a keypad 6162, at least one input/output port 6164 or wireless communication device 6166, and an input/output interface 6168 to couple keypad 6162, port(s) 6164 and device 6166 to controller 6110 via a bi-directional communication link. According to one embodiment, keypad 6162 includes soft keys 6060, mute button 6070, and check button 6080. According to other embodiments, keypad 6162 preferably includes a keyboard or a touchscreen. According to other embodiments, commands to operating device 6100 preferably are input via a pen device or voice recognition device. Input/output ports(s) 6164 preferably include connections for communicating with peripheral devices according to at least one standard. Examples of suitable communication standards preferably include, e.g., RS-232 and Universal Serial Bus (USB). Wireless communication device 6166 preferably provides an additional or alternate means for communicating with a peripheral device. The embodiment of input/output section 6160 shown in FIG. 29 includes three communication options; however, more or less than three options are also envisioned for enabling operating device 6100 to communicate with peripheral devices.

Algorithm

Algorithms for mitigating false alerts to perform an infiltration/extravasation examination preferably include distinguishing between accumulating fluid and changing tissue blood volume. Preferably, controller 6110 runs an algorithm to analyze the first and second sets of normalized values $\hat{\Phi}_6$ and $\hat{\Phi}_{16}$ for determining if an infiltration/extravasation examination is indicated or contraindicated.

The inventors discovered, inter alia, an infiltration/extravasation examination is indicated when there is an anatomical change over time even when there is a coexistent physiological change. In particular, an infiltration/extravasation examination is indicated when an algorithm determines the infusate F is accumulating in the perivascular tissue P and the tissue blood volume is changing in the monitoring path of electromagnetic radiation sensor 3000. The inventors further discovered, inter alia, an infiltration/extravasation examination is contraindicated when there is a physiological change that is not coexistent with an anatomical change over time. In particular, an infiltration/extravasation examination is contraindicated when an algorithm determines the tissue blood volume is changing in the monitoring path of electromagnetic radiation sensor 3000 and the infusate F is not accumulating in the perivascular tissue P. Preferably, an infiltration/extravasation examination is contraindicated when a tissue blood volume change due to patient posture change is not coexistent with the fluid F infusing the perivascular tissue P.

Several embodiments of algorithms according to the present invention determine whether an infiltration/extravasation examination is indicated or contraindicated. One embodiment of an algorithm preferably analyzes the first set of normalized values $\hat{\Phi}_6$ to evaluate if a change is sensed in the monitoring path of electromagnetic radiation sensor 3000 and analyzes the second set of normalized values $\hat{\Phi}_{16}$ to evaluate if the sensed change is due to a tissue blood volume change rather than an anatomic change over time. Referring to FIGS. 18A-18F, the sizes of the arrows for first and second collected electromagnetic radiation 3006 and 3016 preferably correspond to the optical power $\Phi_2$ and $\Phi_6$. Preferably, the decrease in the optical power $\Phi_6$ from FIG. 18A to FIG. 18C shows that an infiltration/extravasation examination possibly is indicated and a comparison of the relative decreases in the optical power $\Phi_6$ and $\Phi_{16}$ from FIG. 18A to FIG. 18C shows that an infiltration/extravasation examination preferably is indicated. According to one embodiment, the algorithm preferably indicates an infiltration/extravasation examination when (i) the first set of normalized values $\hat{\Phi}_6$ decreases at least approximately 5%; and (ii) the first set of normalized values $\hat{\Phi}_6$ decreases more than the second set of normalized values $\hat{\Phi}_{16}$. According to other embodiments, an infiltration/extravasation examination preferably is indicated by the algorithm when (i) the first set of normalized values $\hat{\Phi}_6$ decreases at least approximately 10%; and (ii) a ratio of the decrease in the second set of normalized values $\hat{\Phi}_{16}$ to the decrease in the first set of normalized values $\hat{\Phi}_6$ is greater than approximately 0.97. Referring to FIGS. 18D and 18F, the decrease in the optical power $\Phi_6$ shows that an infiltration/extravasation examination possibly is indicated and a comparison of the relative decreases in the optical power $\Phi_6$ and $\Phi_{16}$ shows that an infiltration/extravasation examination preferably is contraindicated. According to one embodiment, the algorithm preferably contraindicates an infiltration/extravasation examination when (i) the first set of normalized values $\hat{\Phi}_6$ decreases less than approximately 5%; or (ii) the first set of normalized values $\hat{\Phi}_6$ decreases less than the second set of normalized values $\hat{\Phi}_{16}$. According to other embodiments, an infiltration/extravasation examination preferably is contraindicated by the algorithm when (i) the first set of normalized values $\hat{\Phi}_6$ decreases less than approximately 10%; and (ii) a ratio of the decrease in the second set of normalized values $\hat{\Phi}_{16}$ to the decrease in the first set of normalized values $\hat{\Phi}_6$ is less than approximately 0.9.

Figure 31A:
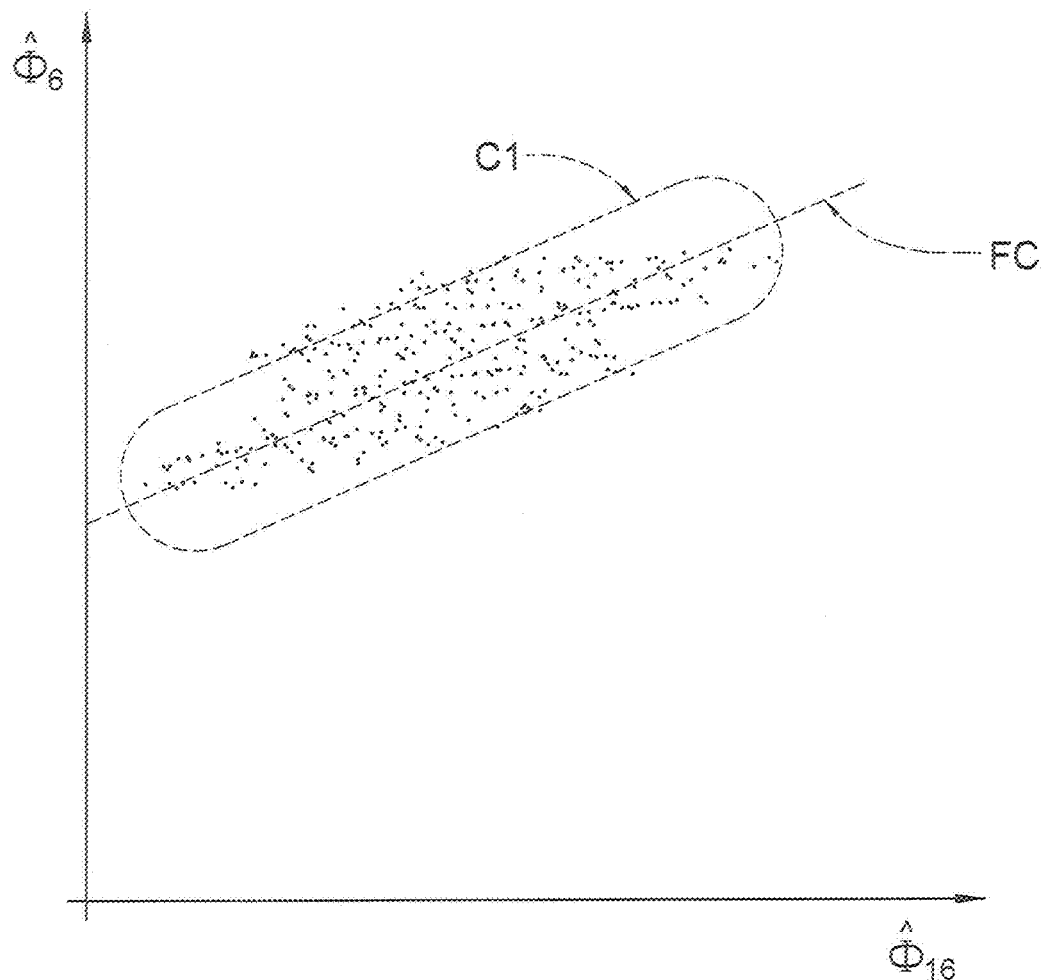
FIGS. 31A and 31B are plots schematically illustrating a relationship between the electromagnetic radiation collected by the electromagnetic radiation sensor shown in FIG. 17. The plots illustrate the normalized optical signals of the infrared radiation versus the visible light when an infiltration/extravasation examination is contraindicated (FIG. 31A) and indicated (FIG. 31B).
Figure 31B:
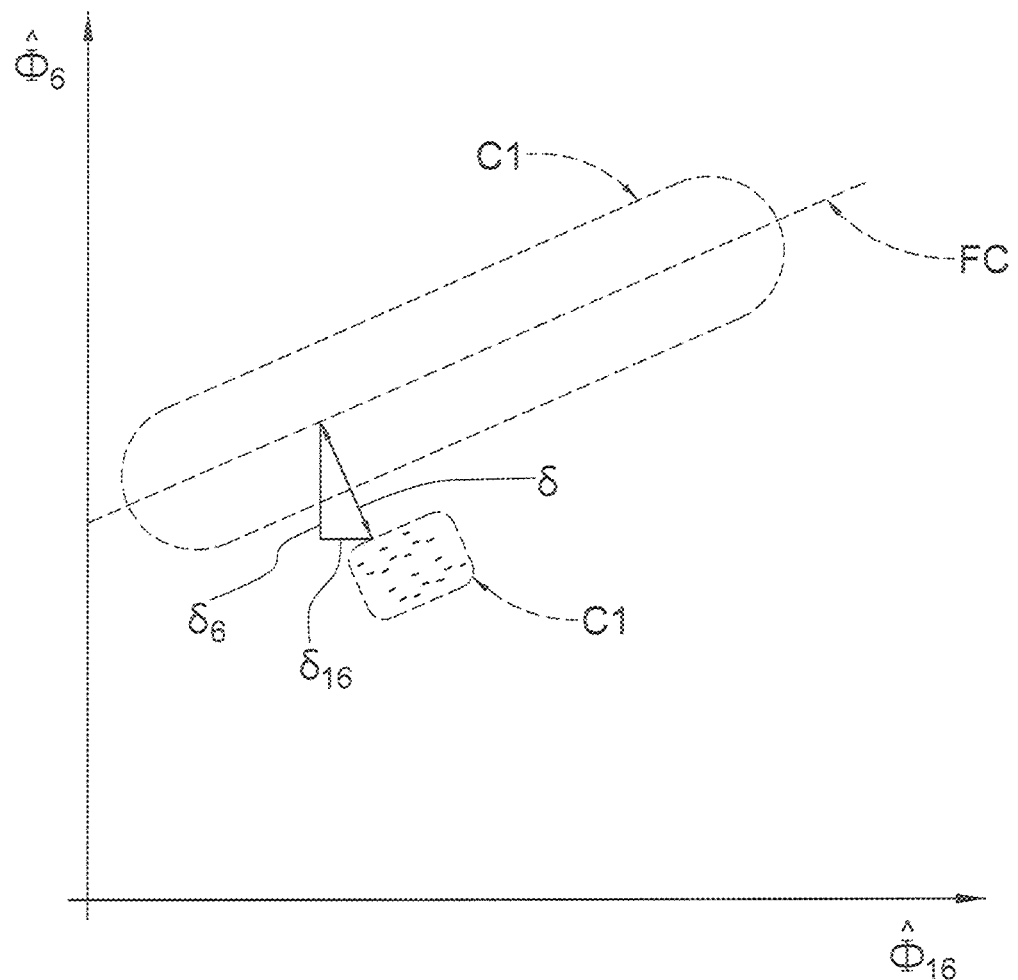

Other embodiments of algorithms according to the present invention preferably are based on changes in ordered pairs of the normalized values $\hat{\Phi}_6$ and $\hat{\Phi}_{16}$ to determine if an infiltration/extravasation examination is indicated or contraindicated. FIG. 31A schematically illustrates individual ordered pairs of the normalized values $\hat{\Phi}_6$ and $\hat{\Phi}_{16}$ plotted for each cycle. Preferably, a known curve fitting technique is used to construct a fitted curve FC for the ordered pairs contained in a first collection C1. The number of ordered pairs in the first collection C1 includes (i) a preferred number of ordered pairs; or (ii) a minimum number of ordered pairs that preferably are sufficient for trending toward one of a group of empirically established fitted curves FC. According to the embodiment shown in FIG. 31A, the fitted curve FC preferably is a straight line described by a first-degree polynomial function, also known as a linear equation. According to other embodiments, the fitted curve FC preferably is described by higher order polynomial functions including, for example, a second-degree polynomial function (quadratic equation) or a third-degree polynomial function (cubic equation). Preferably, ordered pairs that are spaced generally along the fitted curve FC correlate with different tissue blood volume levels and an ordered pair laterally displaced with respect to the fitted curve FC correlates with different structures of the Animalia body. Shifts between ordered pairs that are within the first collection C1 preferably correlate with tissue blood volume changes or generally insubstantial anatomical changes. Preferably, an infiltration/extravasation examination is contraindicated by shifts between ordered pairs within the boundary of the first collection C1. Referring to FIG. 31B, a second collection C2 contains a preferred minimum number of ordered pairs that are at least a preferred minimum perpendicular displacement δ from the fitted curve FC. The ordered pairs in the second collection C2 preferably are collected within a number of cycles that approximately equal the preferred number of ordered pairs in the second collection C2. Preferably, an infiltration/extravasation examination is indicated when the preferred minimum number, e.g., at least approximately 300, of ordered pairs are collected in the second collection C2. According to the embodiment shown in FIG. 31B, the minimum perpendicular displacement δ includes a vertical component $\delta_6$ (e.g., change in the normalized values $\hat{\Phi}_6$) and a horizontal component $\delta_{16}$ (e.g., change in the normalized values $\hat{\Phi}_{16}$). Preferably, an infiltration/extravasation examination is indicated by the algorithm when (i) the vertical component $\delta_6$ decreases at least approximately 5%; and (ii) the horizontal component changes less than the vertical component.

Figure 32A:
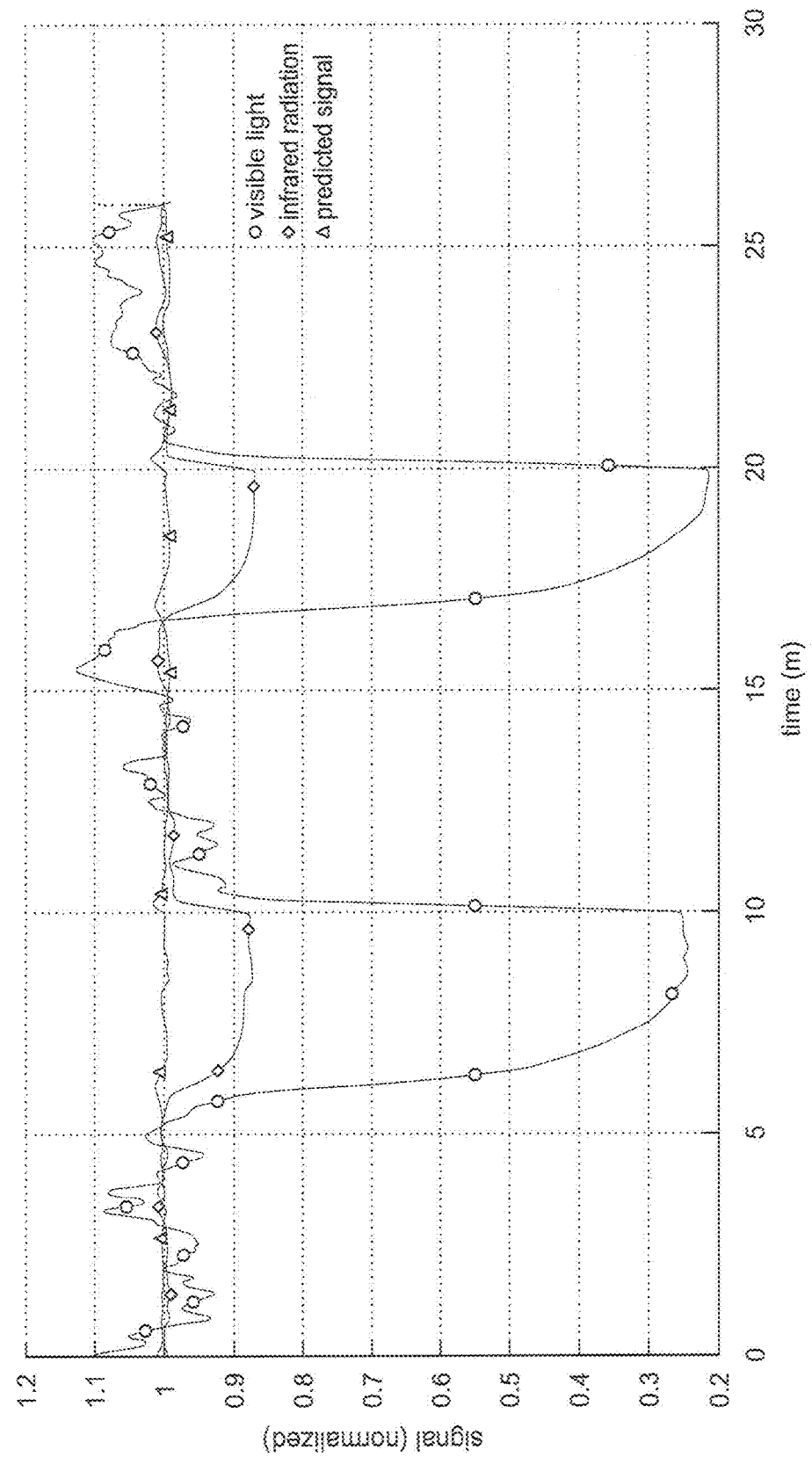
FIGS. 32A and 32B are graphs schematically illustrating normalized signals of the infrared radiation and visible light collected over time by the electromagnetic radiation sensor shown in FIG. 17. A predicted signal based on the normalized signals illustrates when an infiltration/extravasation examination is contraindicated (FIG. 32A) and indicated (FIG. 32B).
Figure 32B:
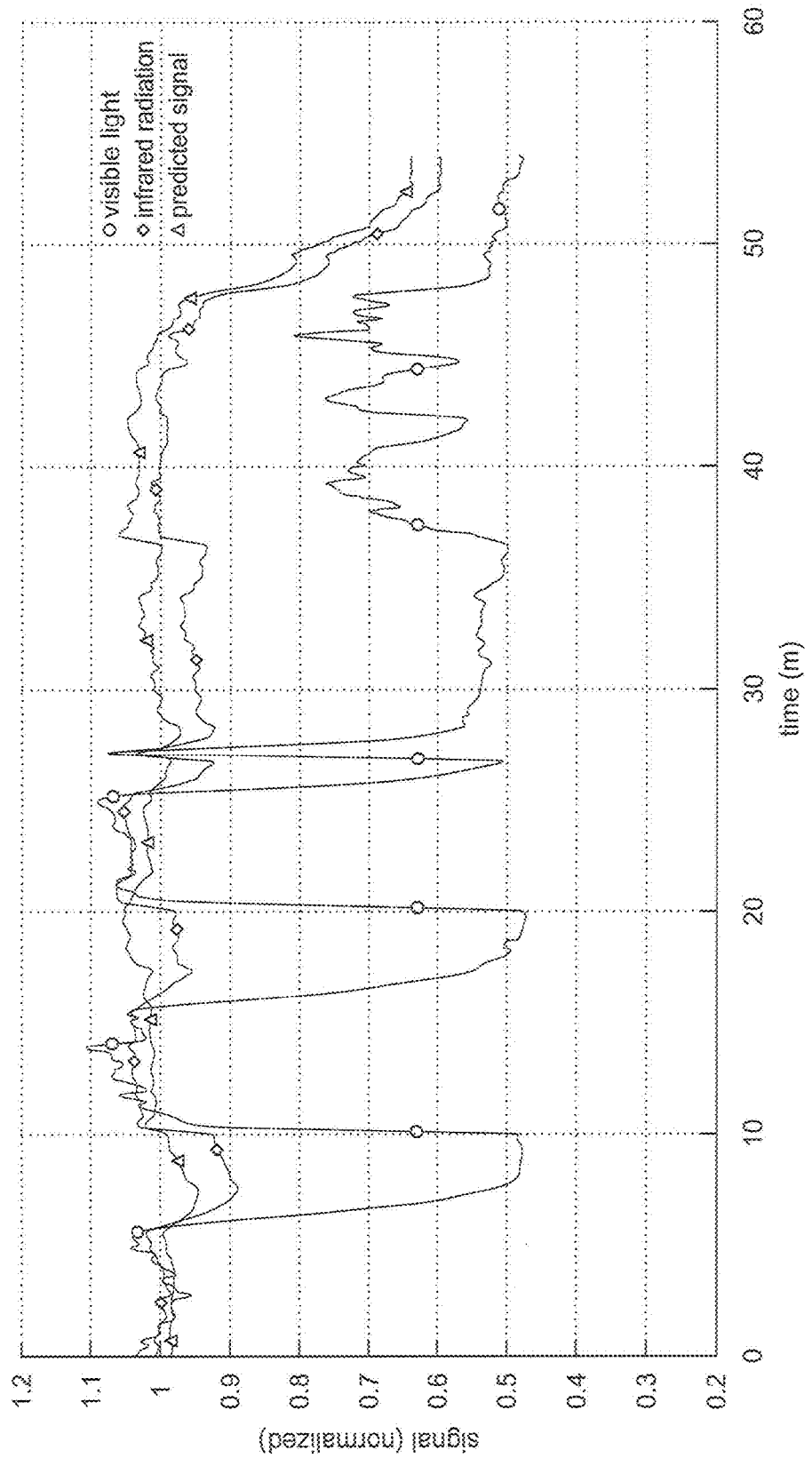

Other embodiments of algorithms according to the present invention compute a predicted signal τ that preferably is compared with a sensed signal for determining if an infiltration/extravasation examination is indicated or contraindicated. Preferably, a calibration function for generating the predicted signal τ is computed by controller 6110 according to the algorithm. FIGS. 32A and 32B schematically illustrate examples of (i) the first set of normalized values $\hat{\Phi}_6$ for an infrared radiation signal; (ii) the second set of normalized values $\hat{\Phi}_{16}$ for a visible light signal; and (iii) the corresponding predicted signal τ. Preferably, coefficients of the calibration function are computed by controller 6110 based on the normalized values $\hat{\Phi}_6$ and $\hat{\Phi}_{16}$ during a finite number of cycles, e.g., similar to the aforementioned use of a known curve fitting technique to describe the fitted curve FC. Similarly also, a preferred minimum number of cycles may be sufficient for trending toward one of a group of empirically established calibration curves. Preferably, controller 6110 computes the predicted signal τ based on the calibration function and the normalized values $\hat{\Phi}_{16}$ for each cycle and then compares the predicted signal τ with the first set of normalized values $\hat{\Phi}_6$. According to one embodiment, an infiltration/extravasation examination is indicated after a preferred number of cycles, e.g., 1000 cycles, during which (i) the predicted signal τ is at least approximately 5% lower; and (ii) the predicted signal τ differs less than approximately 10% from the first set of normalized values $\hat{\Phi}_6$. According to other embodiments, an infiltration/extravasation examination is indicated after approximately 2 minutes during which (i) the predicted signal τ is at least approximately 10% lower; and (ii) the predicted signal τ differs less than approximately 5% from the first set of normalized values $\hat{\Phi}_6$. FIG. 32A shows an embodiment when an infiltration/extravasation examination preferably is contraindicated because the predicted signal τ drop is less than approximately 10%. Drops of at least 10% in the first set of normalized values $\hat{\Phi}_6$ are shown after approximately 7-10 minutes and approximately 18-20 minutes; however, the cause of these drops is determined by the algorithm to be tissue blood volume changes rather than anatomic changes over time. FIG. 32B shows an embodiment when an infiltration/extravasation examination preferably is indicated after approximately 47 minutes when (i) the predicted signal τ drops at least approximately 10%; and (ii) the predicted signal τ and the first set of normalized values $\hat{\Phi}_6$ differ less than approximately 5%.

While the present invention has been disclosed with reference to certain embodiments, numerous modifications, alterations, and changes to the described embodiments are possible without departing from the sphere and scope of the present invention, as defined in the appended claims. For example, dressing 1000 preferably is devoid of materials, e.g., metal, that may harm a patient or damage diagnostic equipment during magnetic resonance imaging, computerized axial tomography, x-rays, or other procedures that use electromagnetic radiation. For another example, operation of the sensor may be reversed, e.g., collecting electromagnetic radiation with a waveguide that is otherwise configured for emission as discussed above and emitting electromagnetic radiation with a waveguide that is otherwise configured for detection as discussed above. For another example, relative sizes of the emission and detection waveguides may be adjusted, e.g., the emission waveguide may include more optical fibers than the detection waveguide and visa-versa. Accordingly, it is intended that the present invention not be limited to the described embodiments, but that it has the full scope defined by the language of the following claims, and equivalents thereof.

TABLE A

| Skin Tissue Layer | Thickness (mm) | Refractive Index | Scattering Coefficient (mm$^{-1}$) | Absorption Coefficient (mm$^{-1}$) |
|---|---|---|---|---|
| epidermis | 0.0875 | 1.5 | 3.10-7.76 | 0.24-0.88 |
| dermis | 1 | 1.4 | 0.93-2.24 | 0.01-0.05 |
| hypodermis | 4 | 1.4 | 1.22-1.60 | 0.01-0.04 |

What is claimed is:

1. A system to aid in diagnosing at least one of infiltration and extravasation in Animalia tissue, the system comprising:

a sensor configured to emit first and second signals entering the Animalia tissue and to detect third and fourth signals exiting the Animalia tissue, the first signal having a peak wavelength between 800 nanometers and 1,050 nanometers, the second signal having a peak wavelength between 560 nanometers and 660 nanometers, the third signal including a portion of the first signal that is at least one of reflected, scattered and redirected from the Animalia tissue, and the fourth signal including a portion of the second signal that is at least one of reflected, scattered and redirected from the Animalia tissue; and a device coupled to the sensor and configured to output a notice based on the third and fourth signals, the device is configured to detect infusate accumulation over time in the Animalia tissue based on the third signal, and the device is configured to detect tissue blood volume changes in the Animalia tissue based on the fourth signal, the device includes:

an analog-to-digital converter configured to (i) represent the third signal with a first sequence of values and (ii) represent the fourth signal with a second sequence of values; and a processor coupled to the analog-to-digital converter, the processor being configured to (i) compute a predicted sequence of values based on the second sequence of values and (ii) compare the first and predicted sequences of values.

2. The system of claim 1 wherein the device comprises an indicator coupled to the processor, the indicator being configured to output the notice when (i) the predicted sequence of values is less than a first threshold value and (ii) the predicted sequence of values and the first sequence of values diverge less than a second threshold value.

3. The system of claim 2 wherein the first threshold value is 0.90 and the second threshold value is 0.05.

* * * * *